United States Patent
Rousso et al.

(10) Patent No.: US 8,610,075 B2
(45) Date of Patent: Dec. 17, 2013

(54) RADIOIMAGING APPLICATIONS OF AND NOVEL FORMULATIONS OF TEBOROXIME

(75) Inventors: Benny Rousso, Rishon-lezion (IL); Dalia Dickman, Misgav (IL); Yael Nir, Caesarea (IL)

(73) Assignee: Biosensors International Group Ltd., Hamilton (BM)

( * ) Notice: Subject to any disclaimer, the term of this patent is extended or adjusted under 35 U.S.C. 154(b) by 105 days.

(21) Appl. No.: 12/514,785

(22) PCT Filed: Nov. 13, 2007

(86) PCT No.: PCT/IL2007/001392
§ 371 (c)(1),
(2), (4) Date: Jan. 18, 2010

(87) PCT Pub. No.: WO2008/059489
PCT Pub. Date: May 22, 2008

(65) Prior Publication Data
US 2010/0140483 A1    Jun. 10, 2010

Related U.S. Application Data

(60) Provisional application No. 60/865,523, filed on Nov. 13, 2006.

(51) Int. Cl.
*G01T 1/161*    (2006.01)

(52) U.S. Cl.
USPC .................. 250/362; 250/363.03; 250/363.04

(58) Field of Classification Search
USPC ............... 250/362, 363.03, 363.04; 424/1.45, 424/1.65; 534/14
See application file for complete search history.

(56) References Cited

U.S. PATENT DOCUMENTS

| | | | |
|---|---|---|---|
| 630,611 A | 8/1899 | Knapp et al. |
| 2,776,377 A | 1/1957 | Anger |
| 3,340,866 A | 9/1967 | Noller |
| 3,446,965 A | 5/1969 | Ogier et al. |
| 3,535,085 A | 10/1970 | Shumate et al. |
| 3,684,887 A | 8/1972 | Hugonin |
| 3,690,309 A | 9/1972 | Pluhnikov et al. |
| 3,719,183 A | 3/1973 | Schwartz |
| 3,739,279 A | 6/1973 | Hollis |

(Continued)

FOREIGN PATENT DOCUMENTS

| | | |
|---|---|---|
| DE | 1516429 | 12/1969 |
| DE | 19814199 | 10/1999 |

(Continued)

OTHER PUBLICATIONS

An Office Action dated Feb. 17, 2011, which issued during the prosecution of Applicant's U.S. Appl. No. 11/932,987.

(Continued)

*Primary Examiner* — Marcus Taningco
(74) *Attorney, Agent, or Firm* — William H. Dippert; Eckert Seamans Cherin & Mellott, LLC

(57) ABSTRACT

A method for cardiac imaging is provided, including administering to an adult human subject an amount of a teboroxime species having a radioactivity of less than 5 mCi at a time of administration, and performing a SPECT imaging procedure of a cardiac region of interest (ROI) of the subject. Other embodiments are also described.

59 Claims, 10 Drawing Sheets

(56) References Cited

U.S. PATENT DOCUMENTS

| | | |
|---|---|---|
| 3,971,362 A | 7/1976 | Pope et al. |
| 3,978,337 A | 8/1976 | Nickles et al. |
| 3,988,585 A | 10/1976 | O'Neill et al. |
| 4,000,502 A | 12/1976 | Butler et al. |
| 4,015,592 A | 4/1977 | Bradley-Moore |
| 4,055,765 A | 10/1977 | Gerber et al. |
| 4,061,919 A | 12/1977 | Miller et al. |
| 4,095,107 A | 6/1978 | Genna et al. |
| 4,165,462 A | 8/1979 | Macovski et al. |
| 4,181,856 A | 1/1980 | Bone |
| 4,278,077 A | 7/1981 | Mizumoto |
| 4,289,969 A | 9/1981 | Cooperstein et al. |
| 4,291,708 A | 9/1981 | Frei et al. |
| 4,296,785 A | 10/1981 | Vitello et al. |
| 4,302,675 A | 11/1981 | Wake et al. |
| 4,364,377 A | 12/1982 | Smith |
| 4,383,327 A | 5/1983 | Kruger |
| 4,476,381 A | 10/1984 | Rubin |
| 4,503,331 A | 3/1985 | Kovacs, Jr. et al. |
| 4,521,688 A | 6/1985 | Yin |
| H12 H | 1/1986 | Bennett et al. |
| 4,580,054 A | 4/1986 | Shimoni |
| 4,595,014 A | 6/1986 | Barrett et al. |
| 4,674,107 A | 6/1987 | Urban et al. |
| 4,679,142 A | 7/1987 | Lee |
| 4,689,041 A | 8/1987 | Corday et al. |
| 4,689,621 A | 8/1987 | Kleinberg |
| 4,709,382 A | 11/1987 | Sones |
| 4,710,624 A | 12/1987 | Alvarez et al. |
| 4,714,605 A | 12/1987 | Feld et al. |
| 4,731,536 A | 3/1988 | Rische et al. |
| 4,773,430 A | 9/1988 | Porath |
| 4,782,840 A | 11/1988 | Martin, Jr. et al. |
| 4,791,934 A * | 12/1988 | Brunnett .................. 600/429 |
| 4,801,803 A | 1/1989 | Denen et al. |
| 4,828,841 A | 5/1989 | Porter et al. |
| 4,834,112 A | 5/1989 | Machek et al. |
| 4,844,067 A | 7/1989 | Ikada et al. |
| 4,844,076 A | 7/1989 | Lesho et al. |
| 4,853,546 A | 8/1989 | Abe et al. |
| 4,854,324 A | 8/1989 | Hirschman et al. |
| 4,854,330 A | 8/1989 | Evans, III et al. |
| 4,867,962 A | 9/1989 | Abrams |
| 4,871,836 A | 10/1989 | Francesconi et al. |
| 4,893,013 A | 1/1990 | Denen et al. |
| 4,893,322 A | 1/1990 | Hellmick et al. |
| 4,919,146 A | 4/1990 | Rhinehart et al. |
| 4,924,486 A | 5/1990 | Weber et al. |
| 4,928,250 A | 5/1990 | Greenberg et al. |
| 4,929,832 A | 5/1990 | Ledley |
| 4,938,230 A | 7/1990 | Machek et al. |
| 4,951,653 A | 8/1990 | Fry et al. |
| 4,959,547 A | 9/1990 | Carroll et al. |
| 4,970,391 A | 11/1990 | Uber, III |
| 4,995,396 A | 2/1991 | Inaba et al. |
| 5,014,708 A | 5/1991 | Hayashi et al. |
| 5,018,182 A | 5/1991 | Cowan et al. |
| 5,032,729 A | 7/1991 | Charpak |
| 5,033,998 A | 7/1991 | Corday et al. |
| 5,039,795 A | 8/1991 | Mueller |
| 5,039,863 A | 8/1991 | Matsuno et al. |
| 5,042,056 A | 8/1991 | Hellmick et al. |
| 5,069,900 A | 12/1991 | Linder |
| 5,070,878 A | 12/1991 | Denen |
| 5,088,492 A | 2/1992 | Takayama et al. |
| 5,115,137 A | 5/1992 | Andersson-Engels et al. |
| 5,118,797 A | 6/1992 | Jurisson et al. |
| 5,119,818 A | 6/1992 | Carroll et al. |
| 5,132,542 A | 7/1992 | Bassalleck et al. |
| 5,145,163 A | 9/1992 | Cowan et al. |
| 5,151,598 A | 9/1992 | Denen |
| 5,170,055 A | 12/1992 | Carroll et al. |
| 5,170,439 A | 12/1992 | Zeng et al. |
| 5,170,789 A | 12/1992 | Narayan et al. |
| 5,183,653 A | 2/1993 | Linder et al. |
| 5,196,796 A | 3/1993 | Misic et al. |
| 5,210,421 A | 5/1993 | Gullberg et al. |
| 5,243,988 A | 9/1993 | Sieben et al. |
| 5,246,005 A | 9/1993 | Carroll et al. |
| 5,249,124 A | 9/1993 | DeVito |
| 5,252,830 A | 10/1993 | Weinberg |
| 5,254,101 A | 10/1993 | Trombley, III |
| 5,258,717 A | 11/1993 | Misic et al. |
| 5,263,077 A | 11/1993 | Cowan et al. |
| 5,279,607 A | 1/1994 | Schentag et al. |
| 5,284,147 A | 2/1994 | Hanaoka et al. |
| 5,299,253 A | 3/1994 | Wessels |
| 5,304,165 A | 4/1994 | Haber et al. |
| 5,307,808 A | 5/1994 | Dumoulin et al. |
| 5,307,814 A | 5/1994 | Kressel et al. |
| 5,309,959 A | 5/1994 | Shaw et al. |
| 5,317,506 A | 5/1994 | Coutre et al. |
| 5,317,619 A | 5/1994 | Hellmick et al. |
| 5,323,006 A | 6/1994 | Thompson et al. |
| 5,329,976 A | 7/1994 | Haber et al. |
| 5,334,141 A | 8/1994 | Carr et al. |
| 5,349,190 A | 9/1994 | Hines et al. |
| 5,355,087 A | 10/1994 | Claiborne et al. |
| 5,365,069 A | 11/1994 | Eisen et al. |
| 5,365,928 A | 11/1994 | Rhinehart et al. |
| 5,367,552 A | 11/1994 | Peschmann |
| 5,377,681 A * | 1/1995 | Drane .................. 600/419 |
| 5,381,791 A | 1/1995 | Qian |
| 5,383,456 A | 1/1995 | Arnold et al. |
| 5,383,858 A | 1/1995 | Reilly et al. |
| 5,386,446 A | 1/1995 | Fujimoto et al. |
| 5,387,409 A * | 2/1995 | Nunn et al. .................. 424/1.45 |
| 5,391,877 A | 2/1995 | Marks |
| 5,395,366 A | 3/1995 | D'Andrea |
| 5,399,868 A | 3/1995 | Jones et al. |
| 5,404,293 A | 4/1995 | Weng et al. |
| 5,415,181 A | 5/1995 | Hofgrefe et al. |
| 5,431,161 A * | 7/1995 | Ryals et al. .................. 600/425 |
| 5,435,302 A | 7/1995 | Lenkinski et al. |
| 5,436,458 A | 7/1995 | Tran et al. |
| 5,441,050 A | 8/1995 | Thurston et al. |
| 5,448,073 A | 9/1995 | Jeanguillaume |
| 5,451,232 A | 9/1995 | Rhinehart et al. |
| 5,472,403 A | 12/1995 | Cornacchia et al. |
| 5,475,219 A | 12/1995 | Olson |
| 5,475,232 A | 12/1995 | Powers et al. |
| 5,476,095 A | 12/1995 | Schnall et al. |
| 5,479,969 A | 1/1996 | Hardie et al. |
| 5,481,115 A | 1/1996 | Hsieh et al. |
| 5,484,384 A | 1/1996 | Fearnot |
| 5,489,782 A | 2/1996 | Wernikoff |
| 5,493,595 A | 2/1996 | Schoolman |
| 5,493,805 A | 2/1996 | Penuela et al. |
| 5,494,036 A | 2/1996 | Uber, III et al. |
| 5,501,674 A | 3/1996 | Trombley, III et al. |
| 5,517,120 A | 5/1996 | Misik et al. |
| 5,519,221 A | 5/1996 | Weinberg |
| 5,519,222 A | 5/1996 | Besett |
| 5,519,931 A | 5/1996 | Reich |
| 5,520,182 A | 5/1996 | Leighton et al. |
| 5,520,653 A | 5/1996 | Reilly et al. |
| 5,521,506 A | 5/1996 | Misic et al. |
| 5,536,945 A | 7/1996 | Reich |
| 5,545,899 A | 8/1996 | Tran et al. |
| 5,559,335 A | 9/1996 | Zeng et al. |
| 5,565,684 A | 10/1996 | Gullberg et al. |
| 5,569,181 A | 10/1996 | Heilman et al. |
| 5,572,132 A | 11/1996 | Pulyer et al. |
| 5,572,999 A | 11/1996 | Funda et al. |
| 5,579,766 A | 12/1996 | Gray |
| 5,580,541 A | 12/1996 | Wells et al. |
| 5,585,637 A | 12/1996 | Bertelsen et al. |
| 5,587,585 A | 12/1996 | Eisen et al. |
| 5,591,143 A | 1/1997 | Trombley, III et al. |
| 5,600,145 A | 2/1997 | Plummer |
| 5,604,531 A | 2/1997 | Iddan et al. |
| 5,610,520 A | 3/1997 | Misic |
| 5,617,858 A | 4/1997 | Taverna et al. |
| 5,629,524 A | 5/1997 | Stettner et al. |

(56) References Cited

U.S. PATENT DOCUMENTS

| | | |
|---|---|---|
| 5,635,717 A | 6/1997 | Popescu |
| 5,657,759 A | 8/1997 | Essen-Moller |
| 5,672,877 A | 9/1997 | Liebig et al. |
| 5,677,539 A | 10/1997 | Apotovsky et al. |
| 5,682,888 A | 11/1997 | Olson et al. |
| 5,687,542 A | 11/1997 | Lawecki et al. |
| 5,690,691 A | 11/1997 | Chen et al. |
| 5,692,640 A | 12/1997 | Caulfield et al. |
| 5,694,933 A | 12/1997 | Madden et al. |
| 5,695,500 A | 12/1997 | Taylor et al. |
| 5,716,595 A | 2/1998 | Goldenberg |
| 5,727,554 A | 3/1998 | Kalend et al. |
| 5,729,129 A | 3/1998 | Acker |
| 5,732,704 A | 3/1998 | Thurston et al. |
| 5,739,508 A | 4/1998 | Uber, III |
| 5,741,232 A | 4/1998 | Reilly et al. |
| 5,742,060 A | 4/1998 | Ashburn |
| 5,744,805 A | 4/1998 | Raylman et al. |
| 5,757,006 A | 5/1998 | De Vito et al. |
| 5,779,675 A | 7/1998 | Reilly et al. |
| 5,780,855 A | 7/1998 | Pare et al. |
| 5,781,442 A | 7/1998 | Engleson et al. |
| 5,784,432 A | 7/1998 | Kurtz et al. |
| 5,786,597 A | 7/1998 | Lingren et al. |
| 5,795,333 A | 8/1998 | Reilly et al. |
| 5,800,355 A | 9/1998 | Hasegawa |
| 5,803,914 A | 9/1998 | Ryals et al. |
| 5,806,519 A | 9/1998 | Evans, III et al. |
| 5,808,203 A | 9/1998 | Nolan, Jr. et al. |
| 5,810,742 A | 9/1998 | Pearlman |
| 5,811,814 A | 9/1998 | Leone et al. |
| 5,813,985 A | 9/1998 | Carroll |
| 5,818,050 A | 10/1998 | Dilmanian et al. |
| 5,821,541 A | 10/1998 | Tumer |
| 5,825,031 A | 10/1998 | Wong et al. |
| 5,827,219 A | 10/1998 | Uber, III et al. |
| 5,828,073 A | 10/1998 | Zhu et al. |
| 5,833,603 A | 11/1998 | Kovacs et al. |
| 5,838,009 A | 11/1998 | Plummer et al. |
| 5,840,026 A | 11/1998 | Uber, III et al. |
| 5,841,141 A | 11/1998 | Gullberg et al. |
| 5,842,977 A | 12/1998 | Lesho et al. |
| 5,843,037 A | 12/1998 | Uber, III |
| 5,846,513 A | 12/1998 | Carroll et al. |
| 5,847,396 A | 12/1998 | Lingren et al. |
| 5,857,463 A | 1/1999 | Thurston et al. |
| 5,871,013 A | 2/1999 | Wainer et al. |
| 5,873,861 A | 2/1999 | Hitchins et al. |
| 5,880,475 A | 3/1999 | Oka et al. |
| 5,882,338 A | 3/1999 | Gray |
| 5,884,457 A | 3/1999 | Ortiz et al. |
| 5,885,216 A | 3/1999 | Evans, III et al. |
| 5,891,030 A | 4/1999 | Johnson et al. |
| 5,893,397 A | 4/1999 | Peterson et al. |
| 5,899,885 A | 5/1999 | Reilly et al. |
| 5,900,533 A | 5/1999 | Chou |
| 5,903,008 A | 5/1999 | Li |
| 5,910,112 A * | 6/1999 | Judd et al. .................... 600/410 |
| 5,911,252 A | 6/1999 | Cassel |
| 5,916,167 A | 6/1999 | Kramer et al. |
| 5,916,197 A | 6/1999 | Reilly et al. |
| 5,920,054 A | 7/1999 | Uber, III |
| 5,927,351 A | 7/1999 | Zhu et al. |
| 5,928,150 A | 7/1999 | Call |
| 5,932,879 A | 8/1999 | Raylman et al. |
| 5,938,639 A | 8/1999 | Reilly et al. |
| 5,939,724 A | 8/1999 | Eisen et al. |
| 5,944,190 A | 8/1999 | Edelen |
| 5,944,694 A | 8/1999 | Hitchins et al. |
| 5,947,935 A | 9/1999 | Rhinehart et al. |
| 5,953,884 A | 9/1999 | Lawecki et al. |
| 5,954,668 A | 9/1999 | Uber, III et al. |
| 5,961,457 A | 10/1999 | Raylman et al. |
| 5,967,983 A | 10/1999 | Ashburn |
| 5,973,598 A | 10/1999 | Beigel |
| 5,974,165 A | 10/1999 | Giger et al. |
| 5,984,860 A | 11/1999 | Shan |
| 5,987,350 A | 11/1999 | Thurston |
| 5,993,378 A | 11/1999 | Lemelson |
| 5,997,502 A | 12/1999 | Reilly et al. |
| 6,002,134 A | 12/1999 | Lingren |
| 6,002,480 A | 12/1999 | Izatt et al. |
| 6,017,330 A | 1/2000 | Hitchins et al. |
| 6,019,745 A | 2/2000 | Gray |
| 6,021,341 A | 2/2000 | Scibilia et al. |
| 6,026,317 A | 2/2000 | Verani |
| 6,037,595 A | 3/2000 | Lingren |
| 6,040,697 A | 3/2000 | Misic |
| 6,042,565 A | 3/2000 | Hirschman et al. |
| RE36,648 E | 4/2000 | Uber, III et al. |
| 6,046,454 A | 4/2000 | Lingren et al. |
| 6,048,334 A | 4/2000 | Hirschman et al. |
| 6,052,618 A | 4/2000 | Dahlke et al. |
| 6,055,450 A | 4/2000 | Ashburn |
| 6,055,452 A | 4/2000 | Pearlman |
| RE36,693 E | 5/2000 | Reich |
| 6,063,052 A | 5/2000 | Uber et al. |
| D426,891 S | 6/2000 | Beale et al. |
| D426,892 S | 6/2000 | Beale et al. |
| 6,072,177 A | 6/2000 | McCroskey et al. |
| 6,076,009 A | 6/2000 | Raylman et al. |
| 6,080,984 A | 6/2000 | Friesenhahn |
| D428,491 S | 7/2000 | Beale et al. |
| 6,082,366 A | 7/2000 | Andra et al. |
| 6,090,064 A | 7/2000 | Reilly et al. |
| 6,091,070 A | 7/2000 | Lingren et al. |
| 6,096,011 A | 8/2000 | Trombley, III et al. |
| 6,107,102 A | 8/2000 | Ferrari |
| 6,115,635 A | 9/2000 | Bourgeois |
| 6,129,670 A | 10/2000 | Burdette et al. |
| 6,132,372 A | 10/2000 | Essen-Moller |
| 6,135,955 A | 10/2000 | Madden et al. |
| 6,135,968 A | 10/2000 | Brounstein |
| 6,137,109 A | 10/2000 | Hayes |
| 6,145,277 A | 11/2000 | Lawecki et al. |
| 6,147,352 A | 11/2000 | Ashburn |
| 6,147,353 A | 11/2000 | Gagnon et al. |
| 6,148,229 A | 11/2000 | Morris, Sr. et al. |
| 6,149,627 A | 11/2000 | Uber, III |
| 6,155,485 A | 12/2000 | Coughlin et al. |
| 6,160,398 A | 12/2000 | Walsh |
| 6,162,198 A | 12/2000 | Coffey et al. |
| 6,172,362 B1 | 1/2001 | Lingren et al. |
| 6,173,201 B1 | 1/2001 | Front |
| 6,184,530 B1 | 2/2001 | Hines et al. |
| 6,189,195 B1 | 2/2001 | Reilly et al. |
| 6,194,715 B1 | 2/2001 | Lingren et al. |
| 6,194,725 B1 | 2/2001 | Colsher et al. |
| 6,194,726 B1 | 2/2001 | Pi et al. |
| 6,197,000 B1 | 3/2001 | Reilly et al. |
| 6,202,923 B1 | 3/2001 | Boyer et al. |
| 6,203,775 B1 | 3/2001 | Torchilin et al. |
| 6,205,347 B1 | 3/2001 | Morgan et al. |
| 6,212,423 B1 | 4/2001 | Krakovitz |
| 6,223,065 B1 | 4/2001 | Misic et al. |
| 6,224,577 B1 | 5/2001 | Dedola et al. |
| 6,226,350 B1 | 5/2001 | Hsieh |
| 6,229,145 B1 | 5/2001 | Weinberg |
| 6,232,605 B1 | 5/2001 | Soluri et al. |
| 6,233,304 B1 | 5/2001 | Hu et al. |
| 6,236,050 B1 | 5/2001 | Tumer |
| 6,236,878 B1 | 5/2001 | Taylor et al. |
| 6,236,880 B1 | 5/2001 | Raylman et al. |
| 6,239,438 B1 | 5/2001 | Schubert |
| 6,240,312 B1 | 5/2001 | Alfano et al. |
| 6,241,708 B1 | 6/2001 | Reilly et al. |
| 6,242,743 B1 | 6/2001 | DeVito |
| 6,242,744 B1 | 6/2001 | Soluri et al. |
| 6,242,745 B1 | 6/2001 | Berlad et al. |
| 6,246,901 B1 | 6/2001 | Benaron |
| 6,252,924 B1 | 6/2001 | Davantes et al. |
| 6,258,576 B1 | 7/2001 | Richards-Kortum et al. |
| 6,259,095 B1 | 7/2001 | Bouton et al. |
| 6,261,562 B1 | 7/2001 | Xu et al. |

(56) References Cited

U.S. PATENT DOCUMENTS

| | | |
|---|---|---|
| 6,263,229 B1 | 7/2001 | Atalar et al. |
| 6,269,340 B1 | 7/2001 | Ford et al. |
| 6,270,463 B1 | 8/2001 | Morris, Sr. et al. |
| 6,271,524 B1 | 8/2001 | Wainer et al. |
| 6,271,525 B1 | 8/2001 | Majewski et al. |
| 6,280,704 B1 | 8/2001 | Schutt et al. |
| 6,281,505 B1 | 8/2001 | Hines et al. |
| 6,308,097 B1 | 10/2001 | Pearlman |
| 6,310,968 B1 | 10/2001 | Hawkins et al. |
| 6,315,981 B1 | 11/2001 | Unger |
| 6,317,623 B1 | 11/2001 | Griffiths et al. |
| 6,317,648 B1 | 11/2001 | Sleep et al. |
| 6,318,630 B1 | 11/2001 | Coughlin et al. |
| 6,322,535 B1 | 11/2001 | Hitchins et al. |
| 6,323,648 B1 | 11/2001 | Belt et al. |
| 6,324,418 B1 | 11/2001 | Crowley et al. |
| RE37,487 E | 12/2001 | Reilly et al. |
| D452,737 S | 1/2002 | Nolan, Jr. et al. |
| 6,336,913 B1 | 1/2002 | Spohn et al. |
| 6,339,652 B1 | 1/2002 | Hawkins et al. |
| 6,339,718 B1 | 1/2002 | Zatezalo et al. |
| 6,344,745 B1 | 2/2002 | Reisker et al. |
| 6,346,706 B1 | 2/2002 | Rogers et al. |
| 6,346,886 B1 | 2/2002 | de la Huerga |
| RE37,602 E | 3/2002 | Uber, III et al. |
| 6,353,227 B1 | 3/2002 | Boxen |
| 6,356,081 B1 | 3/2002 | Misic |
| 6,368,331 B1 | 4/2002 | Front et al. |
| 6,371,938 B1 | 4/2002 | Reilly et al. |
| 6,375,624 B1 | 4/2002 | Uber, III et al. |
| 6,377,838 B1 | 4/2002 | Iwanczyk et al. |
| 6,381,349 B1 | 4/2002 | Zeng et al. |
| 6,385,483 B1 | 5/2002 | Uber, III et al. |
| 6,388,258 B1 | 5/2002 | Berlad et al. |
| 6,392,235 B1 | 5/2002 | Barrett et al. |
| 6,396,273 B2 | 5/2002 | Misic |
| 6,397,098 B1 | 5/2002 | Uber, III et al. |
| 6,399,951 B1 | 6/2002 | Paulus et al. |
| 6,402,717 B1 | 6/2002 | Reilly et al. |
| 6,402,718 B1 | 6/2002 | Reilly et al. |
| 6,407,391 B1 | 6/2002 | Mastrippolito et al. |
| 6,408,204 B1 | 6/2002 | Hirschman |
| 6,409,987 B1 * | 6/2002 | Cardin et al. ............... 424/1.73 |
| 6,415,046 B1 | 7/2002 | Kerut, Sr. |
| 6,420,711 B2 | 7/2002 | Teumer |
| 6,425,174 B1 | 7/2002 | Reich |
| 6,426,917 B1 | 7/2002 | Tabanou et al. |
| 6,429,431 B1 | 8/2002 | Wilk |
| 6,431,175 B1 | 8/2002 | Penner et al. |
| 6,432,089 B1 | 8/2002 | Kakimi et al. |
| 6,438,401 B1 | 8/2002 | Cheng et al. |
| 6,439,444 B1 | 8/2002 | Shields, II |
| 6,440,107 B1 | 8/2002 | Trombley, III et al. |
| 6,442,418 B1 | 8/2002 | Evans, III et al. |
| 6,448,560 B1 | 9/2002 | Tumer |
| 6,453,199 B1 | 9/2002 | Kobozev |
| 6,459,925 B1 | 10/2002 | Nields et al. |
| 6,459,931 B1 | 10/2002 | Hirschman |
| 6,468,261 B1 | 10/2002 | Small et al. |
| 6,469,306 B1 | 10/2002 | Van Dulmen et al. |
| 6,471,674 B1 | 10/2002 | Emig et al. |
| 6,480,732 B1 | 11/2002 | Tanaka et al. |
| 6,484,051 B1 | 11/2002 | Daniel |
| 6,488,661 B1 | 12/2002 | Spohn et al. |
| 6,490,476 B1 | 12/2002 | Townsend et al. |
| 6,504,157 B2 | 1/2003 | Juhi |
| 6,504,178 B2 | 1/2003 | Carlson et al. |
| 6,504,899 B2 | 1/2003 | Pugachev et al. |
| 6,506,155 B2 | 1/2003 | Sluis et al. |
| 6,510,336 B1 | 1/2003 | Daghighian et al. |
| 6,512,374 B1 | 1/2003 | Misic et al. |
| 6,516,213 B1 | 2/2003 | Nevo |
| 6,519,569 B1 | 2/2003 | White et al. |
| 6,520,930 B2 | 2/2003 | Critchlow et al. |
| 6,522,945 B2 | 2/2003 | Sleep et al. |
| 6,525,320 B1 | 2/2003 | Juni |
| 6,525,321 B2 | 2/2003 | Juni |
| 6,541,763 B2 | 4/2003 | Lingren et al. |
| 6,545,280 B2 | 4/2003 | Weinberg et al. |
| 6,549,646 B1 | 4/2003 | Yeh et al. |
| 6,560,354 B1 | 5/2003 | Maurer et al. |
| 6,562,008 B1 | 5/2003 | Reilly et al. |
| 6,563,942 B2 | 5/2003 | Takeo et al. |
| 6,565,502 B1 | 5/2003 | Bede et al. |
| 6,567,687 B2 | 5/2003 | Front et al. |
| 6,575,930 B1 | 6/2003 | Trombley, III et al. |
| 6,576,918 B1 | 6/2003 | Fu et al. |
| 6,584,348 B2 | 6/2003 | Glukhovsky |
| 6,585,700 B1 | 7/2003 | Trocki et al. |
| 6,587,710 B1 | 7/2003 | Wainer |
| 6,589,158 B2 | 7/2003 | Winkler |
| 6,591,127 B1 | 7/2003 | McKinnon |
| 6,592,520 B1 | 7/2003 | Peszynski et al. |
| 6,602,488 B1 | 8/2003 | Daghighian |
| 6,607,301 B1 | 8/2003 | Glukhovsky et al. |
| 6,611,141 B1 | 8/2003 | Schulz et al. |
| 6,614,453 B1 | 9/2003 | Suri et al. |
| 6,620,134 B1 | 9/2003 | Trombley, III et al. |
| 6,627,893 B1 | 9/2003 | Zeng et al. |
| 6,628,983 B1 | 9/2003 | Gagnon |
| 6,628,984 B2 | 9/2003 | Weinberg |
| 6,630,735 B1 | 10/2003 | Carlson et al. |
| 6,631,284 B2 | 10/2003 | Nutt et al. |
| 6,632,216 B2 | 10/2003 | Houzego et al. |
| 6,633,658 B1 | 10/2003 | Dabney et al. |
| 6,638,752 B2 | 10/2003 | Contag et al. |
| 6,643,537 B1 | 11/2003 | Zatezalo et al. |
| 6,643,538 B1 | 11/2003 | Majewski et al. |
| 6,652,489 B2 | 11/2003 | Trocki et al. |
| 6,657,200 B2 | 12/2003 | Nygard et al. |
| 6,662,036 B2 | 12/2003 | Cosman |
| 6,664,542 B2 | 12/2003 | Ye et al. |
| 6,670,258 B2 | 12/2003 | Carlson et al. |
| 6,671,563 B1 | 12/2003 | Engelson et al. |
| 6,673,033 B1 | 1/2004 | Sciulli et al. |
| 6,674,834 B1 | 1/2004 | Acharya et al. |
| 6,676,634 B1 | 1/2004 | Spohn et al. |
| 6,677,182 B2 | 1/2004 | Carlson et al. |
| 6,677,755 B2 | 1/2004 | Belt et al. |
| 6,680,750 B1 | 1/2004 | Tournier et al. |
| 6,694,172 B1 | 2/2004 | Gagnon et al. |
| 6,697,660 B1 | 2/2004 | Robinson |
| 6,699,219 B2 | 3/2004 | Emig et al. |
| 6,704,592 B1 | 3/2004 | Reynolds et al. |
| 6,713,766 B2 | 3/2004 | Garrard et al. |
| 6,714,012 B2 | 3/2004 | Belt et al. |
| 6,714,013 B2 | 3/2004 | Misic |
| 6,716,195 B2 | 4/2004 | Nolan, Jr. et al. |
| 6,722,499 B2 | 4/2004 | Reich |
| 6,723,988 B1 | 4/2004 | Wainer |
| 6,726,657 B1 | 4/2004 | Dedig et al. |
| 6,728,583 B2 | 4/2004 | Hallett |
| 6,731,971 B2 | 5/2004 | Evans, III et al. |
| 6,731,989 B2 | 5/2004 | Engleson et al. |
| 6,733,477 B2 | 5/2004 | Cowan et al. |
| 6,733,478 B2 | 5/2004 | Reilly et al. |
| 6,734,416 B2 | 5/2004 | Carlson et al. |
| 6,734,430 B2 | 5/2004 | Soluri et al. |
| 6,737,652 B2 | 5/2004 | Lanza et al. |
| 6,737,866 B2 | 5/2004 | Belt et al. |
| 6,740,882 B2 | 5/2004 | Weinberg et al. |
| 6,743,202 B2 | 6/2004 | Hirschman et al. |
| 6,743,205 B2 | 6/2004 | Nolan, Jr. et al. |
| 6,747,454 B2 | 6/2004 | Belt |
| 6,748,259 B1 | 6/2004 | Benaron et al. |
| 6,751,500 B2 | 6/2004 | Hirschman et al. |
| 6,765,981 B2 | 7/2004 | Heumann |
| 6,766,048 B1 | 7/2004 | Launay et al. |
| 6,767,319 B2 | 7/2004 | Reilly et al. |
| 6,771,802 B1 | 8/2004 | Patt et al. |
| 6,774,358 B2 | 8/2004 | Hamill et al. |
| 6,776,977 B2 | 8/2004 | Liu |
| 6,787,777 B1 | 9/2004 | Gagnon et al. |
| 6,788,758 B2 | 9/2004 | De Villiers |

(56) References Cited

U.S. PATENT DOCUMENTS

| | | | |
|---|---|---|---|
| 6,798,206 B2 | 9/2004 | Misic | |
| 6,808,513 B2 | 10/2004 | Reilly et al. | |
| 6,813,868 B2 | 11/2004 | Baldwin et al. | |
| 6,821,013 B2 | 11/2004 | Reilly et al. | |
| 6,822,237 B2 | 11/2004 | Inoue et al. | |
| 6,833,705 B2 | 12/2004 | Misic | |
| 6,838,672 B2 | 1/2005 | Wagenaar et al. | |
| 6,841,782 B1 | 1/2005 | Balan et al. | |
| 6,843,357 B2 | 1/2005 | Bybee et al. | |
| 6,851,615 B2 | 2/2005 | Jones | |
| 6,866,654 B2 | 3/2005 | Callan et al. | |
| 6,870,175 B2 | 3/2005 | Dell et al. | |
| 6,881,043 B2 | 4/2005 | Barak | |
| 6,888,351 B2 | 5/2005 | Belt et al. | |
| 6,889,074 B2 | 5/2005 | Uber, III et al. | |
| 6,897,658 B2 | 5/2005 | Belt et al. | |
| 6,906,330 B2 | 6/2005 | Blevis et al. | |
| D507,832 S | 7/2005 | Yanniello et al. | |
| 6,915,170 B2 | 7/2005 | Engleson et al. | |
| 6,915,823 B2 | 7/2005 | Osborne et al. | |
| 6,917,828 B2 | 7/2005 | Fukuda | |
| 6,921,384 B2 | 7/2005 | Reilly et al. | |
| 6,928,142 B2 | 8/2005 | Shao et al. | |
| 6,935,560 B2 | 8/2005 | Andreasson et al. | |
| 6,936,030 B1 | 8/2005 | Pavlik et al. | |
| 6,937,750 B2 | 8/2005 | Natanzon et al. | |
| 6,939,302 B2 | 9/2005 | Griffiths et al. | |
| 6,940,070 B2 | 9/2005 | Tumer | |
| 6,943,355 B2 | 9/2005 | Shwartz et al. | |
| 6,957,522 B2 | 10/2005 | Baldwin et al. | |
| 6,958,053 B1 | 10/2005 | Reilly | |
| 6,963,770 B2 | 11/2005 | Scarantino et al. | |
| 6,970,735 B2 | 11/2005 | Uber, III et al. | |
| 6,972,001 B2 | 12/2005 | Emig et al. | |
| 6,974,443 B2 | 12/2005 | Reilly et al. | |
| 6,976,349 B2 | 12/2005 | Baldwin et al. | |
| 6,984,222 B1 | 1/2006 | Hitchins et al. | |
| 6,985,870 B2 | 1/2006 | Martucci et al. | |
| 6,988,981 B2 | 1/2006 | Hamazaki | |
| 6,994,249 B2 | 2/2006 | Peterka et al. | |
| 7,011,814 B2 | 3/2006 | Suddarth et al. | |
| 7,012,430 B2 | 3/2006 | Misic | |
| 7,017,622 B2 | 3/2006 | Osborne et al. | |
| 7,018,363 B2 | 3/2006 | Cowan et al. | |
| 7,019,783 B2 | 3/2006 | Kindem et al. | |
| 7,025,757 B2 | 4/2006 | Reilly et al. | |
| 7,026,623 B2 * | 4/2006 | Oaknin et al. | 250/363.04 |
| 7,043,063 B1 | 5/2006 | Noble et al. | |
| 7,102,138 B2 | 9/2006 | Belvis et al. | |
| 7,103,204 B1 | 9/2006 | Celler et al. | |
| 7,127,026 B2 | 10/2006 | Amemiya et al. | |
| 7,142,634 B2 | 11/2006 | Engler et al. | |
| 7,145,986 B2 | 12/2006 | Wear et al. | |
| 7,147,372 B2 | 12/2006 | Nelson et al. | |
| 7,164,130 B2 | 1/2007 | Welsh et al. | |
| 7,176,466 B2 | 2/2007 | Rousso et al. | |
| 7,187,790 B2 | 3/2007 | Sabol et al. | |
| 7,217,953 B2 | 5/2007 | Carlson | |
| 7,256,386 B2 | 8/2007 | Carlson et al. | |
| 7,327,822 B2 | 2/2008 | Sauer et al. | |
| 7,359,535 B2 | 4/2008 | Salla et al. | |
| 7,373,197 B2 | 5/2008 | Daighighian et al. | |
| 7,394,923 B2 | 7/2008 | Zou et al. | |
| 7,402,813 B2 | 7/2008 | Ben-Haim et al. | |
| 7,444,010 B2 | 10/2008 | De Man | |
| 7,468,513 B2 | 12/2008 | Charron et al. | |
| 7,490,085 B2 | 2/2009 | Walker et al. | |
| 7,495,225 B2 | 2/2009 | Hefetz et al. | |
| 7,502,499 B2 | 3/2009 | Grady | |
| 7,570,732 B2 | 8/2009 | Stanton et al. | |
| 7,592,597 B2 | 9/2009 | Hefetz et al. | |
| 7,620,444 B2 | 11/2009 | Le et al. | |
| 7,627,084 B2 | 12/2009 | Jabri et al. | |
| 7,671,331 B2 | 3/2010 | Hefetz | |
| 7,671,340 B2 | 3/2010 | Uribe et al. | |
| 7,672,491 B2 | 3/2010 | Krishnan et al. | |
| 7,680,240 B2 | 3/2010 | Manjeshwar et al. | |
| 7,705,316 B2 | 4/2010 | Rousso et al. | |
| 7,734,331 B2 | 6/2010 | Dhawale et al. | |
| 7,826,889 B2 | 11/2010 | David et al. | |
| 7,831,024 B2 | 11/2010 | Metzler et al. | |
| 7,835,927 B2 | 11/2010 | Schlotterbeck et al. | |
| 7,894,650 B2 | 2/2011 | Weng et al. | |
| 7,968,851 B2 | 6/2011 | Rousso et al. | |
| 8,158,951 B2 | 4/2012 | Bal et al. | |
| 2001/0016029 A1 | 8/2001 | Tumer | |
| 2001/0020131 A1 | 9/2001 | Kawagishi et al. | |
| 2001/0035902 A1 | 11/2001 | Iddan et al. | |
| 2001/0049608 A1 | 12/2001 | Hochman | |
| 2002/0068864 A1 | 6/2002 | Bishop et al. | |
| 2002/0072784 A1 | 6/2002 | Sheppard et al. | |
| 2002/0085748 A1 | 7/2002 | Baumberg | |
| 2002/0087101 A1 | 7/2002 | Barrick et al. | |
| 2002/0099295 A1 | 7/2002 | Gil et al. | |
| 2002/0099310 A1 | 7/2002 | Kimchy et al. | |
| 2002/0099334 A1 | 7/2002 | Hanson et al. | |
| 2002/0103429 A1 | 8/2002 | DeCharms | |
| 2002/0103431 A1 | 8/2002 | Toker et al. | |
| 2002/0145114 A1 | 10/2002 | Inoue et al. | |
| 2002/0148970 A1 | 10/2002 | Wong et al. | |
| 2002/0165491 A1 | 11/2002 | Reilly | |
| 2002/0168094 A1 | 11/2002 | Kaushikkar et al. | |
| 2002/0168317 A1 | 11/2002 | Daighighian et al. | |
| 2002/0172405 A1 | 11/2002 | Schultz | |
| 2002/0179843 A1 | 12/2002 | Tanaka et al. | |
| 2002/0183645 A1 | 12/2002 | Nachaliel | |
| 2002/0188197 A1 | 12/2002 | Bishop et al. | |
| 2002/0198738 A1 | 12/2002 | Osborne | |
| 2003/0001098 A1 | 1/2003 | Stoddart et al. | |
| 2003/0001837 A1 | 1/2003 | Baumberg | |
| 2003/0006376 A1 | 1/2003 | Tumer | |
| 2003/0013950 A1 | 1/2003 | Rollo et al. | |
| 2003/0013966 A1 | 1/2003 | Barnes et al. | |
| 2003/0038240 A1 | 2/2003 | Weinberg | |
| 2003/0055685 A1 | 3/2003 | Cobb et al. | |
| 2003/0063787 A1 | 4/2003 | Natanzon et al. | |
| 2003/0071219 A1 | 4/2003 | Motomura et al. | |
| 2003/0081716 A1 | 5/2003 | Tumer | |
| 2003/0103898 A1 | 6/2003 | Carpenter, Jr. | |
| 2003/0135388 A1 | 7/2003 | Martucci et al. | |
| 2003/0136912 A1 | 7/2003 | Juni | |
| 2003/0144322 A1 * | 7/2003 | Kozikowski et al. | 514/317 |
| 2003/0147887 A1 | 8/2003 | Wang et al. | |
| 2003/0158481 A1 | 8/2003 | Stotzka et al. | |
| 2003/0183226 A1 | 10/2003 | Brand et al. | |
| 2003/0189174 A1 | 10/2003 | Tanaka et al. | |
| 2003/0191430 A1 | 10/2003 | D'Andrea et al. | |
| 2003/0202629 A1 | 10/2003 | Dunham et al. | |
| 2003/0208117 A1 | 11/2003 | Shwartz et al. | |
| 2003/0215122 A1 | 11/2003 | Tanaka | |
| 2003/0215124 A1 | 11/2003 | Li | |
| 2003/0216631 A1 | 11/2003 | Bloch et al. | |
| 2003/0219149 A1 | 11/2003 | Vailaya et al. | |
| 2004/0003001 A1 | 1/2004 | Shimura | |
| 2004/0010397 A1 | 1/2004 | Barbour et al. | |
| 2004/0015075 A1 | 1/2004 | Kimchy et al. | |
| 2004/0021065 A1 | 2/2004 | Weber | |
| 2004/0044282 A1 | 3/2004 | Mixon et al. | |
| 2004/0051368 A1 | 3/2004 | Caputo et al. | |
| 2004/0054248 A1 | 3/2004 | Kimchy et al. | |
| 2004/0054278 A1 | 3/2004 | Kimchy et al. | |
| 2004/0065838 A1 | 4/2004 | Tumer | |
| 2004/0075058 A1 | 4/2004 | Blevis et al. | |
| 2004/0081623 A1 | 4/2004 | Eriksen et al. | |
| 2004/0082918 A1 | 4/2004 | Evans et al. | |
| 2004/0084340 A1 | 5/2004 | Morelle et al. | |
| 2004/0086437 A1 | 5/2004 | Jackson et al. | |
| 2004/0101176 A1 | 5/2004 | Mendonca et al. | |
| 2004/0101177 A1 | 5/2004 | Zahlmann et al. | |
| 2004/0116807 A1 | 6/2004 | Amrami et al. | |
| 2004/0120557 A1 | 6/2004 | Sabol | |
| 2004/0122311 A1 | 6/2004 | Cosman | |
| 2004/0125918 A1 | 7/2004 | Shanmugaval et al. | |
| 2004/0138557 A1 | 7/2004 | Le et al. | |

(56) References Cited

U.S. PATENT DOCUMENTS

| | | |
|---|---|---|
| 2004/0143449 A1 | 7/2004 | Behrenbruch et al. |
| 2004/0144925 A1 | 7/2004 | Stoddart et al. |
| 2004/0153128 A1 | 8/2004 | Suresh et al. |
| 2004/0162492 A1 | 8/2004 | Kobayashi |
| 2004/0171924 A1 | 9/2004 | Mire et al. |
| 2004/0183022 A1 | 9/2004 | Weinberg |
| 2004/0184644 A1 | 9/2004 | Leichter et al. |
| 2004/0193453 A1 | 9/2004 | Butterfield et al. |
| 2004/0195512 A1 | 10/2004 | Crosetto |
| 2004/0204646 A1 | 10/2004 | Nagler et al. |
| 2004/0205343 A1 | 10/2004 | Forth et al. |
| 2004/0210126 A1 | 10/2004 | Hajaj et al. |
| 2004/0238743 A1 | 12/2004 | Gravrand et al. |
| 2004/0251419 A1 | 12/2004 | Nelson et al. |
| 2004/0253177 A1 | 12/2004 | Elmaleh et al. |
| 2005/0001170 A1 | 1/2005 | Juni |
| 2005/0006589 A1 | 1/2005 | Young et al. |
| 2005/0020898 A1 | 1/2005 | Vosniak et al. |
| 2005/0020915 A1 | 1/2005 | Belardinelli et al. |
| 2005/0023474 A1 | 2/2005 | Persyk et al. |
| 2005/0029277 A1 | 2/2005 | Tachibana |
| 2005/0033157 A1 | 2/2005 | Klein et al. |
| 2005/0049487 A1 | 3/2005 | Johnson et al. |
| 2005/0055174 A1 | 3/2005 | David et al. |
| 2005/0056788 A1 | 3/2005 | Juni |
| 2005/0074402 A1* | 4/2005 | Cagnolini et al. ............ 424/1.65 |
| 2005/0107698 A1 | 5/2005 | Powers et al. |
| 2005/0107914 A1 | 5/2005 | Engleson et al. |
| 2005/0108044 A1 | 5/2005 | Koster |
| 2005/0113945 A1 | 5/2005 | Engleson et al. |
| 2005/0121505 A1 | 6/2005 | Metz et al. |
| 2005/0131270 A1 | 6/2005 | Weil et al. |
| 2005/0145797 A1 | 7/2005 | Oaknin et al. |
| 2005/0148869 A1 | 7/2005 | Masuda |
| 2005/0149350 A1 | 7/2005 | Kerr et al. |
| 2005/0156115 A1 | 7/2005 | Kobayashi et al. |
| 2005/0173643 A1 | 8/2005 | Turner |
| 2005/0187465 A1 | 8/2005 | Motomura et al. |
| 2005/0198800 A1 | 9/2005 | Reich |
| 2005/0203389 A1 | 9/2005 | Williams |
| 2005/0205792 A1 | 9/2005 | Rousso et al. |
| 2005/0205796 A1 | 9/2005 | Bryman |
| 2005/0207526 A1 | 9/2005 | Altman |
| 2005/0211909 A1 | 9/2005 | Smith |
| 2005/0215889 A1 | 9/2005 | Pattersonl, II |
| 2005/0234424 A1 | 10/2005 | Besing et al. |
| 2005/0247893 A1 | 11/2005 | Fu et al. |
| 2005/0253073 A1 | 11/2005 | Joram et al. |
| 2005/0261936 A1 | 11/2005 | Silverbrook et al. |
| 2005/0261937 A1 | 11/2005 | Silverbrook et al. |
| 2005/0261938 A1 | 11/2005 | Silverbrook et al. |
| 2005/0266074 A1 | 12/2005 | Zilberstein et al. |
| 2005/0277833 A1 | 12/2005 | Williams, Jr. |
| 2005/0277911 A1 | 12/2005 | Stewart et al. |
| 2005/0278066 A1 | 12/2005 | Graves et al. |
| 2005/0288869 A1 | 12/2005 | Kroll et al. |
| 2006/0000983 A1 | 1/2006 | Charron et al. |
| 2006/0033028 A1 | 2/2006 | Juni |
| 2006/0036157 A1 | 2/2006 | Turner |
| 2006/0072799 A1 | 4/2006 | McLain |
| 2006/0074290 A1 | 4/2006 | Chen et al. |
| 2006/0109950 A1 | 5/2006 | Arenson et al. |
| 2006/0122503 A1 | 6/2006 | Burbank et al. |
| 2006/0145081 A1 | 7/2006 | Hawman |
| 2006/0160157 A1 | 7/2006 | Zuckerman |
| 2006/0237652 A1 | 10/2006 | Kimchy et al. |
| 2006/0257012 A1 | 11/2006 | Kaufman et al. |
| 2007/0116170 A1 | 5/2007 | De Man et al. |
| 2007/0133852 A1 | 6/2007 | Collins et al. |
| 2007/0156047 A1 | 7/2007 | Nagler et al. |
| 2007/0166227 A1 | 7/2007 | Liu et al. |
| 2007/0189436 A1 | 8/2007 | Goto et al. |
| 2007/0194241 A1 | 8/2007 | Rousso et al. |
| 2007/0265230 A1 | 11/2007 | Rousso et al. |
| 2008/0001090 A1 | 1/2008 | Ben-Haim et al. |
| 2008/0029704 A1 | 2/2008 | Hefetz et al. |
| 2008/0033291 A1 | 2/2008 | Rousso et al. |
| 2008/0036882 A1 | 2/2008 | Uemura et al. |
| 2008/0039721 A1 | 2/2008 | Shai et al. |
| 2008/0042067 A1 | 2/2008 | Rousso et al. |
| 2008/0128626 A1 | 6/2008 | Rousso et al. |
| 2008/0131362 A1 | 6/2008 | Rousso et al. |
| 2008/0137938 A1 | 6/2008 | Zahniser |
| 2008/0230702 A1 | 9/2008 | Rousso et al. |
| 2008/0230705 A1 | 9/2008 | Rousso et al. |
| 2008/0237482 A1 | 10/2008 | Shahar et al. |
| 2008/0260228 A1 | 10/2008 | Dichterman et al. |
| 2008/0260637 A1 | 10/2008 | Dickman |
| 2008/0277591 A1 | 11/2008 | Shahar et al. |
| 2009/0001273 A1 | 1/2009 | Hawman |
| 2009/0018412 A1 | 1/2009 | Schmitt |
| 2009/0078875 A1 | 3/2009 | Rousso et al. |
| 2009/0112086 A1 | 4/2009 | Melman |
| 2009/0152471 A1 | 6/2009 | Rousso et al. |
| 2009/0190807 A1 | 7/2009 | Rousso et al. |
| 2009/0201291 A1 | 8/2009 | Ziv et al. |
| 2009/0236532 A1 | 9/2009 | Frach et al. |
| 2009/0304582 A1 | 12/2009 | Rousso et al. |
| 2010/0006770 A1 | 1/2010 | Balakin |
| 2010/0021378 A1 | 1/2010 | Rousso et al. |
| 2010/0102242 A1 | 4/2010 | Burr et al. |
| 2010/0121184 A1 | 5/2010 | Dhawale et al. |
| 2010/0202664 A1 | 8/2010 | Busch et al. |
| 2010/0245354 A1 | 9/2010 | Rousso et al. |
| 2012/0106820 A1 | 5/2012 | Rousso et al. |
| 2012/0172699 A1 | 7/2012 | Nagler et al. |
| 2012/0248320 A1 | 10/2012 | Wangerin et al. |
| 2012/0326034 A1 | 12/2012 | Sachs et al. |

FOREIGN PATENT DOCUMENTS

| | | |
|---|---|---|
| DE | 19815362 | 10/1999 |
| EP | 0273257 | 7/1988 |
| EP | 0525954 | 2/1993 |
| EP | 0526970 | 2/1993 |
| EP | 0543626 | 5/1993 |
| EP | 0592093 | 4/1994 |
| EP | 0697193 | 2/1996 |
| EP | 0813692 | 12/1997 |
| EP | 0887661 | 12/1998 |
| EP | 1237013 | 9/2002 |
| GB | 2031142 | 4/1980 |
| JP | 59-141084 | 8/1984 |
| JP | 61-026879 | 2/1986 |
| JP | 01-324568 | 6/1986 |
| JP | 03-121549 | 5/1991 |
| JP | 04-151120 | 5/1992 |
| JP | 6-109848 | 4/1994 |
| JP | 07-059763 | 3/1995 |
| JP | 07-141523 | 6/1995 |
| JP | 08-292268 | 11/1996 |
| JP | 10-260258 | 9/1998 |
| JP | 11-072564 | 3/1999 |
| WO | WO 92/00402 | 1/1992 |
| WO | WO 98/16852 | 4/1998 |
| WO | WO 99/03003 | 1/1999 |
| WO | WO 99/30610 | 1/1999 |
| WO | WO 99/39650 | 8/1999 |
| WO | WO 00/10034 | 2/2000 |
| WO | WO 00/18294 | 4/2000 |
| WO | WO 00/22975 | 4/2000 |
| WO | 0025268 A2 | 5/2000 |
| WO | WO 00/31522 | 6/2000 |
| WO | WO 00/38197 | 6/2000 |
| WO | WO 01/89384 | 11/2001 |
| WO | WO 02/16965 | 2/2002 |
| WO | WO 02/058531 | 8/2002 |
| WO | WO 02/075357 | 9/2002 |
| WO | WO 03/073938 | 9/2003 |
| WO | WO 03/086170 | 10/2003 |
| WO | WO 2004/004787 | 1/2004 |
| WO | WO 2004/032151 | 4/2004 |
| WO | WO2004/042546 | 5/2004 |
| WO | WO 2004/113951 | 12/2004 |

(56) References Cited

FOREIGN PATENT DOCUMENTS

| | | |
|---|---|---|
| WO | WO 2005/002971 | 1/2005 |
| WO | WO 2005/059592 | 6/2005 |
| WO | WO 2005/059840 | 6/2005 |
| WO | WO 2005/067383 | 7/2005 |
| WO | WO 2005/104939 | 11/2005 |
| WO | WO 2005/118659 | 12/2005 |
| WO | WO 2005/119025 | 12/2005 |
| WO | WO 2006/042077 | 4/2006 |
| WO | WO 2006/051531 | 5/2006 |
| WO | WO 2006/054296 | 5/2006 |
| WO | WO 2006/075333 | 7/2006 |
| WO | WO 2006/129296 | 12/2006 |
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2008/075362 | 6/2008 |

OTHER PUBLICATIONS

An Office Action dated Feb. 18, 2011, which issued during the prosecution of Applicant's U.S. Appl. No. 11/932,872.

An Office Action dated Feb. 4, 2011, which issued during the prosecution of Applicant's U.S. Appl. No. 11/750,057.

Garcia EV et al, "Accuracy of dynamic SPECT acquisition for Tc-99m teboroxime myocardial perfusion imaging: preliminary results," American College of Cardiology 51st Annual Scientific Session, Atlanta, Georgia (Mar. 17-20, 2002).

Case JA et al., "Reducing impact of changing liver concentration in Tc-99m-teboroxime imaging using dynamic SPECT," Cardiovascular Imaging Technologies, Kansas City, MO and Emory University, Atlanta, GA, Annual Meeting of the Society of Nuclear Medicine, Los Angeles (2002).

Case JA et al., in "Myocardial kinetics of technetium-99m teboroxime: a new radiopharmaceutical for assessing myocardial perfusion" (2001).

An International Preliminary Report dated May 28, 2009, which issued during the prosecution of Applicant's PCT/IL07/01392.

An International Search Report dated Jul. 7, 2008, which issued during the prosecution of Applicant's PCTIL07/01392.

Chua T et al., in "Technetium-99m teboroxime regional myocardial washout in subjects with and without coronary artery disease," Am J Cardiol 72:728-734 (1993).

Chua T et al., in "Rapid back to back adenosine stress/rest technetium-99m teboroxime myocardial perfusion SPECT using a triple-detector camera," J Nucl Med 34:1485-1493 (1993).

Feng B et al., in "Simultaneous assessment of cardiac perfusion and function using 5-dimensional imaging with Tc-99m teboroxime," J Nucl Cardiol 13(3): 354-61 (2006)—an abstract.

A. Celler, et al., "Investigation of the dynamic SPECT (dSPECT) method for teboroxime using a 4-D kinetic thorax model dMCAT", 2001.

WA Gray, et al., "Comparison of 99m Tc-teboroxime with thallium for myocardial Imaging in the presence of a coronary artery stenosis", American Heart association, Aug. 2006.

Case et al. [2001]). Stewart Re et al., in "Myocardial clearance kinetics of technetium-99m-SQ30217: a marker of regional myocardial blood flow," J Nucl Med 31:1183-1190 (1990).

Sitek A et al., in "Removal of liver activity contamination in teboroxime dynamic cardiac SPECT imaging with the use of factor analysis," J Nucl Cardiol 9(2): 197-205 (2002).

"CARDIOTEC® Kit for the Preparation of Technetium Tc 99m Teboroxime for Diagnostic Use" package insert, Bracco Diagnostics (Jul. 2003).

Bontemps L et al., "Technetium-99m teboroxime scintigraphy. Clinical experience in patients referred for myocardial perfusion evaluation," Eur J Nucl Med 18(9):732-9 (1991)—an abstract.

Chiao PC et al., "Compartmental analysis of technetium 99m-teboroxime kinetics employing fast dynamic SPECT at stress and rest," J Nucl Med 35:1265-73 (1994).

Meerdink DJ et al., "Experimental studies of the physiologic properties of technetium-99m agents: myocardial transport of perfusion imaging agents," Am J Cardiol 66:9E-15E (1990).

Leppo JA et al., "Comparative myocardial extraction of two technetium-labeled BATO derivatives (SQ30217, SQ32014) and thallium," J Nucl Med 31:67-74 (1990).

Narra RK et al., "A neutral technetium-99m complex for myocardial imaging," J Nucl Med 30:1830-1837 (1989).

Reutter BW et al., "Effects of temporal modelling on the statistical uncertainty of spatiotemporal distributions estimated directly from dynamic SPECT projections," Phys Med Biol 47(15):2673-83 (2002)—an abstract.

El Fakhri G et al., "Quantitative dynamic cardiac $82R_D$ PET using generalized factor and compartment analyses," J Nucl Med 46: 1264-1271 (2005).

Van Den Bossche B et al., "Receptor Imaging in Oncology by Means of Nuclear Medicine: Current Status," Journal of Clinical Oncology 22(17):3593-3607 (2004)—an abstract.

Dilsizian V et al., "Metabolic imaging with beta-methyl-p-[(123)I]-iodophenyl-pentadecanoic acid identifies ischemic memory after demand ischemia," Circulation 112(14):2169-74 (2005) Epub Sep. 26, 2005.

Gullberg GT et al., "Chapter 8: Dynamic Cardiac Single-Photon Emission Computed Tomography Using Fast Data Acquisition Systems," in Zaret BL et al., Clinical Nuclear Cardiology: State of the Art and Future Directions (Elsevier Mosby, 3rd edition, 2004).

Reutter BW et al., "Accuracy and precision of compartmental model parameters obtained from directly estimated dynamic SPECT time-activity curves," 2002 IEEE Nuclear Science Symposium and Medical Imaging Conference Records, pp. 1584-1588.

Sitek A et al., "Correction for ambiguous solutions in factor analysis using a penalized least squares objective," IEEE Trans Med Imaging 21(3):216-25 (2002)—an abstract.

Yang DJ et al., "Imaging with 99mTc ECDG targeted at the multifunctional glucose transport system: feasibility study with rodents," Radiology 226:465-473 (2003).

Rao PS et al., "99mTc-peptide-peptide nucleic acid probes for imaging oncogene mRNAs in tumours," Nuclear Medicine Communications 24(8):857-863 (2003)—an abstract.

Fischman AJ et al., "Infection imaging with technetium-99m-labeled chemotactic peptide analogs," Semin Nucl Med 24(2): 154-68 (1994)—an abstract.

Massoud TF et al., "Molecular imaging in living subjects: seeing fundamental biological processes in a new light," Genes & Development 17:545-580 (2003).

Gambhir SS, "Molecular imaging of cancer with positron emission tomography," Nature Reviews 2:683-693 (2002)—an abstract.

Yao D et al., "The utility of monoclonal antibodies in the imaging of prostate cancer," Semin Urol Oncol 20(3):211-8 (2002)—an abstract.

Van der Laken CJ et al., "Technetium-99m-labeled chemotactic peptides in acute infection and sterile inflammation," J Nucl Med 38(8):1310-5 (1997).

Babich JW et al., "Localization of radiolabeled chemotactic peptide at focal sites of *Escherichia coli* infection in rabbits: evidence for a receptor-specific mechanism," J Nucl Med 38(8): 1316-22 (1997).

An International Search Report dated Jul. 11, 2008, which issued during the prosecution of Applicant's PCT/IL06/01511.

An International Search Report dated Jul. 25, 2008, which issued during the prosecution of Applicant's PCT/IL07/001588.

An Office Action dated Sep. 4, 2008, which issued during the prosecution of Applicant's U.S. Appl. No. 10/533,568.

An Office Action dated Oct. 7, 2008, which issued during the prosecution of Applicant's U.S. Appl. No. 10/616,301.

An Office Action dated Jul. 12, 2007, which issued during the prosecution of Applicant's U.S. Appl. No. 10/616,301.

An Office Action dated Dec. 13, 2007, which issued during the prosecution of Applicant's U.S. Appl. No. 10/616,301.

An Office Action dated Jul. 15, 2008, which issued during the prosecution of Applicant's U.S. Appl. No. 09/641,973.

An Office Action dated Mar. 21, 2008, which issued during the prosecution of Applicant's U.S. Appl. No. 10/533,568.

(56) References Cited

OTHER PUBLICATIONS

An Office Action dated Jun. 25, 2008, which issued during the prosecution of Applicant's U.S. Appl. No. 10/616,301.
An Office Action dated Sep. 25, 2006, which issued during the prosecution of Applicant's U.S. Appl. No. 10/616,301.
An Office Action dated Sep. 30, 2008, which issued during the prosecution of Applicant's U.S. Appl. No. 10/616,301.
Supplementary Partial European Search Report dated Nov. 11, 2008, which issued during the prosecution of Applicant's European Patent Application No. 01951883.6.
Written Opinion dated Jul. 3, 2006 from the International Searching Authority of the Patent Cooperation Treaty Re: Application No. PCT/IL05/001173.
Gugnin, et al., "Radiocapsule for recording the Ionizing radiation in the gastrointestinal tract", UDC 615.417:616.34-005.1-073.916-71. (All-Union Scientific-ResearchInstitute of medical instrument design, Moscow, 1972).
Stoddart, et al., "New multi-dimensional reconstructions for the 12-detector, scanned focal point, single-photon tomography", Physics in medicine and biology, XP020021960, 37(3): 579-586, Mar. 1992.
Aoi, et al., "Absolute quantitation of regional myocardial blood flow of rats using dynamic pinhole SPECT", IEEE Nuclear Science Symposium and Medical Imaging Conf. 3:1780-1783, 2002. Abstract, Figs.
Corstens, et al., "Nuclear Medicine's Role in Infection and inflammation", The Lancet, 354:765-770, 1999.
Bromiley et al., "Attenuation correction in PET using consistency conditions and a three-dimensional template", IEEE Trans. on Nuclear Science, 48(4): 1371-1377, 2001.
Day, et al., "Localization of radioiodinated rat fibrogen in transplanted rat tumors", Journal of the National Cancer Institute, 23(4): 799-812, 1959.
Erbil, et al., "Use and limitations of serum total and lipid-bound sialic acid concentrations as markers for colorectal cancer", Cancer 55: 404-409, 1985.
Garcia et al., "Accuracy of dynamic SPECT acquisition for Tc-99m Teboroxime Myocardial Perfusion Imaging: Preliminary results", American College of Cardiology, 51$^{st}$ Annual Scientific Session, Atlanta, Georgia, USA, 8P, 2002.
Hassan, et al., "A Radiotelemetry Pill for the measurement of ionizing radiation using a mercuric iodide detector", Physics in medicine and biology, 23(2): 302-308, 1978.
Hayakawa, et al., "A PET-MRI Registration Technique for PET Studies of Rat Brain", Nuclear Medicine & Biology, 27:121-125, 2000. p. 121, col. 1.
Hoffman, et al., "Intraoperative Probes and Imaging Probes", European Journal of Nuclear Medicine, 26(8): 913-935, 1999.
Huesman, et al., "Kinetic parameter estimation from SPECT Cone-Beam Projection Measurement", Physics in Medicine and Biblogy, 43(4): 973-982, 1998.
Jeanguillaume, et al., "From the whole-body counting to imaging: The computer aided collimation gamma camera project (CACAO)", Radiation projection dosimetry 89(3-4): 349-352, 2000.
Jessup "Tumor markets—Prognostic and therapeutic implications for colorectal carcinoma", Surgical oncology, 7:139-151, 1998.
Kojima, et al., "Quantitative planar imaging method for measurement of renal activity by using a conjugate-emission image and transmission data", Medical Physics, 27(3): 608-615, 2000, p. 608.
Lavallee, et al., "Building a hybrid patient's model for augmented reality in surgery: A registration problem", Computing in Biological Medicine, 25(2): 149-164, 1995.
Molinolo, et al., "Enhanced tumor binding using immunohistochemical analyses by second generation anti-tumor-associated glycoprotein 72 monoclonal antibodies versus monoclonal antibody B72.3 in human tissue", Cancer Research, 50: 1291-1298, 1990.
Mori, et al., "Overexpression of Matrix metalloproteinase-7mRNA in human colon carcinomas", Cancer, 75: 1516-1519, 1995.
Pardridge, et al., "Tracer kinetic model of blood-brain barrier transport of plasma protein-bound ligands", Journal of Clinical Investigation, 74: 745-752, 1984.
Piperno, et al., "Breast cancer screening by impedance measurements", Frontiers Med. Biol. Engng. 2(2): 11-17, 1990.
Quartuccia, et al., "Computer assisted collimation gama camera: A new approach to imaging contaminated tissues", Radiation projection dosimentry, 89(3-4): 343-348, 2000.
Rajshekhar "Continuous Impedence Monitoring During CT-Guided Stereotactic Surgery: Relative Value in Cystic and Solid Lesions", British Journal of Neurosugery, 6:439-444, 1992.
Reutter, et al., "Direct Least Squares Estimation of Spatiotemporal Distributions from Dynamic SPECT Projections Using A Spatial Segmentation and Temporal B-Splines", IEEE Transactions on Medical Imaging, 19(5): 434-450, 2000.
Reutter, et al., "Kinetic parameter estimation from attenuated SPECT projection Measurements", IEEE Transactions on Nuclear Science, 45(6): 3007-3013, 1998.
Zhang, et al., "An innovative high efficiency and high resolution probe for prostate imaging", The journal of nuclear medicine, 68: 18, 2000, Abstract.
USPTO—Office Action dated May 12, 2011 issued in U.S. Appl. No. 11/747,378.
R.O. Dillman—Radiolabeled Anti-CD20 Monoclonal Antibodies for the Treatment of B-Cell Lymphoma, 2002, J. Clin Oncol. 20: 3545-3557.
T.F. Tedder, et al—Structure of the Gene Encoding the Human B-lymphocyte Differentiation Antigen CD20 (B1)—1989, J. Immunol. 142: 2560-2568.
Sands, et al—Methods for the Study of the Metabolism of Radiolabeled Monoclonal Antibodies by Liver and Tumor—1987, J. Nucl. Med. 28: 390-398.
Restriction Official Action Dated Aug. 16, 2012 From the US Patent and Trademark Office Re. U.S. Appl. No. 12/448,473.
Amendment After Allowance Under 37 CFR 1.312 Dated Sep. 13, 2010 to Notice of Allowance of Jul. 22, 2010 From the US Patent and Trademark Office Re.: U.S. Appl. No. 11/794,799.
Appeal Brief Dated Jan. 19, 2010 to Notice of Appeal of Nov. 16, 2009 From the US Patent and Trademark Office Re.: U.S. Appl. No. 10/616,301.
Communication Pursuant to Article 93(3) EPC Dated Mar. 8, 2010 From the European Patent Office Re.: Application No. 06832278.3.
Communication Pursuant to Article 94(3) EPC Dated Mar. 2, 2011 From the European Patent Office Re.: Application No. 06756259.5.
Communication Pursuant to Article 94(3) EPC Dated Mar. 8, 2010 From the European Patent Office Re.: Application No. 06832278.3.
Communication Pursuant to Article 94(3) EPC Dated Jun. 11, 2012 From the European Patent Office Re.: Application No. 06756259.5.
Communication Pursuant to Article 94(3) EPC Dated May 12, 2010 From the European Patent Office Re. Application No. 06809851.6.
Communication Pursuant to Article 94(3) EPC Dated May 12, 2010 From the European Patent Office Re.: Application No. 06809851.6.
Communication Pursuant to Article 94(3) EPC Dated Apr. 16, 2010 From the European Patent Office Re. Application No. 01951883.6.
Communication Pursuant to Article 94(3) EPC Dated Nov. 18, 2011 From the European Patent Office Re. Application No. 05803689.8.
Communication Pursuant to Article 94(3) EPC Dated Oct. 21, 2009 From the European Patent Office Re.: Application No. 02716285.8.
Communication Pursuant to Article 94(3) EPC Dated Jul. 22, 2009 From the European Patent Office Re.: Application No. 06809851.6.
Communication Pursuant to Article 94(3) EPC Dated Sep. 23, 2011 From the European Patent Office Re.: Application No. 06832278.3.
Communication Pursuant to Article 94(3) EPC Dated May 29, 2012 From the European Patent Office Re. Application No. 05803689.8.
Communication Pursuant to Article 96(2) EPC Dated Jun. 19, 2006 From the European Patent Office Re.: Application No. 03810570.6.
Communication Pursuant to Article 96(2) EPC Dated Aug. 30, 2007 From the European Patent Office Re.: Application No. 03810570.6.
Communication Pursuant to Rules 70(2) and 70a(2) EPC Dated Apr. 4, 2011 From the European Patent Office Re. Application No. 05803689.8.

(56) References Cited

OTHER PUBLICATIONS

Communication Relating to the Results of the Partial International Search Dated Apr. 18, 2007 From the International Searching Authority of the Patent Cooperation Treaty Re.: Application No. PCT/IL2006/001291.
Communication Relating to the Results of the Partial International Search Dated May 21, 2008 From the International Searching Authority of the Patent Cooperation Treaty Re.: Application No. PCT/IL2007/001588.
Communication Under Rule 71(3) EPC Dated May 30, 2012 From the European Patent Office Re.: Application No. 02716285.8.
Examination Report Dated Jun. 22, 2011 From the Government of India, Patent Office, intellectual Property Building Re. Application No. 2963/CHENP/2006.
international Preliminary Report on Patentability Dated Apr. 7, 2009 From the International Bureau of WIPO Re. Application No. PCT/IL2007/000918.
International Preliminary Report on Patentability Dated Jan. 13, 2009 From the International Bureau of WIPO Re. Application No. PCT/IL2006/000834.
International Preliminary Report on Patentability Dated May 14, 2008 From the International Bureau of WIPO Re. Application No. PCT/IL2006/001291.
International Preliminary Report on Patentability Dated May 15, 2007 From the International Bureau of WIPO Re. Application No. PCT/IL2005/001173.
International Preliminary Report on Patentability Dated Apr. 16, 2009 From the International Bureau of WIPO Re.: Applicaiton No. PCT/IL2007/000918.
International Preliminary Report on Patentability Dated Jun. 21, 2007 From the International Bureau of WIPO Re.: Application No. PCT/1L2005/000575.
International Preliminary Report on Patentability Dated Jan. 22, 2009 From the International Bureau of WIPO Re.: Application No. PCT/IL2006/000834.
International Preliminary Report on Patentability Dated Jan. 22, 2009 From the International Bureau of WIPO Re.: Application No. PCT/IL2006/001511.
International Preliminary Report on Patentability Dated May 22, 2007 From the International Preliminary Examining Authority Re.: Application No. PCT/IL06/00059.
International Preliminary Report on Patentability Dated May 22, 2008 From the International Bureau of WIPO Re.: Application No. PCT/IL2006/001291.
International Preliminary Report on Patentability Dated May 24, 2007 From the International Bureau of WIPO Re.: Application No. PCT/IL2005/001173.
International Preliminary Report on Patentability Dated Apr. 26, 2007 From the International Bureau of WIPO Re.: Application No. PCT/IL2005/000394.
International Preliminary Report on Patentability Dated Jan. 31, 2008 From the International Bureau of WIPO Re.: Application No. PCT/IL2006/000840.
International Search Report Dated Oct. 10, 2006 From the International Searching Authority of the Patent Cooperation Treaty Re.: Application No. PCT/IL06/00059.
International Search Report Dated Feb. 1, 2006 From the International Searching Authority of the Patent Cooperation Treaty Re.: Application No. PCT/IL05/00048.
international Search Report Dated Jul. 1, 2008 From the International Searching Authority of the Patent Cooperation Treaty Re.: Application No. PCT/IL06/00834.
International Search Report Dated Jul. 1, 2008 From the International Searching Authority Re. Application No. PCT/IL2006/000834.
International Search Report Dated Nov. 1, 2007 From the International Searching Authority of the Patent Cooperation Treaty Re.: Application No. PCT/IL06/00840.
International Search Report Dated Jul. 2, 2007 From the International Searching Authority of the Patent Cooperation Treaty Re.: Application No. PCT/IL2006/001291.
International Search Report Dated Jul. 2, 2007 From the International Searching Authority Re. Application No. PCT/IL2006/001291.
International Search Report Dated Aug. 3, 2006 From the International Searching Authority of the Patent Cooperation Treaty Re.: Application No. PCT/IL05/001173.
International Search Report Dated Aug. 3, 2006 From the International Searching Authority Re. Application No. PCT/IL2005/001173.
International Search Report Dated May 11, 2006 From the International Searching Authority of the Patent Cooperation Treaty Re.: Application No. PCT/IL05/001215.
International Search Report Dated Sep. 11, 2002 From the International Searching Authority of the Patent Cooperation Treaty Re.: Application No. PCT/IL01/00638.
International Search Report Dated Sep. 12, 2002 From the International Searching Authority of the Patent Cooperation Treaty Re: Application No. PCT/IL02/00057.
International Search Report Dated Oct. 15, 2008 From the International Searching Authority Re. Application No. PCT/2007/000918.
International Search Report Dated Oct. 15, 2008 From the International Searching Authority Re.: Application No. PCT/IL07/00918.
International Search Report Dated Mar. 18, 2004 From the International Searching Authority of the Patent Cooperation Treaty Re.: Application No. PCT/IL03/00917.
international Search Report Dated Mar. 23, 2006 From the International Searching Authority of the Patent Cooperation Treaty Re.: Application No. PCT/IL05/00572.
International Search Report Dated May 24, 2007 From the International Searching Authority of the Patent Cooperation Treaty Re.: Application No. PCT/IL05/00575.
International Search Report Dated Mar. 26, 2007 From the International Searching Authority of the Patent Cooperation Treaty Re.: Application No. PCT/IL05/00394.
Interview Summary Dated Mar. 25, 2011 From the US Patent and Trademark Office Re.: U.S. Appl. No. 10/836,223.
Interview Summary Dated May 31, 2011 From the US Patent and Trademark Office Re. U.S. Appl. No. 10/616,301.
Invitation to Pay Additional Fees Dated Jul. 10, 2008 From the International Searching Authority Re.: Application No. PCT/IL06/01511.
Invitation to Pay Additional Fees Dated Feb. 15, 2007 From the International Searching Authority Re.: Application No. PCT/IL05/00575.
Notice of Allowance Dated Feb. 2, 2012 From the US Patent and Trademark Office Re. U.S. Appl. No. 11/628,074.
Notice of Allowance Dated May 5, 2011 From the US Patent and Trademark Office Re.: U.S. Appl. No. 10/240,239.
Notice of Allowance Dated May 6, 2011 From the US Patent and Trademark Office Re. U.S. Appl. No. 11/980,617.
Notice of Allowance Dated Oct. 11, 2011 From the US Patent and Trademark Office Re. U.S. Appl. No. 11/988,926.
Notice of Allowance Dated Nov. 15, 2010 From the US Patent and Trademark Office Re. U.S. Appl. No. 10/616,301.
Notice of Allowance Dated Jul. 16, 2009 From the US Patent and Trademark Office Re.: U.S. Appl. No. 12/084,559.
Notice of Allowance Dated Sep. 16, 2011 From the US Patent and Trademark Office Re.: U.S. Appl. No. 11/607,075.
Notice of Allowance Dated Dec. 17, 2010 From the US Patent and Trademark Office Re. U.S. Appl. No. 11/980,617.
Notice of Allowance Dated Sep. 17, 2009 From the US Patent and Trademark Office Re.: U.S. Appl. No. 10/533,568. Suppl. IDS VIII in 25855.
Notice of Allowance Dated Jul. 22, 2010 From the US Patent and Trademark Office Re.: U.S. Appl. No. 11/794,799.
Notice of Allowance Dated Feb. 23, 2011 From the US Patent and Trademark Office Re.: U.S. Appl. No. 12/728,383.
Notice of Allowance Dated Jun. 23, 2011 From the US Patent and Trademark Office Re.: U.S. Appl. No. 10/616,301.
Notice of Allowance Dated Nov. 23, 2009 From the US Patent and Trademark Office Re.: U.S. Appl. No. 12/084,559.
Notice of Allowance Dated Aug. 25, 2010 From the US Patent and Trademark Office Re. U.S. Appl. No. 11/980,617.

(56) References Cited

OTHER PUBLICATIONS

Notice of Allowance Dated Jun. 30, 2010 From the United States Patent and Trademark Office Re.: U.S. Appl. No. 09/727,464.
Notice of Appeal and Pre-Appeal Brief Dated Jan. 4, 2010 to Official Action of Sep. 2, 2009 From the US Patent and Trademark Office Re.: U.S. Appl. No. 10/343,792.
Notice of Appeal Dated Nov. 16, 2009 to Official Action of Jul. 15, 2009 From the US Patent and Trademark Office Re.: U.S. Appl. No. 10/616,301.
Notice of Non-Compliant Amendment Dated Feb. 14, 2011 From the US Patent and Trademark Office Re.: U.S. Appl. No. 10/616,307.
Notice of Panel Decision From Pre-Appeal Brief Review Dated Feb. 29, 2012 From the US Patent and Trademark Office Re.: U.S. Appl. No. 10/836,223.
Office Action Dated Dec. 2, 2007 From the Israeli Patent Office Re.: Application No. 158442.
Office Action Dated Jan. 2, 2006 From the Israeli Patent Office Re.: Application No. 154323.
Office Action Dated Sep. 4, 2007 From the Israeli Patent Office Re.: Application No. 157007.
Office Action Dated Jul. 17, 2007 From the Israeli Patent Office Re.: Application No. 154323 and Its Translation Into English.
Office Action Dated Jul. 17, 2007 From the Israeli Patent Office Re.: Application No. 154323.
Official Action Dated Jun. 1, 2006 From the US Patent and Trademark Office Re.: U.S. Appl. No. 10/686,536.
Official Action Dated Mar. 1, 2010 From the US Patent and Trademark Office Re.: U.S. Appl. No. 11/794,799.
Official Action Dated Mar. 1, 2012 From the US Patent and Trademark Office Re.: U.S. Appl. No. 10/616,307.
Official Action Dated Nov. 1, 2010 From the US Patent and Trademark Office Re. U.S. Appl. No. 12/728,383.
Official Action Dated Nov. 1, 2010 From the US Patent and Trademark Office Re.: U.S. Appl. No. 12/728,383.
Official Action Dated Sep. 1, 2009 From the US Patent and Trademark Office Re.: U.S. Appl. No. 11/794,799.
Official Action Dated Jul. 2, 2004 From the US Patent and Trademark Office Re.: U.S. Appl. No. 09/641,973.
Official Action Dated Mar. 2, 2010 From the US Patent and Trademark Office Re. U.S. Appl. No. 11/980,617.
Official Action Dated Mar. 2, 2010 From the US Patent and Trademark Office Re.: U.S. Appl. No. 10/836,223.
Official Action Dated Mar. 2, 2010 From the US Patent and Trademark Office Re.: U.S. Appl. No. 11/980,617.
Official Action Dated Sep. 2, 2009 From the US Patent and Trademark Office Re.: U.S. Appl. No. 10/343,792.
Official Action Dated Aug. 3, 2010 From the US Patent and Trademark Office Re.: U.S. Appl. No. 11/980,690.
Official Action Dated May 3, 2007 From the US Patent and Trademark Office Re.: U.S. Appl. No. 10/240,239.
Official Action Dated Sep. 5, 2002 From the US Patent and Trademark Office Re.: U.S. Appl. No. 12/084,559.
Official Action Dated Mar. 6, 2012 From the US Patent and Trademark Office Re. U.S. Appl. No. 12/792,856.
Official Action Dated Jan. 7, 2009 From the US Patent and Trademark Office Re.: U.S. Appl. No. 10/616,307.
Official Action Dated Jul. 7, 2009 From the US Patent and Trademark Office Re.: U.S. Appl. No. 10/533,568.
Official Action Dated Apr. 8, 2010 From the US Patent and Trademark Office Re.: U.S. Appl. No. 11/980,690.
Official Action Dated Dec. 8, 2009 From the US Patent and Trademark Office Re.: U.S. Appl. No. 11/132,320.
Official Action Dated Dec. 8, 2010 From the US Patent and Trademark Office Re. U.S. Appl. No. 11/980,690.
Official Action Dated Dec. 8, 2010 From the US Patent and Trademark Office Re.: U.S. Appl. No. 09/641,973.
Official Action Dated Dec. 8, 2010 From the US Patent and Trademark Office Re.: U.S. Appl. No. 11/980,690.
Official Action Dated Jan. 8, 2010 From the US Patent and Trademark Office Re.: U.S. Appl. No. 11/656,548.
Official Action Dated Apr. 9, 2010 From the US Patent and Trademark Office Re.: U.S. Appl. No. 11/798,017.
Official Action Dated Mar. 9, 2011 From the US Patent and Trademark Office Re.: U.S. Appl. No. 10/616,301.
Official Action Dated Aug. 10, 2007 From the US Patent and Trademark Office Re.: U.S. Appl. No. 10/836,223.
Official Action Dated Nov. 10, 2010 From the US Patent and Trademark Office Re.: U.S. Appl. No. 10/616,307.
Official Action Dated Nov. 10, 2010 From the US Patent and Trademark Office Re.: U.S. Appl. No. 10/836,223.
Official Action Dated Aug. 11, 2009 From the US Patent and Trademark Office Re.: U.S. Appl. No. 09/641,973.
Official Action Dated Jul. 11, 2011 From the US Patent and Trademark Office Re.: U.S. Appl. No. 11/980,683.
Official Action Dated Mar. 11, 2010 From the US Patent and Trademark Office Re.: U.S. Appl. No. 11/607,075.
Official Action Dated Jul. 12, 2011 From the US Patent and Trademark Office Re.: U.S. Appl. No. 09/641,973.
Official Action Dated Sep. 12, 2011 From the US Patent and Trademark Office Re. U.S. Appl. No. 12/087,150.
Official Action Dated Aug. 13, 2008 From the US Patent and Trademark Office Re. U.S. Appl. No. 11/769,826.
Official Action Dated May 13, 2009 From the US Patent and Trademark Office Re.: U.S. Appl. No. 11/798,017.
Official Action Dated Sep. 13, 2011 From the US Patent and Trademark Office Re. U.S. Appl. No. 11/976,852.
Official Action Dated May 14, 2009 From the US Patent and Trademark Office Re.: U.S. Appl. No. 11/656,548.
Official Action Dated Apr. 15, 2008 From the US Patent and Trademark Office Re.: U.S. Appl. No. 09/641,973.
Official Action Dated Dec. 15, 2006 From the US Patent and Trademark Office Re.: U.S. Appl. No. 10/616,301.
Official Action Dated Dec. 15, 2011 From the US Patent and Trademark Office Re.: U.S. Appl. No. 10/343,792.
Official Action Dated Feb. 15, 2008 From the US Patent and Trademark Office Re.: U.S. Appl. No. 10/343,792.
Official Action Dated Jul. 15, 2008 From the US Patent and Trademark Office Re.: U.S. Appl. No. 09/641,973.
Official Action Dated Mar. 15, 2004 From the US Patent and Trademark Office Re.: U.S. Appl. No. 09/765,316.
Official Action Dated Mar. 15, 2011 From the US Patent and Trademark Office Re.: U.S. Appl. No. 10/343,792.
Official Action Dated Sep. 15, 2009 From the US Patent and Trademark Office Re.: U.S. Appl. No. 10/616,307.
Official Action Dated Sep. 15, 2009 From the US Patent and Trademark Office Re.: U.S. Appl. No. 10/836,223.
Official Action Dated Apr. 16, 2012 From the US Patent and Trademark Office Re.: U.S. Appl. No. 10/836,223.
Official Action Dated Dec. 16, 2008 From the US Patent and Trademark Office Re.: U.S. Appl. No. 10/343,792.
Official Action Dated Feb. 16, 2012 From the US Patent and Trademark Office Re. U.S. Appl. No. 11/747,378.
Official Action Dated Sep. 16, 2009 From the US Patent and Trademark Office Re.: U.S. Appl. No. 09/727,464.
Official Action Dated Jan. 17, 2006 From the United States Patent and Trademark Office Re.: U.S. Appl. No. 11/034,007.
Official Action Dated May 18, 2012 From the US Patent and Trademark Office Re. U.S. Appl. No. 11/989,223.
Official Action Dated Jan. 19, 2012 From the US Patent and Trademark Office Re. U.S. Appl. No. 11/667,793.
Official Action Dated Jul. 19, 2010 From the US Patent and Trademark Office Re.: U.S. Appl. No. 11/607,075.
Official Action Dated Jul. 19, 2010 From the US Patent and Trademark Office Re.: U.S. Appl. No. 11/656,548.
Official Action Dated Mar. 19, 2010 From the US Patent and Trademark Office Re.: U.S. Appl. No. 10/240,239.
Official Action Dated Apr. 20, 2006 From the United States Patent and Trademark Office Re.: U.S. Appl. No. 10/240,239.
Official Action Dated Apr. 20, 2011 From the US Patent and Trademark Office Re. U.S. Appl. No. 11/798,017.
Official Action Dated Apr. 20, 2011 From the US Patent and Trademark Office Re.: U.S. Appl. No. 11/798,017.

(56) References Cited

OTHER PUBLICATIONS

Official Action Dated Dec. 20, 2011 From the US Patent and Trademark Office Re. U.S. Appl. No. 12/309,479.
Official Action Dated Jul. 20, 2009 From the US Patent and Trademark Office Re.: U.S. Appl. No. 11/980,617.
Official Action Dated Sep. 21, 2009 From the US Patent and Trademark Office Re. U.S. Appl. No. 11/798,017.
Official Action Dated Sep. 21, 2009 From the US Patent and Trademark Office Re.: U.S. Appl. No. 11/798,017.
Official Action Dated Dec. 23, 2008 From the US Patent and Trademark Office Re.: U.S. Appl. No. 09/727,464.
Official Action Dated Feb. 23, 2010 From the US Patent and Trademark Office Re.: U.S. Appl. No. 09/641,973.
Official Action Dated Jan. 23, 2012 From the US Patent and Trademark Office Re. U.S. Appl. No. 12/087,150.
Official Action Dated Jun. 23, 2006 From the United States Patent and Trademark Office Re.: U.S. Appl. No. 09/727,464.
Official Action Dated May 23, 2011 From the US Patent and Trademark Office Re. U.S. Appl. No. 11/667,793.
Official Action Dated May 23, 2011 From the US Patent and Trademark Office Re. U.S. Appl. No. 11/980,690.
Official Action Dated May 23, 2011 From the US Patent and Trademark Office Re.: U.S. Appl. No. 10/616,307.
Official Action Dated May 23, 2011 From the US Patent and Trademark Office Re.: U.S. Appl. No. 11/980,690.
Official Action Dated Nov. 23, 2010 From the US Patent and Trademark Office Re.: U.S. Appl. No. 11/656,548.
Official Action Dated Nov. 26, 2008 From the US Patent and Trademark Office Re.: U.S. Appl. No. 10/240,239.
Official Action Dated Oct. 26, 2011 From the US Patent and Trademark Office Re.: U.S. Appl. No. 10/836,223.
Official Action Dated Apr. 27, 2011 From the US Patent and Trademark Office Re.: U.S. Appl. No. 10/836,223.
Official Action Dated Jul. 27, 2010 From the US Patent and Trademark Office Re.: U.S. Appl. No. 10/616,307.
Official Action Dated Oct. 27, 2011 From the US Patent and Trademark Office Re.: U.S. Appl. No. 11/656,548.
Official Action Dated Apr. 28, 2010 From the US Patent and Trademark Office Re.: U.S. Appl. No. 10/616,301.
Official Action Dated Aug. 28, 2009 From the US Patent and Trademark Office Re.: U.S. Appl. No. 10/240,239.
Official Action Dated Dec. 28, 2010 From the US Patent and Trademark Office Re.: U.S. Appl. No. 11/607,075.
Official Action Dated Feb. 28, 2012 From the US Patent and Trademark Office Re.: U.S. Appl. No. 09/641,973.
Official Action Dated Jan. 28, 2011 From the US Patent and Trademark Office Re.: U.S. Appl. No. 09/641,973.
Official Action Dated Jun. 28, 2011 From the US Patent and Trademark Office Re. U.S. Appl. No. 11/628,074.
Official Action Dated Apr. 29, 2009 From the US Patent and Trademark Office Re.: U.S. Appl. No. 11/980,690.
Official Action Dated Oct. 30, 2009 From the US Patent and Trademark Office Re.: U.S. Appl. No. 11/980,690.
Official Action Dated Sep. 30, 2010 From the US Patent and Trademark Office Re. U.S. Appl. No. 11/798,017.
Official Action Dated Sep. 30, 2010 From the US Patent and Trademark Office Re.: U.S. Appl. No. 11/798,017.
Official Action Dated Jan. 31, 2011 From the US Patent and Trademark Office Re. U.S. Appl. No. 11/667,793.
Restriction Official Action Dated Mar. 9, 2012 From the US Patent and Trademark Office Re. U.S. Appl. No. 11/976,852.
Restriction Official Action Dated Sep. 12, 2011 From the US Patent and Trademark Office Re. U.S. Appl. No. 11/980,653.
Restriction Official Action Dated Apr. 13, 2012 From the US Patent and Trademark Office Re. U.S. Appl. No. 11/989,223.
Restriction Official Action Dated Nov. 15, 2011 From the US Patent and Trademark Office Re. U.S. Appl. No. 11/980,683.
Second International Search Report Dated Jun. 1, 2009 From the International Searching Authority Re.: Application No. PCT/IL07/00918.
Summons to Attend Oral Proceedings Pursuant to Rule 115(1) EPC Dated Jan. 16, 2009 From the European Patent Office Re.: Application No. 03810570.6.
Supplemental Notice of Allowability Dated Oct. 24, 2011 From the US Patent and Trademark Office Re.: U.S. Appl. No. 11/607,075.
Supplemental Response After Interview Dated Aug. 4, 2010 to Official Action of Mar. 2, 2010 From the US Patent and Trademark Office Re.: U.S. Appl. No. 11/980,617.
Supplemental Response Under 37 C.F.R. § 1.125 Dated Aug. 12, 2010 to Telephonic interview of Aug. 6, 2010 From the US Patent and Trademark Office Re. U.S. Appl. No. 11/980,617.
Supplementary European Search Report and the European Search Opinion Dated Mar. 16, 2011 From the European Patent Office Re. Application No. 05803689.8.
Supplementary European Search Report Dated Dec. 12, 2005 From the European Patent Office Re.: Application No. 03810570.6.
Supplementary Partial European Search Report and the European Search Opinion Dated Dec. 15, 2009 From the European Patent Office Re.: Application No. 06832278.3.
Supplementary Partial European Search Report and the European Search Opinion Dated Oct. 16, 2009 From the European Patent Office Re.: Application No. 06756259.5.
Supplementary Partial European Search Report Dated Sep. 4, 2007 From the European Patent Office Re.: Application No. 0 2716285.8.
Supplementary Partial European Search Report Dated Nov. 20, 2007 From the European Patent Office Re.: Application No. 02716285.8.
Translation of Office Action Dated May 13, 2005 From the Patent Office of the People's Republic of China Re.: Application No. 01817689.5.
Written Opinion Dated Feb. 1, 2006 From the International Searching Authority of the Patent Cooperation Treaty Re.: Application No. PCT/IL05/00048.
Written Opinion Dated Jul. 1, 2008 From the International Searching Authority of the Patent Cooperation Treaty Re.: Application No. PCT/IL06/00834.
Written Opinion Dated Nov. 1, 2007 from the International Searching Authority of the Patent Cooperation Treaty Re.: Application No. PCT/IL06/00840.
Written Opinion Dated Jul. 2, 2007 From the International Searching Authority of the Patent Cooperation Treaty Re.: Application No. PCT/IL2006/001291.
Written Opinion Dated Oct. 10, 2006 From the International Searching Authority of the Patent Cooperation Treaty Re.: Application No. PCT/IL06/00059.
Written Opinion Dated Jul. 11, 2008 from the International Searching Authority of the Patent Cooperation Treaty Re.: Application No. PCT/IL06/01511.
Written Opinion Dated Oct. 15, 2008 From the International Searching Authority Re.: Application No. PCT/IL07/00918.
Written Opinion Dated Mar. 23, 2006 From the International Searching Authority of the Patent Cooperation Treaty Re.: Application No. PCT/IL05/00572.
Written Opinion Dated May 24, 2007 From the International Searching Authority of the Patent Cooperation Treaty Re.: Application No. PCT/IL05/00575.
Written Opinion Dated Jul. 25, 2008 From the International Searching Authority of the Patent Cooperation Treaty Re.: Application No. PCT/IL05/001173.
Written Opinion Dated Mar. 26, 2007 From the International Searching Authority of the Patent Cooperation Treaty Re.: Application No. PCT/IL05/00394.
Beekman et al. "Efficient Fully 3-D Iterative SPECT Reconstruction With Monte Carlo-Based Scatter Compensation", IEEE Transactions on Medical Imaging, 21(8): 867-877, Aug. 2002.
Bloch et al. "Application of Computerized Tomography to Radiation Therapy and Surgical Planning", Proceedings of the IEEE, 71(3): 351-355, Mar. 1983.
Bracco Diagnostics "Techneplex®: Kit for the Preparation of Technetium Tc 99m Pentetate Injection. Diagnostic—for Intravenous Use", Bracco Diagnostics™, Product Sheet, 5 P., Jun. 1995.
Brown et al. "Method for Segmenting Chest CT Image Data Using An Anatomical Model: Preliminary Results", IEEE Transactions on Medical Imaging, 16(6): 828-839, Dec. 1997.

(56) References Cited

OTHER PUBLICATIONS

Chengazi et al. "Imaging Prostate Cancer With Technetium-99m-7E11-C5.3 (CYT-351)", Journal of Nuclear Medicine, 38: 675-682, 1997.
Del Guerra et al. "An Integrated PET-SPECT Small Animal Imager: Preliminary Results", Nuclear Science Symposium, IEEE Records, 1: 541-544, 1999.
Dewaraja et al. "Accurate Dosimetry in 131I Radionuclide Therapy Using Patient-Specific, 3-Dimensional Methods for SPECT Reconstruction and Basorbed Dose Calculation", The Journal of Nuclear Medicine, 46(5): 840-849, May 2005.
Dillman "Radiolabeled Anti-CD20 Monoclonal Antibodies for the Treatment of B-Cell Lymphoma", Journal of Clinical Oncology, 20(16): 3545-3557, Aug. 15, 2002.
GE Healthcare "Myoview™: Kit for the Preparation of Technetium Tc99m Tetrofosmin for Injection. Diagnostic Radiopharmaceutical. For Intravenous Use Only. Rx Only", GE Healthcare, Product Sheet, 4 P., Aug. 2006.
Gilland et al. "A 3D Model of Non-Uniform Attenuation and Detector Response for Efficient Iterative Reconstruction in SPECT", Physics in Medicine and Biology, XP002558623, 39(3): 547-561, Mar. 1994. p. 549-550, Section 2.3 'Active Voxel Reconstruction', p. 551, Lines 4-8.
Gilland et al. "Simultaneous Reconstruction and Motion Estimation for Gated Cardiac ECT", IEEE Transactions on Nuclear Science, XP011077797, 49(5): 2344-2349, Oct. 1, 2002. p. 2344, Section 'Introduction', First §.
Herrmann et al. "Mitochondrial Proteome: Altered Cytochtrome C Oxidase Subunit Levels in Prostate Cancer", Proteomics, XP002625778, 3(9): 1801-1810, Sep. 2003.
Jin et al. "Reconstruction of Cardiac-Gated Dynamic SPECT Images", IEEE International Conference on Image Processing 2005, ICIP 2005, Sep. 11-14, 2005, 3: 1-4, 2005.
Kadrmas et al. "Static Versus Dynamic Teboroxime Myocardial Perfusion SPECT in Canines", IEEE Transactions on Nuclear Science, 47(3): 1112-1117, Jun. 2000.
Kinahan et al. "Attenuation Correction for A Combined 3D PET/CT Scanner", Medical Physics, 25(10): 2046-2053, Oct. 1998.
Krieg et al. "Mitochondrial Proteome: Cancer-Altered Metabolism Associated With Cytochrome C Oxidase Subunit Level Variation", Proteomics, XP002625779, 4(9): 2789-2795, Sep. 2004.
Li et al. "A HOTLink/Networked PC Data Acquisition and Image Reconstruction System for A High Resolution Whole-Body PET With Respiratory or ECG-Gated Performance", IEEE Nuclear Sience Symposium and Medical Imaging Conference, Norfolk, VA, USA, Nov. 10-16, 2002, XP010663724, 2: 1135-1139, Nov. 10, 2002. p. 1137, First Col., End §.
Lin et al. "Improved Sensor Pills for Physiological Monitoring", NASA Technical Brief, JPL New Technology Report, NPO-20652, 25(2), 2000.
Mallinckrodt "Kit for the Preparation of Technetium Tc 99m Sestamibi Injection", Mallinckrodt Inc., Product Sheet, 2 P., Sep. 8, 2008.
Mallinckrodt "OctreoScan®: Kit for the Preparation of Indium In-111 Pentetreotide. Diagnostic—for intravenous Use. Rx Only", Mallinckrodt Inc., Product Sheet, 2 P., Oct. 25, 2006.
Mao et al. "Human Prostatic Carcinoma: An Electron Microscope Study", Cancer Research, XP002625777, 26(5): 955-973, May 1966.
McJilton et al. "Protein Kinase C? Interacts With Bax and Promotes Survival of Human Prostate Cancer Cells", Oncogene, 22; 7958-7968, 2003.
Mettler et al., "Essentials of Nuclear Medicine Imaging", WB Saunders, Chap. 14.
Mettler et al. "Legal Requirements and Radiation Safety", Essentials of Nuclear Medicine Imaging, 2nd Ed., Chap.13: 323-331, 1985.
Moore et al. "Quantitative Multi-Detector Emission Computerized Tomography Using Iterative Attenuation Compensation", Journal of Nuclear Medicine, XP002549083, 23(8): 706-714, Aug. 1982. Abstract, p. 707, Section 'The Multi-Detector Scanner', First §.
Ogawa et al. "Ultra High Resoultion Pinhole SPECT", IEEE Nuclear Science Symposium, 2: 1600-1604, 1998.
Pellegrini et al. "Design of Compact Pinhole SPECT System Based on Flat Panel PMT", IEEE Nuclear Science Symposium Conference Record, 3: 1828-1832, 2003.
Pharmalucence "Kit for the Preparation of Technetium Tc99m Sulfur Colloid Injection for Subcutaneous, Intraperitoneal, Intravenous, and Oral Use", Pharmalucence inc., Reference ID: 2977567, Prescribing information, 10 P., Jul. 2011.
Pluim et al. "Image Registration by Maximization of Combined Mutual Information and Gradient Information", IEEE Transactions on Medical Imaging, 19(8): 1-6, 2000.
Qi et al. "Resolution and Noise Properties of MAP Reconstruction for Fully 3-D PET", IEEE Transactions on Medical Imaging, XP002549082, 19(5): 493-506, May 2000. p. 493, col. 2, Lines 10-21, p. 495, col. 1, Last §.
Saltz et al. "Interim Report of Randomized Phase II Trial of Cetuximab/Bevacizumab/Irinotecan (CBI) Versus Cetuximab/Bevacizumab (CB) in Irinotecan-Refractory Colorectal Cancer", Gastrointestinal Cancer Symposium, Hollywood, FL, USA, Jan. 27-29, 2005, American Society of Clinical Oncology, Abstract 169b, 4P., 2005.
Sands et al. "Methods for the Study of the Metabolism of Radiolabeled Monoclonal Antibodies by Liver and Tumor",The Journal of Nuclear Medicine, 28: 390-398, 1987.
Storey et al. "Tc-99m Sestamibi Uptake in Metastatic Prostate Carcinoma", Clinical Nuclear Medicine, XP009145398, 25(2): 133-134, Feb. 2000.
Takahashi et al. "Attenuation Correction of Myocardial SPECT Images With X-Ray CT: Effects of Registration Errors Between X-Ray CT and SPECT", Annals of Nuclear Medicine, 16(6): 431-435, Sep. 2002.
Toennies et al. "Scatter Segmentation in Dynamic SPECT Images Using Principal Component Analysis", Progress in Biomedical Optics and Imaging, 4(23): 507-516, 2003.
Trikha et al. "Monoclonal Antibodies as Therapeutics in Oncology", Current Opinion in Biotechnology, 13: 609-614, 2002.
Volkow et al. "Imaging the Living Human Brain: Magnetic Resonance Imaging and Positron Emission Tomography", Proc. Natl. Acad. Sci. USA, 94: 2787-2788, Apr. 1997.
Wilson et al. "Non-Stationary Noise Characteristics for SPECT Images", Proceedings of the Nuclear Science Symposium and Medical Imaging Conference, Santa Fe, CA, USA, Nov. 2-9, 1991, XP010058168, p. 1736-1740, Nov. 2, 1991. p. 1736, col. 2, Lines 4-6.
Wu et al. "ECG-Gated Pinhole SPECT in Mice With Millimeter Spatial Resolution", IEEE Transactions on Nuclear Science, 47(3): 1218-1221, Jun. 2000.
Xu et al. "Quantitative Expression Profile of Androgen-Regulated Genes in Prostate Cancer Cells and Identification of Prostate-Specific Genes", International Journal of Cancer, 92: 322-328, 2001.
Yu et al. "Using Correlated CT Images in Compensation for Attenuation in PET Image Reconstruction", Proceedings of the SPIE, Applications of Optical Engineering: Proceedings of OE/Midwest '90, 1396: 56-58, 1991.
Zaidi et al. "Magenetic Resonance Imaging-Guided Attenuation and Scatter Corrections in Three-Dimensional Brain Positron Emission Tomography", Medical Physics, 30(5): 937-948, May 2003.
Zaidi et al. "MRI-Guided Attenuation Correction in 3D Brain PET", Neuroimage Human Brain Mapping 2002 Meeting, 16(2): Abstract 504, Jun. 2002.
Zanger et al. "Diode-Pumped CW all Solid-State Laser at 266nm", OSA Trends in Optics and Photonics, 26: 104-111, 1999, Optical Society of American.
Official Action Dated Aug. 31, 2012 From the US Patent and Trademark Office Re. U.S. Appl. No. 11/980,653.
Official Action Dated Jun. 21, 2012 From the US Patent and Trademark Office Re. U.S. Appl. No. 12/309,479.
Advisory Action Before the Filing of an Appeal Brief Dated Jul. 12, 2012 From the US Patent and Trademark Office Re. U.S. Appl. No. 11/667,793.
Official Action Dated Aug. 2, 2012 From the US Patent and Trademark Office Re. U.S. Appl. No. 12/087,150.

(56) References Cited

OTHER PUBLICATIONS

Official Action Dated May 18, 2012 From the US Patent and Trademark Office Re. U.S. Appl. No. 12/514,785.
Official Action Dated Apr. 19, 2012 From the US Patent and Trademark Office Re. U.S. Appl. No. 11/750,057.
Official Action Dated Apr. 23, 2012 From the US Patent and Trademark Office Re. U.S. Appl. No. 11/932,987.
Official Action Dated Jul. 30, 2012 From the US Patent and Trademark Office Re.: U.S. Appl. No. 11/980,683.
Bowsher et al. "Treatment of Compton Scattering in Maximum-Likelihood, Expectation-Maximization Reconstructions of SPECT Images", Journal of Nuclear Medicine, 32(6): 1285-1291, 1991.
Handrick et al. "Evaluation of Binning Strategies for Tissue Classification in Computed Tomography Images", Medical Imaging 2006: Image Processing, Proceedings of the SPIE, 6144: 1476-1486, 2006.
Thorndyke et al. "Reducing Respiratory Motion Artifacts in Positron Emission Tomography Through Retrospective Stacking", Medical Physics, 33(7): 2632-2641, Jul. 2006.
Links JM Ann Nucl Med Sci; 13: 107-120, Revised and accepted Jan. 22, 2000.
Berman et al. Nucl. Cardiol. 1994, 12(2), 261-270.
Degrado et al. J. Nucl Cardiol. 2000, 7, 686-700.
David R Gilland et al: "Long Focal Length, Asymmetric Fan Beam Collimation for Transmission Acquisition with a Triple Camera SPECT System crossref idref=fn1 typeref=fnote This work was supported by PHS grants CA33541 and HL52162 and DOE grant DE-FG02-96ER62150./crossref", IEEE Transcitions on Nuclear Science. IEEE Service Center, New York, NY, US, vol. 44, No. 3, Jun. 1, 1997 pp. 1191-1196, XP011087666, ISSN: 0018-9499, DOI:10.1109/23.596986.
Lisha Zhang et al: "Potential of a Compton camera for high performance scintimammography; Compton scintimammography", Physics in Medicine and Biology, Taylor and Francis Ltd. London, GB, vol. 49 No. 4, Feb. 21, 2004, pp. 617-638, XP020024019, ISBN: 0031-9155, DOI:10.1088/0031-9155/49/4/011.
Ellestad Mervyn H: "Stress testing: principles and practice (Fifth edition)", Jan. 1, 2003, p. 432, XP008143015, ISBN: 0-19-515928-4.
Meyers Art et al: "Age, perfusion test results and dipyridamole reaction", Radiologic Technology, Grune and Stratton, Orlando, FL, US, vol. 73 No. 5, May 1, 2002, pp. 409-414, XP008142909, ISSN: 0033-8397.
An Office Action dated Dec. 20, 2011, which issued during the prosecution of U.S. Appl. No. 12/309,479.
An Office Action dated Nov. 8, 2011, which issued during the prosecution of U.S. Appl. No. 12/309,479.
An Office Action dated Sep. 22, 2011, which issued during the prosecution of EP Patent Application No. 06756258.7.
An Office Action dated Feb. 4, 2011, which issued during the prosecution of U.S. Appl. No. 11/750,057.
An Office Action dated Oct. 7, 2011, which issued during the prosecution of U.S. Appl. No. 11/750,057.
An Office Action dated Feb. 18, 2011, which issued during the prosecution of U.S. Appl. No. 11/932,872.
An Office Action dated Oct. 7, 2011, which issued during the prosecution of U.S. Appl. No. 11/932,872.
An Office Action dated Feb. 17, 2011, which issued during the prosecution of U.S. Appl. No. 11/932,987.
Communication Pursuant to Article 94(3) EPC Dated Sep. 17, 2012 From the European Patent Office Re. Application No. 06832278.3.
Ouyang et al. "Incorporation of Correlated Structural Images in PET Image Reconstruction", IEEE Transactions of Medical Imaging, 13(4): 627-640, Dec. 1994.
Official Action Dated Oct. 11, 2012 From the US Patent and Trademark Office Re. U.S. Appl. No. 11/976,852.
Cancer Medicine "Radiolabeled Monoclonal Antibodies. Historical Perspective", Cancer Medicine, 5th Ed., Sec.16: Principles of Biotherapeutics, Chap.65: Monoclonal Serotherapy, 2000.
Lange et al. "EM Reconstruction Algorithms for Emission and Transmission Tomography", Journal of Computer Assisted Tomography, 8(2): 306-316, Apr. 1984.

Ohrvall et al. "Intraoperative Gamma Detection Reveals Abdominal EndocrineTumors More Efficiently Than Somatostatin Receptor Scintigraphy", 6th Conference on Radioimmunodetection and Radioimmunotherapy of Cancer, Cancer, 80: 2490-2494, 1997.
Rockmore et al. "A Maximum Likelihood Approach to Emission Image Reconstruction From Projections", IEEE Transactions on Nuclear Science, 23(4): 1428-1432, Aug. 1976.
Shepp et al. "Maximum Likelihood Reconstruction for Emission Tomography", IEEE Transactions on Medical Imaging, MI-1: 113-122, Oct. 1982.
Sitek et al. "Reconstruction of Dynamic Renal Tomographic Data Acquired by Slow Rotation", The Journal of Nuclear Medicine, 42(11): 1704-1712, Nov. 2001.
Solanki "The Use of Automation in Radiopharmacy", Hospital Pharmacist, 7(4): 94-98, Apr. 2000.
Weldon et al. "Quantification of Inflammatory Bowel Disease Activity Using Technetium-99m HMPAO Labelled Leucocyte Single Photon Emission Computerised Tomography (SPECT)", Gut, 36: 243-250, 1995.
Communication Pursuant to Article 94(3) EPC Dated Nov. 12, 2012 From the European Patent Office Re. Application No. 06756258.7.
Communication Pursuant to Article 94(3) EPC Dated Oct. 26, 2012 From the European Patent Office Re. Application No. 05803689.8.
Notice of Allowance Dated Nov. 15, 2012 From the US Patent and Trademark Office Re.: U.S. Appl. No. 11/980,683.
Official Action Dated Oct. 10, 2012 From the US Patent and Trademark Office Re. U.S. Appl. No. 11/798,017.
Official Action Dated Jul. 15, 2009 From the US Patent and Trademark Office Re.: U.S. Appl. No. 10/616,301.
Official Action Dated Nov. 30, 2012 From the US Patent and Trademark Office Re. U.S. Appl. No. 12/514,785.
Summons to Attend Oral Proceedings Pursuant to Rule 115(1) EPC Dated Nov. 29, 2012 From the European Patent Office Re. Application No. 06756259.5.
Supplementary European Search Report and the European Search Opinion Dated Nov. 13, 2012 From the European Patent Office Re. Application No. 06728347.3.
Written Opinion Dated Aug. 3, 2006 From the International Searching Authority of the Patent Cooperation Treaty Re.: Application No. PCT/IL05/001173.
Brzymialkiewicz et al. "Evaluation of Fully 3-D Emission Mammotomography With a Compact Cadmium Zinc Telluride Detector", IEEE Transactions on Medical Imaging, 24(7): 868-877, Jul. 2005.
Jan et al. "Preliminary Results From the AROPET", IEEE Nuclear Science Symposium Conference Record, Nov. 4-10, 2001, 3: 1607-1610, 2001.
Ohno et al. "Selection of Optimum Projection Angles in Three Dimensional Myocardial SPECT", IEEE Nuclear Science Symposium Conference Record 2001, 4: 2166-2169, 2001.
Seret et al. "Intrinsic Uniformity Requirements for Pinhole SPECT", Journal of Nuclear Medicine Technology, 34(1): 43-47, Mar. 2006.
Smither "High Resolution Medical Imaging System for 3-D Imaging of Radioactive Sources With 1 mm FWHM Spatial Resolution", Proceedings of the SPIE, Medical Imaging 2003: Physics of Medical Imaging, 5030: 1052-1060, Jun. 9, 2003.
Tornai et al. "A 3D Gantry Single Photon Emission Tomograph With Hemispherical Coverage for Dedicated Breast Imaging", Nuclear Instruments & Methods in Physics Research, Section A, 497: 157-167, 2003.
Notice of Allowance Dated Dec. 26, 2012 From the US Patent and Trademark Office Re.: U.S. Appl. No. 11/980,690.
Official Action Dated Dec. 19, 2012 From the US Patent and Trademark Office Re. U.S. Appl. No. 12/448,473.
Official Action Dated Dec. 28, 2012 From the US Patent and Trademark Office Re.: U.S. Appl. No. 10/343,792.
Charland et al. "The Use of Deconvolution and Total Least Squares in Recovering a Radiation Detector Line Spread Function", Medical Physics, 25(2): 152-160, Feb. 1998. Abstract Only!
Advisory Action Before the Filing of an Appeal Brief Dated Feb. 26, 2013 From the US Patent and Trademark Office Re. U.S. Appl. No. 12/514,785.
Applicant-Initiated Interview Summary Dated Jan. 28, 2013 From the US Patent and Trademark Office Re.: U.S. Appl. No. 11/798,017.

(56) References Cited

OTHER PUBLICATIONS

Communication Under Rule 71(3) EPC Dated Feb. 26, 2013 From the European Patent Office Re. Application No. 06756259.5.
Notice of Allowance Dated Mar. 7, 2013 From the US Patent and Trademark Office Re. U.S. Appl. No. 13/726,316.
Notice of Allowance Dated Feb. 25, 2013 From the US Patent and Trademark Office Re.: U.S. Appl. No. 09/641,973.
Official Action Dated Feb. 7, 2013 From the US Patent and Trademark Office Re. U.S. Appl. No. 11/980,653.
Official Action Dated Feb. 22, 2013 From the US Patent and Trademark Office Re.: U.S. Appl. No. 10/616,307.
Notice of Allowance Dated Jun. 14, 2013 From the US Patent and Trademark Office Re. U.S. Appl. No. 10/616,307.
Official Action Dated Jun. 12, 2013 From the US Patent and Trademark Office Re. U.S. Appl. No. 12/087,150.
Bacharach et al. "Attenuation Correction in Cardiac Positron Emission Tomography and Single-Photon Emission Computed Tomography", Journal of Nucelar Cardiology, 2(3): 246-255, 1995.
Uni Magdeburg "Attenuation Map", University of Magdeburg, Germany, Retrieved From the Internet, Archived on Jul. 31, 2002.
Zaidi et al. "Determination of the Attenuation Map in Emission Tomography", Journal of Nuclear Medicine, 44(2): 291-315, 2003.
Advisory Action Before the Filing of an Appeal Brief Dated Feb. 26, 2013 From the US Patent and Trademark Office Re. U.S. Appl. No. 11/989,223.
Offical Action Dated Nov. 30, 2012 From the US Patent and Trademark Office Re. U.S. Appl. No. 11/989,223.
Official Action Dated Aug. 5, 2013 From the US Patent and Trademark Office Re. U.S. Appl. No. 12/309,479.
Official Action Dated Aug. 14, 2013 From the US Patent and Trademark Office Re. U.S. Appl. No. 12/448,473.
Berman et al "D-SPECT: A Noval Camera for High Speed Quantitative Molecular Imaging: Inital Clinical Results", The Journal of Nuclear Medicine, 47(Suppl.1): 1313P, 2006.
Berman et al. "Myocardial Perfusion Imaging With Technetium—99m—Sestamibi: Comparative Anaylsis of Available Imaging Protocols", The Journal of Nuclear Medicine, 35: 681-688, 1994.
Borges-Neto et al. "Perfusion and Function at Rest and Treadmill Exercise Using Technetium—99m—Sestamibi: Comparison of One- and Two-Day Protocols in normal Volunteers", The Journal of Nuclear Medicine, 31(7): 1128-1132, Jul. 1990.
Kwok et al. "Feasability of Simultancous Dual-Isotype Myocardial Perfusion Acquisition Using a Lower Dose of Sestamibi", European Journal of Nuclear Medicine, 24(3): 281-285, Mar. 1997.
Patton et al. "D-SPECT: A New Solid State Camera for High Speed Molecular Imaging", The Journal of Nuclear Medicine, 47(Suppl.1): 189P, 2006.
Official Action Dated Sep. 5, 2013 From the US Patent and Trademark Office Re. U.S. Appl. No. 13/947,198.

\* cited by examiner

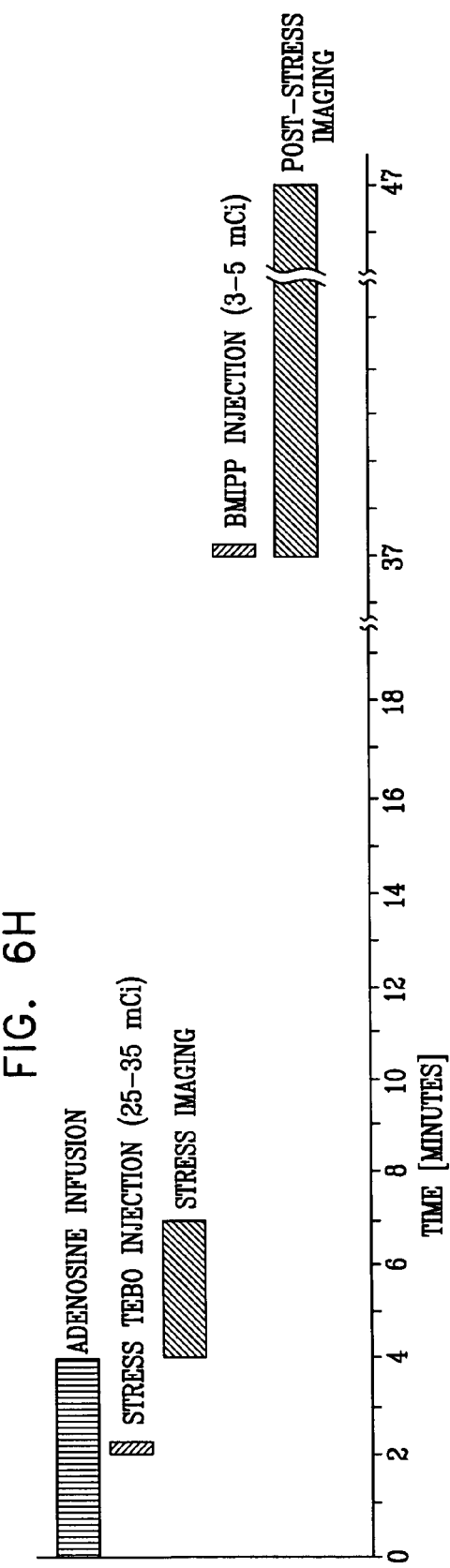
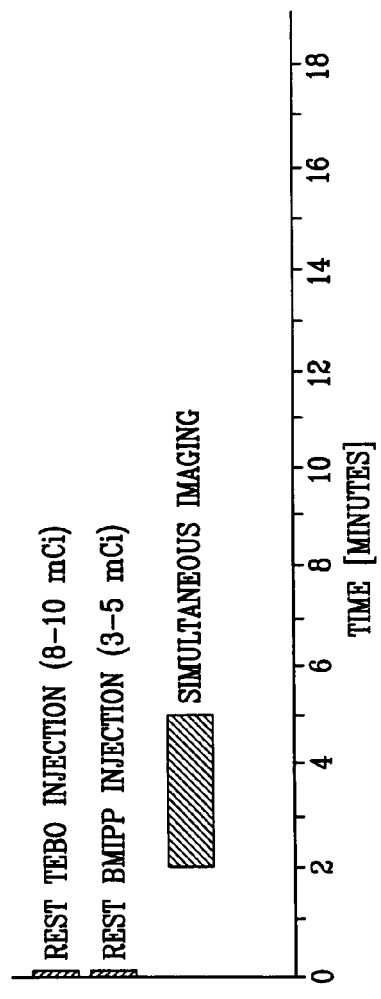
FIG. 6H
FIG. 6I

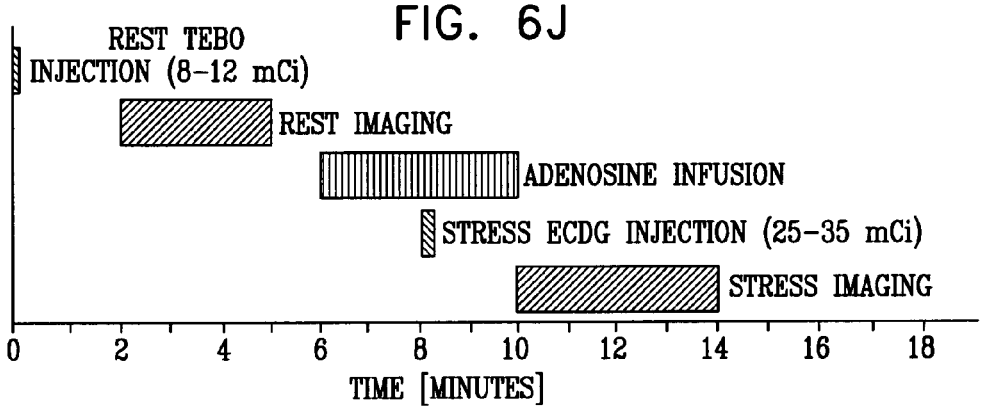
FIG. 6J
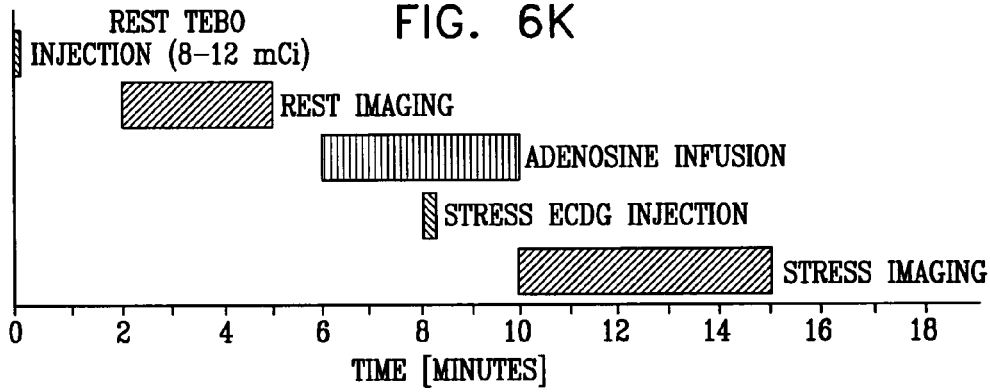
FIG. 6K
FIG. 6L
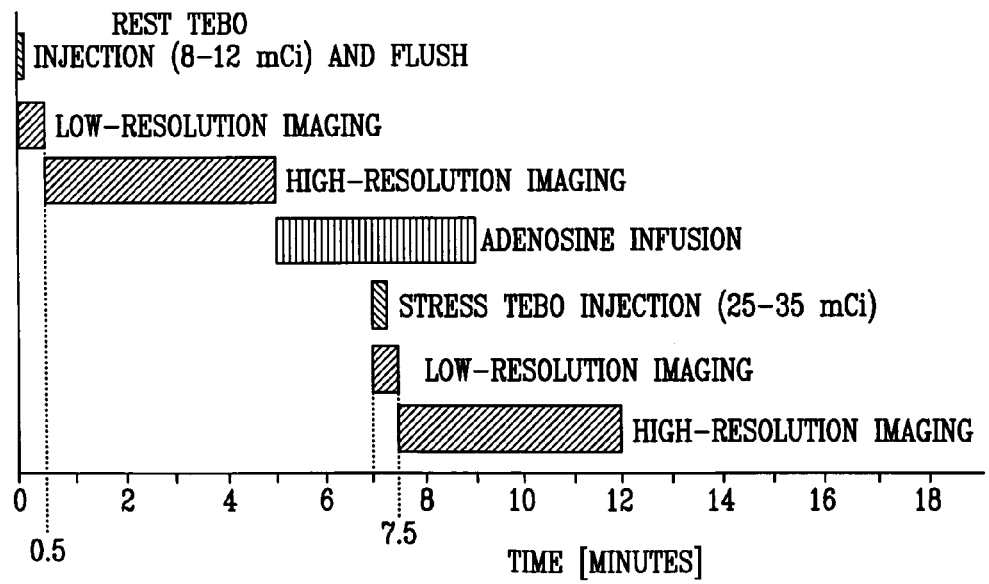

RADIOIMAGING APPLICATIONS OF AND NOVEL FORMULATIONS OF TEBOROXIME

CROSS-REFERENCES TO RELATED APPLICATIONS

The present patent application claims the benefit of U.S. Provisional Application 60/865,523, filed Nov. 13, 2006, entitled, "Radioimaging applications of and novel formulations of teboroxime," which is assigned to the assignee of the present application and is incorporated herein by reference.

The present patent application is related to:
(A) International Application PCT/IL2006/001291, filed Nov. 9, 2006;
(B) International Application PCT/IL2006/000834, filed Jul. 19, 2006;
(C) International Application PCT/IL2006/000840, filed Jul. 19, 2006; and
(D) International Application PCT/IL2006/000562, filed May 11, 2006, which is a continuation-in-part of:
(i) International Application PCT/IL2005/001215, filed Nov. 16, 2005;
(ii) International Application PCT/IL2006/000059, filed Jan. 15, 2006;
(iii) Israel Patent Application 171346, filed Oct. 10, 2005;
(iv) Israel Patent Application 172349, filed Nov. 27, 2005; and
(v) International Application PCT/IL2005/001173, filed Nov. 9, 2005, which:
(a) claims the benefit of the following US Provisional patent applications:
60/625,971, filed Nov. 9, 2004;
60/628,105, filed Nov. 17, 2004;
60/630,561, filed Nov. 26, 2004;
60/632,236, filed Dec. 2, 2004;
60/632,515, filed Dec. 3, 2004;
60/635,630, filed Dec. 14, 2004;
60/636,088, filed Dec. 16, 2004;
60/640,215, filed Jan. 3, 2005;
60/648,385, filed Feb. 1, 2005;
60/648,690, filed Feb. 2, 2005;
60/675,892, filed Apr. 29, 2005;
60/691,780, filed Jun. 20, 2005;
60/700,318, filed Jul. 19, 2005;
60/700,299, filed Jul. 19, 2005;
60/700,317, filed Jul. 19, 2005;
60/700,753, filed Jul. 20, 2005;
60/700,752, filed Jul. 20, 2005;
60/702,979, filed Jul. 28, 2005;
60/720,034, filed Sep. 26, 2005;
60/720,652, filed Sep. 27, 2005; and
60/720,541, filed Sep. 27, 2005, and
(b) is a continuation-in-part of the following International Patent Applications:
PCT/IL2005/000572, filed Jun. 1, 2005; and
PCT/IL2005/000575, filed Jun. 1, 2005.

International Application PCT/IL2006/000562 also claims the benefit of the following US Provisional Applications:
60/750,287, filed Dec. 13, 2005;
60/750,334, filed Dec. 15, 2005;
60/750,597, filed Dec. 15, 2005;
60/763,458, filed Jan. 31, 2006;
60/741,440, filed Dec. 2, 2005; and
60/750,294, filed Dec. 13, 2005.

The present application additionally is related to the following US Provisional applications:
60/800,845, filed May 17, 2006;
60/800,846, filed May 17, 2006;
60/799,688, filed May 11, 2006; and
60/816,970, filed Jun. 28, 2006.

All of the above-mentioned applications are assigned to the assignee of the present application and are incorporated herein by reference.

FIELD OF THE INVENTION

The present invention relates generally to radiological imaging techniques and radiopharmaceutical agents, and specifically to apparatus and methods for performing imaging procedures using teboroxime Tc-99m, and novel formulations of teboroxime Tc-99m.

BACKGROUND OF THE INVENTION

[Bis[1,2-cyclohexanedione dioxamato(1-)-O]-[1,2-cyclohexanedioneioximato(2-)-O]methylborato(2-)-N,N',N'',N''', N'''',N''''']-chlorotechnetium-99m (hereinbelow, "Tc-99m teboroxime" or just "teboroxime") is a radiopharmaceutical agent indicated for cardiac imaging, particularly for myocardial perfusion imaging to distinguish normal from abnormal myocardium in patients with suspected coronary artery disease (CAD) using rest and stress techniques. Teboroxime, which a member of a class of radiopharmaceuticals known as boronic acid adducts of technetium dioxime ("BATO" compounds), is a neutral, lipophilic agent labeled with technetium Tc-99m that is used for myocardial perfusion imaging (Narra [1989], all references cited hereinbelow). Teboroxime has the advantage of using Tc-99m (6 hours half-life and 140 keV photon energy) as the imaging radionuclide, while maintaining linear uptake with flow at high flow rates (Chiao [1994]). Its very high extraction (Leppo [1990]) potentially makes it an excellent perfusion agent for detecting mild to moderate severity coronary disease with high sensitivity and specificity. The rapid clearance characteristics of teboroxime potentially allows serial testing (rest, peak stress, and washout) in a contracted time frame, which also makes teboroxime valuable for use in clinical imaging.

Teboroxime is described in U.S. Pat. No. 4,705,849 to Nunn et al., which is incorporated herein by reference. Technetium-99m as a pertechnetate ion containing salt is combined with a source of anion, a boronic acid derivative having the formula

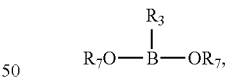

or a pharmaceutically acceptable salt thereof, wherein $R_7$ is hydrogen, alkyl or aryl, and a dioxime having the formula

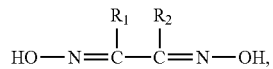

or a pharmaceutically acceptable salt thereof. The size of the host, and the imaging system used, are described as determining the quantity of radioactivity needed to produce diagnostic images. For a human host, the quantity of radioactivity injected normally ranges from about 5 to 20 millicuries (mCi) of technetium-99m.

U.S. Pat. No. 6,056,941 to Schramm et al., which is incorporated herein by reference, describes a kit for forming teboroxime in situ in the presence of hydroxypropyl gamma cyclodextrin to maintain the solution free of particulate matter originating from the formulation. The teboroxime formed has a radiation dose of 10 to 100 mCi.

Reference is made to FIG. 1, which is a graph from Case et al. (2001), cited hereinbelow, which shows the average teboroxime uptake as a function of time post-injection for the heart, liver, and background. One of the known drawbacks of teboroxime is that once it returns to the blood, it is readily taken up by the liver and other sub-diaphragmatic structures which potentially "obscure" the inferior wall of the heart. Thus, there is a short window of opportunity for imaging the post-injection perfusion pattern during which there is a peak heart to background ratio. Although teboroxime was approved for marketing by the U.S. Food and Drug Administration in 1991, it was subsequently discontinued by the manufacturer. Teboroxime "was not marketed because of limitations of hardware (nuclear cameras) and software of that era. Recently, Bracco Diagnostics, Inc. acquired the product and is planning to reintroduce it providing that an imaging protocol that capitalizes on its unique kinetics and software for processing, display and quantitation can be developed" (Case et al. [2001]).

Stewart R E et al., in "Myocardial clearance kinetics of technetium-99m-SQ30217: a marker of regional myocardial blood flow," J Nucl Med 31:1183-1190 (1990), which is incorporated herein by reference, describe a study that evaluated the myocardial tracer kinetics of technetium-99m-SQ30217 (teboroxime). The authors note that "Currently employed single- and dual-head tomography does not provide the necessary temporal resolution to delineate the kinetics of SQ30217 in the human heart. The newer multi-head SPECT systems may provide sufficient temporal resolution for the clinical application of $^{99m}$Tc-SQ30217 (18)" (p. 1189).

Chua T et al., in "Technetium-99m teboroxime regional myocardial washout in subjects with an without coronary artery disease," Am J Cardiol 72:728-734 (1993), which is incorporated herein by reference, describe a study designed "to test the hypothesis that regional myocardial washout of technetium-99m teboroxime is slowed in the presence of coronary stenosis" (abstract). Regional variability in washout rates were observed, "with the anterior and high lateral regions having the slowest washout, and the inferior wall the highest" (p. 732). "A possible explanation for this regional variation in washout rates is the effect of hepatic teboroxime uptake on the measured activity in the inferior wall. Liver uptake of teboroxime is avid, peaking 6 minutes after injection of teboroxime, and may interfere with visual assessment of the inferior wall" (p. 732).

Case T et al., in "Rapid back to back adenosine stress/rest technetium-99m teboroxime myocardial perfusion SPECT using a triple-detector camera," J Nucl Med 34:1485-1493 (1993), which is incorporated herein by reference, describe imaging parameters and the clinical efficacy of a rapid back to back adenosine stress/rest teboroxime myocardial perfusion SPECT protocol using a triple-detector camera. The authors note that "The rapid myocardial washout of teboroxime coupled with its intense late hepatic uptake necessitates that imaging be completed more quickly than with $^{201}$Tl or $^{99m}$Tc sestamibi" (p. 1485). The triple-headed camera used was able to produce "2-3 minute and 2-5 minute anterior view adenosine teboroxime (20-25 mCi) images containing 8,000-9,000 and 12,000-15,000 myocardial counts, respectively. The authors conclude, "Thus, despite the use of a triple-head detector camera and continuous acquisition, teboroxime studies with this fast protocol result in relatively low-count images" (p. 1490).

Feng B et al., in "Simultaneous assessment of cardiac perfusion and function using 5-dimensional imaging with Tc-99m teboroxime," J Nucl Cardiol 13(3):354-61 (2006), which is incorporated herein by reference, investigated the feasibility of simultaneously imaging myocardial ischemia and transient post-stress akinesis using gated-dynamic SPECT. A gated-dynamic mathematical cardiac torso (MCAT) phantom was developed to model both teboroxime kinetics and cardiac regional wall motion. A lesion was simulated as having delayed post-stress teboroxime washout together with a transient post-stress wall motion abnormality. Gated projection data were created to represent a 3-headed SPECT system undergoing a total rotation of 480 degrees. The dynamic expectation-maximization reconstruction algorithm with post-smoothing across gating intervals by Wiener filtering, and the ordered-subset expectation maximization reconstruction algorithm with 3-point smoothing across gating intervals were compared. Compared with the ordered-subset expectation maximization with 3-point smoothing, the dynamic expectation-maximization algorithm with Wiener filtering was able to produce visually higher-quality images and more accurate left ventricular ejection fraction estimates. The authors conclude that, from simulation, changing cardiac function and tracer localization possibly can be assessed by using a gated-dynamic acquisition protocol combined with a 5-dimensional reconstruction strategy.

Sitek A et al., in "Removal of liver activity contamination in teboroxime dynamic cardiac SPECT imaging with the use of factor analysis," J Nucl Cardiol 9(2):197-205 (2002), which is incorporated herein by reference, write, "One of the major problems associated with technetium 99m teboroxime cardiac imaging is the high concentration of activity in the liver. In some cases it is impossible to diagnose defects on the inferior wall because of the finite resolution and scatter that cause images of the inferior wall and the liver to overlap." The least-squares factor analysis of dynamic structures method, with correction for non-unique solutions, was used to remove the liver activity from the image. The method was applied to dynamically acquired Tc-99m teboroxime data. The liver activity removal method was tested through use of computer simulations and tomographically acquired canine and patient cardiac studies. The authors report that in all studies the least-squares factor analysis of dynamic structures method was able to extract the liver activity from the series of dynamic images, thereby making it possible to remove it quantitatively from the entire series. The method is described as being used successfully to remove the liver activity that partially overlapped the inferior wall in normal hearts. The method tends to increase the contrast between defects and normal myocardial tissue in abnormal hearts. The authors conclude that the method presented can be used to assist in diagnosis of cardiac disease when dynamically acquired teboroxime data are used. Because the contrast between the defect and normal myocardial tissue can be changed, the processed image cannot be used by itself to make an accurate diagnosis. However, with the liver activity removed, the image provides additional information that is described as being very useful in the imaging of patients whose liver activity overlaps the inferior heart wall.

The following references regarding teboroxime, all of which are incorporated herein by reference, may be of interest:

"CARDIOTEC® Kit for the Preparation of Technetium Tc 99m Teboroxime For Diagnostic Use" package insert, Bracco Diagnostics (July 2003)

Bontemps L et al., "Technetium-99m teboroxime scintigraphy. Clinical experience in patients referred for myocardial perfusion evaluation," Eur J Nucl Med 18(9):732-9 (1991)

Chua et al. in J Nucl Med in 1982

Chiao P C et al., "Compartmental analysis of technetium 99m-teboroxime kinetics employing fast dynamic SPECT at stress and rest," J Nucl Med 35:1265-73 (1994)

Meerdink D J et al., "Experimental studies of the physiologic properties of technetium-99m agents: myocardial transport of perfusion imaging agents," Am J Cardiol 66:9 E-15E (1990)

Leppo J A et al., "Comparative myocardial extraction of two technetium-labeled BATO derivatives (SQ30217, SQ32014) and thallium," J Nucl Med 31:67-74 (1990)

Narra R K et al., "A neutral technetium-99m complex for myocardial imaging," J Nucl Med 30:1830-1837 (1989)

Garcia E V et al, "Accuracy of dynamic SPECT acquisition for Tc-99m teboroxime myocardial perfusion imaging: preliminary results," American College of Cardiology 51st Annual Scientific Session, Atlanta, Ga. (Mar. 17-20, 2002)

Case J A et al., in "Myocardial kinetics of technetium-99m teboroxime: a new radiopharmaceutical for assessing myocardial perfusion" (2001)

Case J A et al., "Reducing impact of changing liver concentration in Tc-99m-teboroxime imaging using dynamic SPECT," Cardiovascular Imaging Technologies, Kansas City, Mo. and Emory University, Atlanta, Ga., Annual Meeting of the Society of Nuclear Medicine, Los Angeles (2002)

Reutter B W et al., "Effects of temporal modelling on the statistical uncertainty of spatiotemporal distributions estimated directly from dynamic SPECT projections," Phys Med Biol 47(15):2673-83 (2002)

Reutter B W et al., "Accuracy and precision of compartmental model parameters obtained from directly estimated dynamic SPECT time-activity curves," 2002 IEEE Nuclear Science Symposium and Medical Imaging Conference Records, pp. 1584-1588 (preprint) (2002)

Sitek A et al., "Correction for ambiguous solutions in factor analysis using a penalized least squares objective," IEEE Trans Med Imaging 21(3):216-25 (2002)

Yang D J et al., "Imaging with 99 mTc ECDG targeted at the multifunctional glucose transport system: feasibility study with rodents," Radiology 226:465-473 (2003)

El Fakhri G et al., "Quantitative dynamic cardiac $^{82}$Rb PET using generalized factor and compartment analyses," J Nucl Med 46:1264-1271 (2005)

Dilsizian V et al., "Metabolic imaging with beta-methyl-p-[(123)I]-iodophenyl-pentadecanoic acid identifies ischemic memory after demand ischemia," Circulation 112 (14):2169-74 (2005) Epub 2005 Sep. 26

Gullberg G T et al., "Chapter 8: Dynamic Cardiac Single-Photon Emission Computed Tomography Using Fast Data Acquisition Systems," in Zaret B L et al., *Clinical Nuclear Cardiology: State of the Art and Future Directions* (Elsevier Mosby, 3rd edition, 2004)

PCT Publication WO 06/051531 to Rousso et al., which is assigned to the assignee of the present application and is incorporated herein by reference, describes radioimaging methods, devices and radiopharmaceuticals. The publication describes several teboroxime preparation and imaging protocols.

U.S. Pat. No. 6,242,743 to DeVito et al., which is incorporated herein by reference, describes a tomographic imaging system which images ionizing radiation such as gamma rays or x-rays. The system is described as being capable of producing tomographic images without requiring an orbiting motion of the detector(s) or collimator(s) around the object of interest, and of observing the object of interest from sufficiently many directions to allow multiple time-sequenced tomographic images to be produced. The system consists of a plurality of detector modules which are distributed about or around the object of interest and which fully or partially encircle it. The detector modules are positioned close to the object of interest thereby improving spatial resolution and image quality. The plurality of detectors view a portion of the patient or object of interest simultaneously from a plurality of positions. These attributes are achieved by configuring small modular radiation detector with high-resolution collimators in a combination of application-specific acquisition geometries and non-orbital detector module motion sequences composed of tilting, swiveling and translating motions, and combinations of such motions. Various kinds of module geometry and module or collimator motion sequences are possible. The geometric configurations may be fixed or variable during the acquisition or between acquisition intervals.

The following patents and patent application publications, which describe gamma cameras and imaging processing techniques, and which are incorporated herein by reference, may be of interest:

US Patent Application Publication 2005/0205792 to Rousso et al.

PCT Publication WO 05/118659 to Dichterman et al.

PCT Publication WO 05/119025 to Nagler et al.

US Patent Application Publication 2004/0204646 to Nagler et al.

PCT Publication WO 06/054296 to Dickman

PCT Publication WO 06/051531 to Rousso et al.

PCT Publication WO 04/042546 to Kimchy et al.

US Patent Application Publication 2004/0054248 to Kimchy et al.

US Patent Application Publication 2004/0015075 to Kimchy et al.

US Patent Application Publication 2004/0054278 to Kimchy et al.

US Patent Application Publication 2005/0266074 to Zilberstein et al.

U.S. Pat. Nos. 5,939,724, 5,587,585, and 5,365,069 to Eisen et al.

U.S. Pat. No. 6,943,355 to Shwartz et al.

U.S. Pat. No. 5,757,006 to DeVito et al.

U.S. Pat. No. 6,137,109 to Hayes

U.S. Pat. No. 6,388,258 to Berlad et al.

U.S. Pat. No. 6,429,431 to Wilk

U.S. Pat. No. 6,838,672 to Wagenaar et al.

U.S. Pat. Nos. 6,740,882, 6,545,280, 6,229,145, 5,519, 221, 5,252,830, and 6,628,984 to Weinberg U.S. Pat. No. 6,713,766 to Garrard et al.

U.S. Pat. No. 6,765,981 to Heumann

U.S. Pat. No. 6,664,542 to Ye et al.

U.S. Pat. No. 6,080,984 to Friesenhahn

U.S. Pat. No. 5,818,050 to Dilmanian et al.

U.S. Pat. No. 6,728,583 to Hallett

U.S. Pat. No. 5,481,115 to Hsieh et al.

U.S. Pat. No. 6,723,988 to Wainer

U.S. Pat. No. 6,940,070 to Turner

U.S. Pat. No. 6,635,879 to limbo et al.

U.S. Pat. No. 6,353,227 to Boxen

U.S. Pat. No. 6,184,530 to Hines et al.

US Patent Application Publication 2005/0145797 to Oaknin et al.

US Patent Application Publication 2004/0251419 to Nelson et al.
US Patent Application Publication 2003/0001098 to Stoddart et al.
PCT Publication WO 98/16852 to DeVito et al.
PCT Publication WO 05/059840 to Nielsen et al.
U.S. Pat. No. 5,813,985 to Carroll The following articles, all of which are incorporated herein by reference, may be of interest:

Van Den Bossche B et al., "Receptor Imaging in Oncology by Means of Nuclear Medicine Current Status," Journal of Clinical Oncology 22(17):3593-3607 (2004)

Yao D et al., "The utility of monoclonal antibodies in the imaging of prostate cancer," Semin Urol Oncol 20(3):211-8 (2002)

van der Laken C J et al., "Technetium-99m-labeled chemotactic peptides in acute infection and sterile inflammation," J Nucl Med 38(8):1310-5 (1997)

Babich J W et al., "Localization of radiolabeled chemotactic peptide at focal sites of *Escherichia coli* infection in rabbits: evidence for a receptor-specific mechanism," J Nucl Med 38(8):1316-22 (1997)

Rao P S et al., "99 mTc-peptide-peptide nucleic acid probes for imaging oncogene mRNAs in tumours," Nuclear Medicine Communications 24(8):857-863 (2003)

Fischman A J et al., "Infection imaging with technetium-99m-labeled chemotactic peptide analogs," Semin Nucl Med 24(2):154-68 (1994)

Massoud T F et al., "Molecular imaging in living subjects: seeing fundamental biological processes in a new light," Genes & Development 17:545-580 (2003)

Gambhir S S, "Molecular imaging of cancer with positron emission tomography," Nature Reviews 2:683-693 (2002)

SUMMARY OF THE INVENTION

Embodiments of the present invention provide novel BATO-based, including teboroxime-based, kits and labeled radiopharmaceutical agents, imaging protocols, a SPECT imaging system for performing cardiac imaging, and an end-to-end automated system for enabling the protocols and imaging.

In some embodiments of the present invention, the SPECT imaging system produces a "clinically-valuable image," as defined hereinbelow, of a cardiac region of interest (ROI) upon administration of teboroxime at a dose of about 15 to about 50 mCi, such as about 15 to about 35 mCi. The inventors believe that conventional SPECT imaging systems have not been able to produce such clinically-valuable images, and that such failure was a primary reason why the manufacturer of teboroxime voluntarily withdrew the drug from the market in the United States, and has yet to reintroduce it despite development efforts to produce clinically-valuable images. Evidence is presented hereinbelow demonstrating that the imaging system of the present invention is capable of producing such clinically-valuable images. In summary, such evidence demonstrates that the SPECT imaging system of embodiments of the present invention is able to obtain at least 5 times the sensitivity of conventional SPECT imaging systems, such as at least 7 times or 10 times the sensitivity of conventional SPECT imaging systems. This greater sensitivity enables the generation of clinically-valuable images prior to contamination of the liver by the teboroxime, which occurs at about 5 minutes after injection.

In some embodiments of the present invention, the SPECT imaging system performs a complete teboroxime-based myocardial perfusion scan in between about 2 and about 3 minutes, which is quickly enough to capture the rapid kinetics of teboroxime prior to contamination by liver emissions. For some applications, the system performs dynamic imaging having a time resolution of as fast as 5 seconds per full scan of the heart. Such dynamic imaging enables the monitoring of the wash-in and washout kinetics of teboroxime. The dynamic data is analyzed using kinetic perfusion models specific to teboroxime to calculate myocardial blood flow and coronary flow reserve (CFR).

In some embodiments of the present invention, a kit for the preparation or a container containing a dose of a radiolabeled radiopharmaceutical agent comprises a boronic acid adduct of 99m-technetium dioxime (99m-BATO), such as teboroxime, having a radioactivity of less than 5 mCi, such as less than or equal to 4.5 mCi, less than or equal to 4 mCi, or less than or equal to 3 mCi, e.g., between about 2 and about 3 mCi. The SPECT imaging system is able to produce clinically-valuable images using this kit or dose. To the knowledge of the inventors, prior art teboroxime kits, either marketed or described in the patent and medical literature, contain at least 5 mCi technetium Tc-99, because it was not contemplated that lower doses could produce clinically-valuable images in adult human subjects.

In some embodiments of the present invention, ultra-fast rest/stress protocols are provided that use teboroxime for rest and/or stress imaging. Some of these protocols provide (a) a rest administration of teboroxime having a dose of between about 8 and about 12 mCi, and rest imaging having a duration of about 3 minutes, followed by (b) a stress administration of teboroxime having a dose of between about 20 and about 40 mCi, e.g., between about 25 and about 35 mCi, and stress imaging having a duration of about 4 minutes. Alternatively, the protocol substitutes thallium having a radioactivity of between about 3 and about 5 mCi, between about 1 and about 5 mCi, or less than about 1 mCi, for one of the rest or stress imaging.

In some embodiments of the present invention, the administration and image capture phases of the protocols described herein are performed in a single session while the patient remains continuously under the camera of the imaging system. The patient's remaining in place is generally more convenient and comfortable for the patient, and more efficient for the imaging facility. Many of the protocols described herein are performed with a total duration of less than 30 minutes, such as less than 20 minutes, or less than 15 minutes. Typically, although not necessarily, the protocols described herein are performed using a kit that provides the radiopharmaceutical agents and other agents, and using an integrated automated administration and imaging system, such as described herein.

In some embodiments of the present invention, protocols are provided that use teboroxime in combination with another radiopharmaceutical agent, such as I-123 BMIPP or Tc-99m ECDG. For some applications, these protocols include a dual-isotope teboroxime stress/I-123 BMIPP protocol, for a combined perfusion and fatty acid imaging study. This protocol provides stress imaging using teboroxime having a dose of between about 20 and about 40 mCi, e.g., between about 25 and about 35 mCi, followed by post-stress imaging using BMIPP having a dose of between about 3 and about 5 mCi. These protocols also include a dual-isotope simultaneous-imaging teboroxime rest/I-123 BMIPP protocol, for a combined perfusion and fatty acid imaging study. These protocols further include a dual-isotope teboroxime rest/Tc-99m ECDG stress protocol for a combined perfusion and glucose imaging study (either static or dynamic).

For other applications, these teboroxime combination protocols use teboroxime and another Tc-99m-based radiopharmaceutical agent, such as $^{99m}$Tc-sestamibi or $^{99m}$Tc-tetrofosmin. Such other Tc-99-m-based radiopharmaceutical agents typically remain longer in the heart than does teboroxime. Typically, these protocols comprise first administering teboroxime and performing imaging, followed by administering the other Tc-99m-based radiopharmaceutical agent and performing imaging. For some applications, the first administration is performed under stress (physical or pharmacological), and the second administration is performed at rest, while for other applications, the first administration is performed at rest, and the second administration is performed under stress.

Alternatively, these protocols comprise first administering the other Tc-99-m-based radiopharmaceutical agent, and beginning the imaging of the other agent. Before this imaging is completed, the teboroxime is administered and imaged, and the imaging continues until the teboroxime has substantially washed out of the heart, such that the other agent remains and imaging thereof is completed. The interference of the emissions from the other agent is estimated based on the detected levels of emission before administration of the teboroxime and after its wash-out, and these emissions are subtracted out of the counts obtained during the imaging of the teboroxime. For example, the other agent may comprise $^{99m}$Tc-sestamibi, which may be administered under stress, such as before the patient is positioned at the imaging system.

Further alternatively, the other Tc-99-m-based radiopharmaceutical agent is administered first, such as under stress, and subsequently the teboroxime is administered. Imaging of the teboroxime is performed first, and after the teboroxime has substantially washed out of the heart, imaging of the other agent is performed.

In some embodiments of the present invention, the kit comprises additional components, which are injected independently or together with other components of the kit, or, alternatively, are pre-mixed with at least one other component of the kit. For example, these other components may comprise: (a) saline for performing a "flush"; (b) BMIPP-I123 for imaging of fatty-acid metabolism; (c) F18-labeled FDG for imaging glucose metabolism; and/or (d) Tc-99m-labeled glucose (e.g., Tc-99m-2-deoxy-d-glucose) for imaging glucose metabolism. In some embodiments of the present invention, protocols described herein include administering and/or imaging at least one of these additional components, either separately from or simultaneously with other steps of the protocols.

In some embodiments of the present invention, a teboroxime protocol provides a dynamic study for performing blood flow measurements and calculation of coronary flow reserve (CFR). The protocol begins with an estimation of an input function, by sampling the myocardium in approximately 5-second intervals during a first, low-resolution rest phase having a duration of about 0.5 minutes. Once the tracer begins to diffuse into the myocardium, the sampling time of the myocardium is increased, typically to approximately 30-second intervals. The system analyzes these dynamic sequences using a compartmental analysis approach. Typically, this rest phase of the protocol is followed by a stress phase, in which the low- and high-resolution imaging are repeated.

In some embodiments of the present invention, the SPECT imaging system comprises a plurality of detector assemblies, each of which comprises a detector coupled to an angular orientator. Each of the detectors comprises a plurality of gamma ray sensors and at least one collimator. A control unit drives, typically separately, each of the orientators to orient its respective detector in a plurality of rotational orientations with respect to a region of interest (ROI) of a subject. The control unit produces an image, typically a SPECT image, from a plurality of radiation acquisitions acquired with the detectors in different relative orientations. For some applications, the imaging system utilizes techniques described in the above-mentioned PCT Publications WO 06/051531 and/or WO 05/119025, and/or in the other patent applications and/or patent application publications incorporated herein by reference.

The SPECT imaging system is generally at least 10 times more sensitive than conventional SPECT imaging systems, and thus enables the generation of clinically-valuable images using the techniques and protocols described herein.

In some embodiments of the present invention, an end-to-end automated system for medical imaging comprises a plurality of integrated elements that are configured to electronically exchange information among one another. In addition to the imaging system described hereinabove, the elements include an automated radiopharmaceutical dispensing system, a portable information-bearing radiopharmaceutical agent container, a portable patient-specific data carrier, and an automated administration system. Typically, a data carrier is physically coupled to container. The systems perform their respective automated functions at least in part responsively to the exchanged information. The elements typically authenticate one another via the exchanged information, in order to ensure that only authorized elements participate in the system, and that only authorized and appropriate functions are performed.

In some embodiments of the present invention, the automated radiopharmaceutical dispensing system comprises an information manager that is configured to receive radiopharmaceutical information regarding a labeled radiopharmaceutical agent and patient information regarding a patient. Responsively to the information, the dispensing system automatically dispenses a dose of the labeled radiopharmaceutical agent to an agent container, and stores the radiopharmaceutical information and at least a portion of the patient information in a data carrier associated with the container. For some applications, the radiopharmaceutical information is selected from the group consisting of: imaging protocol information for use with the labeled radiopharmaceutical agent, such as a SPECT imaging protocol; at least one kinetic parameter useful for performing a dynamic SPECT imaging procedure using the at least one labeled radiopharmaceutical agent; and authenticatable information regarding a commercial license for use of a SPECT imaging protocol with the at least one labeled radiopharmaceutical agent.

In some embodiments of the present invention, the dispensing system is configured to receive a mother vial containing a labeled radiopharmaceutical agent in a quantity sufficient for preparation of a plurality of doses of the labeled radiopharmaceutical agent. Associated with the mother vial is a data carrier containing information regarding the labeled radiopharmaceutical agent, such as the formulation, radioactivity information, and protocol information. The information manager of the dispensing system receives at least a portion of the labeled radiopharmaceutical agent information from the data carrier.

There is therefore provided, in accordance with an embodiment of the present invention, a method for cardiac imaging, including:

administering to an adult human subject an amount of a $^{99m}$Tc-containing species having a radioactivity of less than 5 mCi at a time of administration; and performing a SPECT imaging procedure of a cardiac region of interest (ROI) of the subject, wherein said $^{99m}$Tc-containing species has the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

The following embodiments of the $^{99m}$Tc-containing species having the formula $^{99m}$TcX(Y)$_3$Z are generally applicable to embodiments of $^{99m}$Tc-containing species having the formula $^{99m}$TcX(Y)$_3$Z described throughout the present patent application.

In an embodiment, said Tc-99m-containing species has the structure:

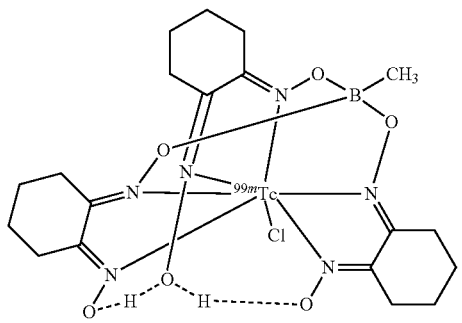

In an embodiment, said $^{99m}$Tc-containing species has the structure:

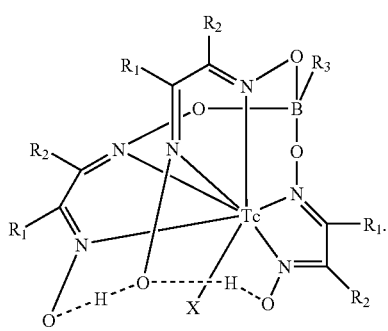

In an embodiment, the method includes mixing:
(i) a source of anion;
(ii) a boronic acid derivative, or compounds which can react in situ to form a boronic acid derivative, having the formula R$_3$B(OR$_7$)(OR$_7$) or a pharmaceutically acceptable salt thereof, wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxy-alkenyl, haloalkyl, haloalkenyl, aryl, arylalkyl, or R$_4$R$_5$N-alkyl and R$_4$ and R$_5$ are each independently hydrogen, alkyl, or arylalkyl, or R$_4$ and R$_5$ when taken together with nitrogen atom to which they are attached form a 5 or 6-membered nitrogen containing heterocycle, and each R$_7$ is independently selected from hydrogen, alkyl and aryl;

(iii) at least one dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$R$_9$)$_n$— wherein n is 3, 4, 5 or 6 and R$_8$ and R$_9$ are each independently hydrogen or alkyl;

(iv) a reducing agent; and
(v) a source of $^{99m}$Tc;

whereby to obtain the $^{99m}$Tc-containing species, wherein administering includes administering the $^{99m}$Tc-containing species thus obtained.

For some applications, the method further includes heating the mixed ingredients for a time and at a temperature sufficient to form said $^{99m}$Tc-containing species. For example, said mixing may further include mixing one or more complexing agents. For some applications, said complexing agent is selected from the group consisting of diethylenetriaminepentaacetic acid, ethylene glycol-bis(β-aminoethyl ether)-N, N'-tetraacetic acid, ethylenediamine tetraacetic acid, citric acid, tartaric acid and malonic acid.

For some applications, said mixing further includes mixing at least one catalyst. For example, said at least one catalyst may include an α-hydroxycarboxylic acid, which may be selected from the group consisting of citric acid, tartaric acid, and malonic acid.

In an embodiment, X is chloride, bromide or iodide. In an embodiment, X is chloride.

In an embodiment, Y is selected from:
dimethyl glyoxime, 1,2-cyclohexanedione dioxime, 1,2-ethanedione dioxime, α-furyldioxime, 1,2-cyclopentanedione dioxime, and 3-methyl-1,2-cyclopentanedione dioxime.
dimethyl glyoxime.
1,2-cyclohexanedione dioxime.
1,2-ethanedione dioxime.
α-furyldioxime.

In an embodiment, Z is B-alkyl, e.g., B-methyl, B-alkoxy, B-benzyl, or B-cycloalkyl.

In an embodiment, the $^{99m}$Tc-containing species is selected from:
$^{99m}$Tc (chlorine) (1,2-cyclohexanedione dioxime)$_3$ methyl boron.
$^{99m}$Tc (chlorine) (dimethyl glyoxime)$_3$ 1-methylpropyl boron.
$^{99m}$Tc (chlorine) (dimethyl glyoxime)$_3$ 4-methylphenyl boron.
$^{99m}$Tc (chlorine) (dimethyl glyoxime)$_3$ cyclopentyl boron.
$^{99m}$Tc (chlorine) (1,2-cyclohexanedione dioxime)$_3$ ethyl boron.
$^{99m}$Tc (chlorine) (dimethyl glyoxime)$_3$ 4-(t-butyl)phenyl boron.
$^{99m}$Tc (chlorine) (dimethyl glyoxime)$_3$ 2-methyl-1-propyl boron.
$^{99m}$Tc (chlorine) (1,2-cyclohexanedione dioxime)$_3$ hydroxy boron.

For some applications, said source of anion is NaCl, said boronic acid derivative is methyl boronic acid; said dioxime is cyclohexanedione dioxime, and said reducing agent is stannous chloride. For some applications, said mixing further includes mixing citric acid and pentetic acid with said source of anion, said boronic acid derivative, said dioxime and said reducing agent. For some applications, said mixing further includes mixing hydroxypropyl gamma cyclodextrin with said source of anion, said boronic acid derivative, said dioxime and said reducing agent.

In an embodiment, performing the SPECT imaging procedure includes performing a dynamic SPECT imaging procedure.

In an embodiment, administering the $^{99m}$Tc-containing species includes dispensing the $^{99m}$Tc-containing species with an initial radioactivity greater than the radioactivity at the time of administration, and such initial radioactivity is calculated based at least in part on a half-life of the $^{99m}$Tc and an estimate of the time of administration, to provide the radioactivity at the time of administration.

In an embodiment, performing the SPECT imaging procedure includes acquiring at least one in 5000 photons emitted from the ROI during the SPECT imaging procedure, such as at least one in 2000 photons emitted from the ROI during the SPECT imaging procedure.

In an embodiment, performing the SPECT imaging procedure includes performing the SPECT imaging procedure with an image acquisition period having a duration of no more than 15 minutes, such as no more than 10 minutes, 8 minutes, 5 minutes, 3 minutes, 2 minutes, 1 minute, 40 seconds, 30 seconds, 20 seconds, 10 seconds, or 5 seconds.

In an embodiment, acquiring the image includes acquiring, during the image acquisition period, at least 200,000 photons emitted from a portion of the ROI, which portion has a volume of no more than 500 cc, such as at least 1,000,000 photons during the image acquisition period from the portion of the ROI having the volume of no more than 200 cc.

In an embodiment, performing the SPECT imaging procedure includes generating an image having a resolution of at least 7×7×7 mm. For some applications, the $^{99m}$Tc-containing species as distributed within the ROI has a range of emission-intensities R, which is measured as emitted photons/unit time/volume, generating the image includes generating a reconstructed three-dimensional emission-intensity image of the ROI, and at least 50% of voxels of the image have inaccuracies of less than 30% of range R. For some applications, the resolution is at least 5×5×5 mm, performing the SPECT imaging procedure includes generating the reconstructed three-dimensional emission-intensity image, and the at least 50% of the voxels of the image have inaccuracies of less than 15% of range R.

In an embodiment, the radioactivity is less than or equal to 4.5 mCi, and administering includes administering the $^{99m}$Tc-containing species having the radioactivity less than or equal to 4.5 mCi. In an embodiment, the radioactivity is less than or equal to 4 mCi, and administering includes administering the $^{99m}$Tc-containing species having the radioactivity less than or equal to 4 mCi. In an embodiment, the radioactivity is less than or equal to 3 mCi, and administering includes administering the $^{99m}$Tc-containing species having the radioactivity less than or equal to 3 mCi. In an embodiment, the radioactivity is less than or equal to 3 mCi, and administering includes administering the $^{99m}$Tc-containing species having the radioactivity less than or equal to 2 mCi. In an embodiment, the radioactivity is less than or equal to 3 mCi, and administering includes administering the $^{99m}$Tc-containing species having the radioactivity less than or equal to 1 mCi.

In an embodiment, the radioactivity is at least 2 mCi, and administering includes administering the $^{99m}$Tc-containing species having the radioactivity that is at least 2 mCi.

In an embodiment, administering includes administering the $^{99m}$Tc-containing species while the subject is at rest, and performing the SPECT imaging procedure includes performing a SPECT rest imaging procedure, and including, before or after the administering while the subject is at rest:

subjecting the subject to stress;

during the stress, administering to the subject a $^{99m}$Tc-containing species having the formula $^{99m}$TcX(Y)$_3$Z; and performing a SPECT stress imaging procedure on the subject.

In an embodiment, administering during the stress includes administering the $^{99m}$Tc-containing species having a radioactivity of less than 18 mCi at a time of the administering.

In an embodiment, administering during the stress includes beginning the administering during the stress within 5 hours of completing the SPECT rest imaging procedure, such as within 1 hour, within 30 minutes, or within 10 minutes of completing the SPECT rest imaging procedure.

For some applications, subjecting the subject to stress includes subjecting the subject to pharmacological stress. Alternatively or additionally, subjecting the subject to stress includes subjecting the subject to exercise stress.

In an embodiment, performing the SPECT stress imaging procedure includes acquiring at least one in 5000 photons emitted from the ROI during the SPECT stress imaging procedure.

In an embodiment, performing the SPECT stress imaging procedure includes performing the SPECT stress imaging procedure with an image acquisition period having a duration of no more than 25 minutes, such as no more than 5 minutes.

There is further provided, in accordance with an embodiment of the present invention, apparatus for performing cardiac imaging, including an imaging system, which includes:

SPECT imaging functionality; and a control unit configured to drive the imaging functionality to perform a SPECT imaging procedure on a cardiac region of interest (ROI) of an adult human subject after administration to the subject of a $^{99m}$Tc-containing species having a radioactivity of less than 5 mCi at a time of administration, wherein said $^{99m}$Tc-containing species has the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

In an embodiment, the control unit is configured to drive the imaging functionality to perform a dynamic SPECT imaging procedure.

In an embodiment, the apparatus includes an automated administration system, configured to receive imaging protocol information for use with the $^{99m}$Tc-containing species, and to perform at least one automated administration of the $^{99m}$Tc-containing species into the subject at least in part responsively to the protocol information.

In an embodiment, the apparatus includes a container containing the $^{99m}$Tc-containing species having the radioactivity of less than 5 mCi at the time of administration.

In an embodiment, the apparatus includes a portable computer-communicatable data carrier associated with the container, the data carrier containing imaging protocol information for use with the $^{99m}$Tc-containing species. For some applications, the apparatus includes an automated administration system, configured to receive imaging protocol information for use with the $^{99m}$Tc-containing species from the data carrier, and to perform at least one automated administration of the $^{99m}$Tc-containing species into the subject at least in part responsively to the protocol information.

There is still further provided, in accordance with an embodiment of the present invention, apparatus for cardiac imaging, including a portable computer-communicatable data carrier, which is configured to contain imaging protocol information for performing SPECT imaging on an adult human subject, the protocol information including an indication of administration of a $^{99m}$Tc-containing species of the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

In an embodiment, the protocol information includes an indication of a radioactivity of the $^{99m}$Tc-containing species of less than 5 mCi at a time of the administration.

In an embodiment, the protocol information includes an indication of performance of a SPECT imaging procedure on the subject, which procedure includes an image acquisition period having a duration not exceeding 5 minutes.

In an embodiment, the protocol information includes an indication of performance of a SPECT imaging procedure on the subject, which procedure includes: (a) a duration of an image acquisition period, and (b) a radioactivity of the $^{99m}$Tc-containing species, wherein a product (a) and (b) is less than 50 mCi*minutes.

In an embodiment, the protocol information includes an indication of performance of a SPECT imaging procedure on the subject, which procedure includes: (a) a duration of an image acquisition period, and (b) a radioactivity of the $^{99m}$Tc-containing species, wherein a product (a) and (b) is less than 30 mCi*minutes.

In an embodiment, the protocol information includes an indication of performance of a SPECT imaging procedure on the subject, which procedure includes: (a) a duration of an image acquisition period, and (b) a radioactivity of the $^{99m}$Tc-containing species, wherein a product (a) and (b) is less than 10 mCi*minutes.

In an embodiment, the apparatus includes a container containing the $^{99m}$Tc-containing species, and the data carrier is associated with the container.

There is additionally provided, in accordance with an embodiment of the present invention apparatus including a container containing a dose of a $^{99m}$Tc-containing species calculated to have a radioactivity of less than 5 mCi at an expected time of administration to an adult human subject, the $^{99m}$Tc-containing species having the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

For some applications, the apparatus includes a portable computer-communicatable data carrier associated with the container, which data carrier is configured to contain information indicating that the container contains the 99m-Tc-containing species having the radioactivity of less than 5 mCi at said expected time of administration. For some applications, the data carrier includes an identifier of the subject.

For some applications, the container further contains a pharmacological stress agent. For some applications, the container further contains a vasodilator.

For some applications, the container further contains I-123 BMIPP.

For some applications, the container further contains $^{99m}$Tc ECDG.

For some applications, the container further contains $^{99m}$Tc-sestamibi. For some applications, container further contains $^{99m}$Tc-tetrofosmin.

For some applications, the dose of the $^{99m}$Tc-containing species includes a first dose the $^{99m}$Tc-containing species, and the container further contains a second dose of a $^{99m}$Tc-containing species having the formula $^{99m}$TcX(Y)$_3$Z.

There is still additionally provided, in accordance with an embodiment of the present invention pharmaceutical or diagnostic composition including a $^{99m}$Tc-containing species having the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or $R_4$ and $R_5$ when taken together with the nitrogen atom to which they are attached form a 5 or 6-membered nitrogen containing heterocycle, wherein the $^{99m}$Tc radioactivity of the $^{99m}$TcX(Y)$_3$Z in the portion of the composition to be administered to a patient is less than 5 mCi.

For some applications, said composition is in unit dosage form and the dosage unit contains less than 5 mCi $^{99m}$Tc radioactivity at a time of administration to a human subject.

For some applications, the composition further includes at least one additional $^{99m}$Tc-containing species different from the $^{99m}$Tc-containing species having the formula $^{99m}$TcX(Y)$_3$Z, such as $^{99m}$Tc-sestamibi or $^{99m}$Tc-tetrofosmin.

There is also provided, in accordance with an embodiment of the present invention, a method for preparing a diagnostic or pharmaceutical composition including a $^{99m}$Tc-containing species having a radioactivity of less than 5 mCi at a time of administration, wherein said $^{99m}$Tc-containing species has the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_1$ and $R_2$ are —(CR$_8$CR$_9$)$_n$— wherein n is 3, 4, 5 or 6 and $R_8$ and $R_9$ are each independently hydrogen or alkyl; and Z is a boron derivative of the formula B—R$_3$ wherein $R_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and $R_4$ and $R_5$ are each independently hydrogen, alkyl, or arylalkyl, or $R_4$ and $R_5$ when taken together with the nitrogen atom to which they are attached form a 5 or 6-membered nitrogen containing heterocycle, the method including mixing:

(i) a source of anion;

(ii) a boronic acid derivative, or compounds which can react in situ to form a boronic acid derivative, having the formula R$_3$B(OR$_7$)(OR$_7$) or a pharmaceutically acceptable salt thereof, wherein $R_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxy-alkenyl, haloalkyl, haloalkenyl, aryl, arylalkyl, or R$_4$R$_5$N-alkyl and $R_4$ and $R_5$ are each independently hydrogen, alkyl, or arylalkyl, or $R_4$ and $R_5$ when taken together with nitrogen atom to which they are attached form a 5 or 6-membered nitrogen containing heterocycle, and each $R_7$ is independently selected from hydrogen, alkyl and aryl;

(iii) at least one dioxime having the formula HON=C(R$_1$)C(R$_2$)=NOH or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_1$ and $R_2$ are —(CR$_8$R$_9$)$_n$— wherein n is 3, 4, 5 or 6 and $R_8$ and $R_9$ are each independently hydrogen or alkyl;

(iv) a reducing agent; and (v) a source of $^{99m}$Tc having an amount of dispensed radiation calculated such that an amount of radiation in a portion of the composition to be administered to a human subject will be less than 5 mCi at an expected time of administration of the portion;

whereby to obtain a composition including $^{99m}$Tc and which has less than 5 mCi $^{99m}$Tc radioactivity at said time of administration.

In an embodiment, mixing includes receiving an indication of the expected time of administration, and calculating the dispensed radiation responsively to the indication For some applications, the method further includes heating the mixed ingredients for a time and at a temperature sufficient to form said $^{99m}$Tc-containing species, such as from about 100° C. to about 140° C.

For some applications, said mixing further includes mixing one or more complexing agents.

For some applications, said complexing agent is selected from the group consisting of diethylenetriamine-pentaacetic acid, ethylene glycol-bis(β-aminoethyl ether)-N,N'-tetraacetic acid, ethylenediamine tetraacetic acid, citric acid, tartaric acid and malonic acid.

For some applications, said mixing further includes mixing at least one catalyst.

For some applications, said at least one catalyst includes an α-hydroxycarboxylic acid. For some applications, said α-hydroxycarboxylic acid is selected from the group consisting of citric acid, tartaric acid, and malonic acid.

There is further provided, in accordance with an embodiment of the present invention, an automated radiopharmaceutical dispensing system for use with a container, the system including:

a robot, configured to manipulate the container; and a control unit, configured to drive the robot to automatically dispense, to the container, a dose of a $^{99m}$Tc-containing species having a dispensed radioactivity calculated to result in a radioactivity of less than 5 mCi at an expected time of administration of the dose, wherein said $^{99m}$Tc-containing species has the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_1$ and $R_2$ are —(CR$_8$CR$_9$)$_n$— wherein n is 3, 4, 5 or 6 and $R_8$ and $R_9$ are each independently hydrogen or alkyl; and Z is a boron derivative of the formula B—R$_3$ wherein $R_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and $R_4$ and $R_5$ are each independently hydrogen, alkyl, or arylalkyl, or $R_4$ and $R_5$ when taken together with the nitrogen atom to which they are attached form a 5 or 6-membered nitrogen containing heterocycle.

In an embodiment, the control unit is configured to receive an indication of the expected time of administration, and to calculate the dispensed radioactivity responsively to the indication.

There is still further provided, in accordance with an embodiment of the present invention, a method for cardiac imaging, including:

administering to an adult human subject a $^{99m}$Tc-containing species having a radioactivity of less than 30 mCi at a time of the administering; and performing a SPECT imaging procedure on a cardiac region of interest (ROI) of the subject with a image acquisition period having a duration not exceeding 5 minutes, wherein said $^{99m}$Tc-containing species has the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_1$ and $R_2$ are —$(CR_8CR_9)_n$— wherein n is 3, 4, 5 or 6 and $R_8$ and $R_9$ are each independently hydrogen or alkyl;

Z is a boron derivative of the formula B—$R_3$ wherein $R_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or $(R_4R_5N)$-alkyl and $R_4$ and $R_5$ are each independently hydrogen, alkyl, or arylalkyl, or $R_4$ and $R_5$ when taken together with the nitrogen atom to which they are attached form a 5 or 6-membered nitrogen containing heterocycle.

For some applications, the radioactivity is less than 15 mCi, such as less than 10 mCi, or less than 5 mCi. For some applications, the radioactivity is greater than 1 mCi.

For some applications, the duration of the image acquisition period does not exceed 3 minutes, e.g., does not exceed 2.5 minutes, or does not exceed 1 minute.

For some applications, performing the SPECT imaging procedure includes, during the image acquisition period, acquiring a number of photons emitted from the $^{99m}$Tc-containing species which is greater than or equal to at least one of the following numbers:

one in 5000 photons emitted by the $^{99m}$Tc-containing species in the ROI during the image acquisition period, and 200,000 photons emitted by the $^{99m}$Tc-containing species in a portion of the ROI, which portion has a volume of no more than 500 cc.

For some applications, acquiring the number of photons includes acquiring at least one in 5000 photons emitted from the ROI during the image acquisition period, such as at least one in 2000 or at least one in 1000 photons emitted from the ROI during the image acquisition period.

For some applications, acquiring the number of photons includes acquiring at least 200,000 photons during the image acquisition period from the portion of the ROI having the target volume of no more than 500 cc. For some applications, the portion of the ROI has a volume of no more than 200 cc, and acquiring the number of photons includes acquiring at least 1,000,000 photons during the image acquisition period from the portion of the ROI having the volume of no more than 200 cc.

For some applications, performing the SPECT imaging procedure includes generating an image having a resolution of at least 7×7×7 mm. For some applications, the $^{99m}$Tc-containing species as distributed within the ROI has a range of emission-intensities R, which is measured as emitted photons/unit time/volume, performing the SPECT imaging procedure generating a reconstructed three-dimensional emission-intensity image of the ROI, and at least 50% of voxels of the image have inaccuracies of less than 30% of range R. For some applications, the resolution is at least 5×5×5 mm, generating the image includes generating the reconstructed three-dimensional emission-intensity image, and the at least 50% of the voxels of the image have inaccuracies of less than 15% of range R.

In an embodiment, administering includes administering the $^{99m}$Tc-containing species while the subject is at rest, and performing the SPECT imaging procedure includes performing a SPECT rest imaging procedure, and including, after completion of the SPECT rest imaging procedure:

subjecting the subject to stress;

during the stress, administering into the subject the $^{99m}$Tc-containing species having a radioactivity of between 15 and 40 mCi at a time of the administering; and performing a SPECT stress imaging procedure on the subject with a stress image acquisition period having a duration not exceeding 5 minutes.

For some applications, administering during the stress includes beginning the administering during the stress within 5 hours of completing the SPECT rest imaging procedure.

In an embodiment, administering includes administering the $^{99m}$Tc-containing species while the subject is at rest, performing the SPECT imaging procedure includes performing a SPECT rest imaging procedure, and including, before administering the $^{99m}$Tc-containing species while the subject is at rest:

subjecting the subject to stress;

during the stress, administering into the subject the $^{99m}$Tc-containing species having a radioactivity of between 15 and 40 mCi at a time of the administering; and performing a SPECT stress imaging procedure on the subject.

For some applications, performing the SPECT stress imaging procedure includes performing the SPECT stress imaging procedure with a stress image acquisition period having a duration not exceeding 5 minutes.

For some applications, the radioactivity of the $^{99m}$Tc-containing species administered during the stress is between 20 and 40 mCi, such as between 25 and 30 mCi.

For some applications, the duration of the stress image acquisition period does not exceed 4 minutes.

For some applications, subjecting the subject to stress includes subjecting the subject to pharmacological stress. For some applications, subjecting the subject to stress includes subjecting the subject to exercise stress. For some applications, subjecting the subject to stress includes administering a vasodilator prior to subjecting the subject to stress. For example, the vasodilator may include nitroglycerin, and administering the vasodilator includes administering the nitroglycerin, or the vasodilator may include isosorbide dinitrate, and administering the vasodilator includes administering the isosorbide dinitrate.

For some applications, administering the $^{99m}$Tc-containing species at rest and during the stress includes administering the $^{99m}$Tc-containing species using an automated administration system that is configured to receive imaging protocol information for use with the $^{99m}$Tc-containing species, and to administer the $^{99m}$Tc-containing species into the subject at least in part responsively to the protocol information.

For some applications, administering the $^{99m}$Tc-containing species at rest and during the stress and performing the SPECT rest and stress imaging procedures include administering the $^{99m}$Tc-containing species at rest and during the stress and performing the SPECT rest and stress imaging procedures while the subject remains in place at a camera of an imaging system.

For some applications, administering the $^{99m}$Tc-containing species at rest and during the stress and performing the SPECT rest and stress imaging procedures include administering the $^{99m}$Tc-containing species at rest and during the stress and performing the SPECT rest and stress imaging procedures during a time period having a duration of no more than 30 minutes.

In an embodiment, administering includes administering the $^{99m}$Tc-containing species while the subject is at rest, performing the SPECT imaging procedure includes performing a SPECT rest imaging procedure, and the method includes, after completion of the SPECT rest imaging procedure:

subjecting the subject to stress;
during the stress, administering to the subject thallium having a radioactivity of between 3 and 5 mCi at a time of the administering; and
performing SPECT stress imaging on the subject.

In an embodiment, administering includes administering the $^{99m}$Tc-containing species while the subject is at rest, performing the SPECT imaging procedure includes performing a SPECT rest imaging procedure, and including, before administering the $^{99m}$Tc-containing species while the subject is at rest:
subjecting the subject to stress;
during the stress, administering to the subject thallium having a radioactivity of between 3 and 5 mCi at a time of the administering; and
performing SPECT stress imaging on the subject.

In an embodiment, administering includes administering the $^{99m}$Tc-containing species while the subject is at rest, performing the SPECT imaging procedure includes performing a SPECT rest imaging procedure, and including:
before administering the $^{99m}$Tc-containing species while the subject is at rest:
subjecting the subject to stress; and
during the stress, administering to the subject thallium having a radioactivity of between 3 and 5 mCi at a time of the administering; and
after administering the $^{99m}$Tc-containing species and the thallium, and before performing the SPECT rest imaging procedure, performing SPECT stress imaging on the subject.

In an embodiment, administering includes administering the $^{99m}$Tc-containing species while the subject is at rest, performing the SPECT imaging procedure includes performing a SPECT rest imaging procedure, and including:
before administering the $^{99m}$Tc-containing species while the subject is at rest:
subjecting the subject to stress; and
during the stress, administering to the subject thallium having a radioactivity of between 3 and 5 mCi at a time of the administering; and
after administering the $^{99m}$Tc-containing species and the thallium, performing SPECT stress imaging on the subject simultaneously with performing the SPECT rest imaging procedure.

In an embodiment,
administering includes subjecting the subject to stress, and administering the $^{99m}$Tc-containing species during the stress,
performing the SPECT imaging procedure includes performing a SPECT stress imaging procedure of the $^{99m}$Tc-containing species, and including:
after administering the $^{99m}$Tc-containing species, administering to the subject, while the subject is at rest, thallium having a radioactivity of between 3 and 5 mCi at a time of the administering; and
after performing the SPECT stress imaging procedure, performing a SPECT rest imaging procedure of the thallium.

In an embodiment,
administering includes subjecting the subject to stress, and administering the $^{99m}$Tc-containing species during the stress,
performing the SPECT imaging procedure includes performing a SPECT stress imaging procedure of the $^{99m}$Tc-containing species, and including:
before administering the $^{99m}$Tc-containing species, administering to the subject, while the subject is at rest, thallium having a radioactivity of between 3 and 5 mCi at a time of the administering; and
after administering the $^{99m}$Tc-containing species and the thallium, performing a SPECT rest imaging procedure of the thallium, before performing the SPECT stress imaging procedure of the $^{99m}$Tc-containing species.

In an embodiment,
administering includes subjecting the subject to stress, and administering the $^{99m}$Tc-containing species during the stress,
performing the SPECT imaging procedure includes performing a SPECT stress imaging procedure of the $^{99m}$Tc-containing species, and including:
before administering the $^{99m}$Tc-containing species, administering to the subject, while the subject is at rest, thallium having a radioactivity of between 3 and 5 mCi at a time of the administering; and
after administering the $^{99m}$Tc-containing species and the thallium, performing a SPECT rest imaging of the thallium simultaneously with performing the SPECT stress imaging procedure of the $^{99m}$Tc-containing species.

For some applications, subjecting the subject to stress includes subjecting the subject to pharmacological stress.

For some applications, subjecting the subject to stress includes subjecting the subject to exercise stress.

For some applications, administering the $^{99m}$Tc-containing species and administering the thallium include administering the $^{99m}$Tc-containing species and the thallium using an automated administration system that is configured to receive imaging protocol information for use with the $^{99m}$Tc-containing species and the thallium, and to administer the $^{99m}$Tc-containing species and the thallium into the subject at least in part responsively to the protocol information.

For some applications, administering the $^{99m}$Tc-containing species, administering the thallium, performing the SPECT rest imaging procedure, and performing the SPECT stress imaging procedure include administering the $^{99m}$Tc-containing species, administering the thallium, performing the SPECT rest imaging procedure, and performing the SPECT stress imaging procedure while the subject remains in place at a camera of an imaging system.

For some applications, administering the $^{99m}$Tc-containing species, administering the thallium, performing the SPECT rest imaging procedure, and performing the SPECT stress imaging procedure include administering the $^{99m}$Tc-containing species, administering the thallium, performing the SPECT rest imaging procedure, and performing the SPECT stress imaging procedure during a time period having a duration of no more than 30 minutes, such as no more than 20 minutes, or no more than 15 minutes.

For some applications, the method includes processing data acquired from the stress imaging to provide a clinically-valuable image.

For some applications, performing the SPECT stress imaging includes performing the SPECT stress imaging for a duration not exceeding 5 minutes.

In an embodiment, the method includes, prior to or during performance of the SPECT imaging procedure, administering to the subject I-123 BMIPP at a radioactivity of between 3 and 5 mCi at a time of the administering, and performing the SPECT rest imaging procedure includes simultaneously imaging the $^{99m}$Tc-containing species and the I-123 BMIPP. For some applications, imaging the I-123 BMIPP includes acquiring, during the rest image acquisition period, a number of photons emitted by the I-123 BMIPP which is greater than or equal to at least one of the following numbers:
one in 5000 photons emitted by the I-123 BMIPP in the ROI during the rest image acquisition period, and
200,000 photons emitted by the I-123 BMIPP in a portion of the ROI, which portion has a volume of no more than 500 cc.

In an embodiment, administering includes administering the $^{99m}$Tc-containing species while the subject is at rest, performing the SPECT imaging procedure includes performing a SPECT rest imaging procedure, and the method includes, after completion of the SPECT rest imaging procedure:

subjecting the subject to stress;

during the stress, administering to the subject Tc-99m ECDG having a radioactivity of less than 35 mCi at a time of the administering; and performing a SPECT stress imaging procedure on the subject.

In an embodiment, performing the SPECT imaging procedure includes performing a first SPECT imaging procedure, and including, after completion of the first SPECT imaging procedure:

administering to the subject at least one additional $^{99m}$Tc-containing species different from the $^{99m}$Tc-containing species having the formula $^{99m}$TcX(Y)$_3$Z; and performing a second SPECT imaging procedure using the at least one additional $^{99m}$Tc-containing species.

For some applications, the at least one additional $^{99m}$Tc-containing species includes $^{99m}$Tc-sestamibi. For some applications, the at least one additional $^{99m}$Tc-containing species includes $^{99m}$Tc-tetrofosmin.

In an embodiment, administering the $^{99m}$Tc-containing species includes administering the $^{99m}$Tc-containing species while the subject is at rest, performing the first SPECT imaging procedure includes performing a first SPECT rest imaging procedure, administering the at least one additional $^{99m}$Tc-containing species includes subject the subject to stress, and administering the at least one additional $^{99m}$Tc-containing species, and performing the second SPECT imaging procedure includes performing a second SPECT stress imaging procedure.

In an embodiment, administering the $^{99m}$Tc-containing species includes subjecting the subject to stress, and administering the $^{99m}$Tc-containing species during the stress, performing the first SPECT imaging procedure includes performing a first SPECT stress imaging procedure, administering the at least one additional $^{99m}$Tc-containing species includes administering the at least one additional $^{99m}$Tc-containing species when the subject is at rest, and performing the second SPECT imaging procedure includes performing a second SPECT rest imaging procedure.

In an embodiment, performing the SPECT imaging procedure includes performing a first SPECT imaging procedure, and including:

prior to administering the $^{99m}$Tc-containing species:
administering to the subject at least one additional $^{99m}$Tc-containing species different from the $^{99m}$Tc-containing species having the formula $^{99m}$TcX(Y)$_3$Z; and
performing a first portion of a second SPECT imaging procedure using the at least one additional $^{99m}$Tc-containing species, administering the $^{99m}$Tc-containing species includes administering the $^{99m}$Tc-containing species after performing the first portion of the second SPECT imaging procedure, performing the first SPECT imaging procedure includes performing the first SPECT imaging procedure after administering the $^{99m}$Tc-containing species, and including performing a second portion of the second SPECT imaging procedure after completing performing of the first SPECT imaging procedure.

In an embodiment, administering the $^{99m}$Tc-containing species includes administering the $^{99m}$Tc-containing species while the subject is at rest, performing the SPECT imaging procedure includes performing a SPECT rest imaging procedure, and including:

prior to administering the $^{99m}$Tc-containing species:
subjecting the subject to stress;
during the stress, administering to the subject at least one additional $^{99m}$Tc-containing species different from the $^{99m}$Tc-containing species having the formula $^{99m}$TcX(Y)$_3$Z; and after performing the SPECT rest imaging procedure, performing a SPECT stress imaging procedure using the at least one additional $^{99m}$Tc-containing species.

For some applications, the at least one additional $^{99m}$Tc-containing species includes $^{99m}$Tc-sestamibi. For some applications, the at least one additional $^{99m}$Tc-containing species includes $^{99m}$Tc-tetrofosmin.

There is additionally provided, in accordance with an embodiment of the present invention, apparatus for performing cardiac imaging, including an imaging system, which includes:

SPECT imaging functionality; and a control unit configured to drive the imaging functionality to perform a SPECT imaging procedure on a cardiac region of interest (ROI) of an adult human subject after administration to the subject of a $^{99m}$Tc-containing species having a radioactivity of less than 30 mCi at a time of the administration, wherein the imaging procedure has a image acquisition period having a duration not exceeding 5 minutes, and wherein said $^{99m}$Tc-containing species has the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

For some applications, the radioactivity is less than 15 mCi, such as less than 10 mCi, or less than 5 mCi. For some applications, the radioactivity is greater than 1 mCi.

For some applications, the control unit is configured to, during the image acquisition period, acquire a number of photons greater than or equal to at least one of the following numbers:

one in 5000 photons emitted from the ROI during the image acquisition period, and 200,000 photons emitted from a portion of the ROI, which portion has a volume of no more than 500 cc.

For some applications, the control unit is configured to drive the imaging functionality to perform a dynamic SPECT imaging procedure.

In an embodiment, the apparatus includes an automated administration system, configured to receive imaging protocol information for use with the $^{99m}$Tc-containing species, and to perform at least one automated administration of the $^{99m}$Tc-containing species into the subject at least in part responsively to the protocol information.

In an embodiment, the apparatus includes a container containing the $^{99m}$Tc-containing species. For some applications, the apparatus includes a portable computer-communicatable data carrier associated with the container, the data carrier containing imaging protocol information for use with the $^{99m}$Tc-containing species. For some applications, the apparatus includes an automated administration system, configured to receive imaging protocol information for use with the $^{99m}$Tc-containing species from the data carrier, and to perform at least one automated administration of the $^{99m}$Tc-containing species into the subject at least in part responsively to the protocol information.

There is still additionally provided, in accordance with an embodiment of the present invention, apparatus for cardiac imaging, including a portable computer-communicatable data carrier, which is configured to contain imaging protocol information for performing SPECT imaging on an adult human subject, the protocol information including an indication of administration of $^{99m}$Tc-containing species having a radioactivity of less than 30 mCi at a time of the administration, and performance of a SPECT imaging procedure with a image acquisition period having a duration not exceeding 5 minutes, wherein said $^{99m}$Tc-containing species has the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy; carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

For some applications, the radioactivity is less than 15 mCi, such as less than 10 mCi, or less than 5 mCi. For some applications, the radioactivity is greater than 1 mCi.

In an embodiment, the apparatus includes a container containing the $^{99m}$Tc-containing species, and the data carrier is associated with the container.

There is yet additionally provided, in accordance with an embodiment of the present invention, a method for cardiac imaging, including:

subjecting a subject to stress;

during the stress, administering to the subject a $^{99m}$Tc-containing species having a radioactivity of between 20 and 40 mCi at a time of the administering; and performing a SPECT stress imaging procedure on a cardiac region of interest (ROI) of the subject, with an image acquisition period having a duration not exceeding 5 minutes; and during the stress image acquisition period, acquiring a number of photons greater than or equal to at least one of the following numbers:

one in 5000 photons emitted from the ROI during the stress image acquisition period, and 200,000 photons emitted from a portion of the ROI, which portion has a volume of no more than 500 cc, wherein said $^{99m}$Tc-containing species has the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy; carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

For some applications, acquiring the number of photons during the stress image acquisition periods includes acquiring at least one in 2000 photons emitted from the ROI during the stress image acquisition period, such as at least one in 1000 photons emitted from the ROI during the stress image acquisition period.

For some applications, acquiring the number of photons during the stress image acquisition periods includes acquiring at least 500,000 photons emitted from the portion of the ROI, such as least 1,000,000 or at least 2,000,000 photons emitted from the portion of the ROI.

For some applications, the duration of the SPECT rest imaging does not exceed 4 minutes, e.g., does not exceed 2 minutes, does not exceed 1 minute, or does not exceed 30 seconds.

For some applications, performing the SPECT stress imaging procedure includes performing three-dimensional analysis in frames, each of which has a duration of between 7 and 13 seconds.

For some applications, subjecting the subject to stress includes subjecting the subject to pharmacological stress. Alternatively or additionally, subjecting the subject to stress includes subjecting the subject to exercise stress.

In an embodiment, the method includes, prior to subjecting the subject to the stress:

administering, while the subject is at rest, thallium to the subject having a radioactivity of between 2 and 5 mCi at a time of the administering; and performing SPECT rest imaging on the subject for a duration not exceeding 3 minutes.

For some applications, the method includes processing data acquired from the rest imaging to provide a clinically-valuable image.

In an embodiment, the method includes, after completion of the stress image acquisition period:

administering to the subject I-123 BMIPP at a radioactivity of between 3 and 5 mCi at a time of the administering;

performing SPECT BMIPP imaging on the subject; and acquiring at least one in 5000 photons emitted from the ROI during the BMIPP imaging.

There is also provided, in accordance with an embodiment of the present invention, a method for cardiac imaging, including performing a SPECT imaging procedure having a total imaging procedure duration of no more than 20 minutes, by:

performing first and second administrations of first and second radiopharmaceutical agents to a subject, respectively, and at least one of the first and second radiopharmaceutical agents includes a $^{99m}$Tc-containing species, performing, during a rest image acquisition period, rest SPECT imaging on a cardiac region of interest (ROI) of the subject, performing, during a stress image acquisition period, stress SPECT imaging on the ROI, and during each of the rest and stress image acquisition periods, acquiring a number of photons greater than or equal to at least one of the following numbers:

one in 5000 photons emitted from the ROI during the image acquisition period, and 200,000 photons emitted from a portion of the ROI, which portion has a volume of no more than 500 cc, wherein said $^{99m}$Tc-containing species has the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

In an embodiment, both the first and second radiopharmaceutical agents include the $^{99m}$Tc-containing species.

In an embodiment, at least one of the first and second radiopharmaceutical agents includes thallium.

For some applications, the total imaging procedure duration is no more than 15 minutes.

There is also provided, in accordance with an embodiment of the present invention, apparatus for performing cardiac imaging, including an imaging system, which includes:

SPECT imaging functionality;

an automated administration system; and a control unit, configured to perform a SPECT imaging procedure having a total imaging procedure duration of no more than 20 minutes, by:

driving the automated administration system to perform first and second administrations of first and second radiopharmaceutical agents to a subject, respectively, wherein at least one of the first and second radiopharmaceutical agents includes a $^{99m}$Tc-containing species, and driving the imaging functionality to:

perform, during a rest image acquisition period, rest SPECT imaging on a cardiac region of interest (ROI) of the subject, perform, during a stress image acquisition period, stress SPECT imaging on the ROI, and during each of the rest and stress image acquisition periods, acquire a number of photons greater than or equal to at least one of the following numbers:

one in 5000 photons emitted from the ROI during the image acquisition period, and 200,000 photons emitted from a portion of the ROI, which portion has a volume of no more than 500 cc, wherein said $^{99m}$Tc-containing species has the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

There is further provided, in accordance with an embodiment of the present invention, a method for cardiac imaging, including:

administering a $^{99m}$Tc-containing species to an adult human subject;

performing a SPECT imaging procedure on a cardiac region of interest (ROI) of the subject; and during the SPECT imaging procedure, acquiring at least one in 5000 photons emitted from the $^{99m}$Tc-containing species in the ROI during the SPECT imaging acquisition procedure, wherein said $^{99m}$Tc-containing species has the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

In an embodiment, administering the $^{99m}$Tc-containing species includes administering the $^{99m}$Tc-containing species with a radioactivity at a time of the administering, and a product of (a) a duration of the SPECT imaging procedure and (b) the radioactivity is less than 50 mCi*minutes, such as less than 30 mCi*minutes, or less than 10 mCi*minutes.

There is still further provided, in accordance with an embodiment of the present invention, apparatus for performing cardiac imaging on a human subject to whom $^{99m}$Tc-containing species has been administered, the apparatus including an imaging system, which includes:

SPECT imaging functionality; and a control unit configured to drive the imaging functionality to:

perform a SPECT imaging procedure on a cardiac region of interest (ROI) of the subject, and during the SPECT imaging procedure, acquire at least one in 5000 photons emitted from the $^{99m}$Tc-containing species in the ROI during the SPECT imaging procedure, wherein said $^{99m}$Tc-containing species has the formula $^{99m}$TcX(Y)$_3$Z, wherein:

X is an anion;

each Y, which is independently chosen, is a vicinal dioxime having the formula HON═C(R$_1$)C(R$_2$)═NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

There is also provided, in accordance with an embodiment of the present invention a method for cardiac imaging, including:

while a subject is at rest, performing a rest administration to the subject of a $^{99m}$Tc-containing species;

after completion of the rest administration, performing a flush administration to the subject;

beginning less than 10 seconds of the completion of the flush administration, performing a low-resolution SPECT rest imaging procedure on a cardiac region of interest (ROD of the subject, with a low-resolution rest image acquisition period having a duration between 20 and 40 seconds, wherein the low-resolution SPECT rest imaging procedure includes a plurality of low-resolution rest frames having an average low-resolution rest frame duration;

beginning less than 10 seconds after completion of the low-resolution SPECT rest imaging procedure, performing a high-resolution SPECT rest imaging procedure on the ROI, with a high-resolution rest image acquisition period having a duration of between 4 and 6 minutes, the high-resolution SPECT rest imaging procedure includes a plurality of high-resolution rest frames having an average high-resolution rest frame duration that is at least 2 times the average low-resolution rest frame duration;

after completion of the high-resolution SPECT rest imaging procedure, subjecting the subject to stress;

after subjecting the subject to the stress, performing a stress administration to the subject of a $^{99m}$Tc-containing species;

after the stress administration, performing a low-resolution SPECT stress imaging procedure on a cardiac region of interest (ROD of the subject, with a low-resolution stress image acquisition period having a duration between 20 and 40 seconds, wherein the low-resolution SPECT stress imaging procedure includes a plurality of low-resolution stress frames having an average low-resolution stress frame duration; and after completion of the low-resolution SPECT stress imaging procedure, performing a high-resolution SPECT stress imaging procedure on the ROI, with a high-resolution stress image acquisition period having a duration of between 4 and 6 minutes, wherein the high-resolution SPECT stress imaging procedure includes a plurality of high-resolution stress frames having an average high-resolution stress frame duration that is at least 2 times the average low-resolution stress frame duration, wherein said $^{99m}$Tc-containing species has the formula $^{99m}$TcX(Y)$_3$Z, wherein:

X is an anion;

each Y, which is independently chosen, is a vicinal dioxime having the formula HON═C(R$_1$)C(R$_2$)═NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

In an embodiment, the $^{99m}$Tc-containing species administered while the subject is at rest has a radioactivity of between 6 and 15 mCi at a time of the rest administration. In an embodiment, the average low-resolution rest frame duration is between 3 and 7 seconds.

For some applications, performing the low-resolution SPECT rest imaging procedure includes acquiring on average during each of the low-resolution rest frames at least 200,000 photons emitted from the ROI. For some applications, performing the low-resolution SPECT rest imaging procedure includes estimating an input function.

For some applications, the average high-resolution rest frame duration is at least 3 times the average low-resolution rest frame duration. For some applications, the average high-resolution rest frame duration is between 15 and 25 seconds.

For some applications, performing the high-resolution SPECT rest imaging procedure includes acquiring on average during each of the high-resolution rest frames at least 200,000 photons emitted from the ROI.

For some applications, the $^{99m}$Tc-containing species administered after subjecting the subject to stress has a radioactivity of between 20 and 40 mCi at a time of the stress administration.

For some applications, the average low-resolution stress frame duration is between 3 and 7 seconds.

For some applications, performing the low-resolution SPECT stress imaging procedure includes acquiring on average during each of the low-resolution stress frames at least 600,000 photons emitted from the ROI.

For some applications, performing the low-resolution SPECT stress imaging procedure includes estimating counts in a cardiac blood pool.

For some applications, the average high-resolution stress frame duration is at least 3 times the average low-resolution stress frame duration. For some applications, the average high-resolution stress frame duration is between 15 and 25 seconds.

For some applications, performing the high-resolution SPECT stress imaging procedure includes acquiring on average during each of the high-resolution stress frames at least 600,000 photons emitted from the ROI.

For some applications, subjecting the subject to stress includes subjecting the subject to pharmacological stress. Alternatively or additionally, subjecting the subject to stress includes subjecting the subject to exercise stress.

There is further provided, in accordance with an embodiment of the present invention, a method for cardiac imaging, including:

administering to an adult human subject a first $^{99m}$Tc-containing species;

performing a SPECT rest imaging procedure on a cardiac region of interest (ROI) of the subject;

during the rest imaging procedure, acquiring a number of photons emitted from the first $^{99m}$Tc-containing species which is greater than or equal to at least one of the following numbers:

one in 5000 photons emitted by the first $^{99m}$Tc-containing species in the ROI during the rest imaging procedure, and 200,000 photons emitted by the first $^{99m}$Tc-containing species in a portion of the ROI, which portion has a volume of no more than 500 cc;

subjecting the subject to stress;

during the stress, and within 5 hours of completing the rest imaging procedure, administering to the subject a second $^{99m}$Tc-containing species;

performing a SPECT stress imaging procedure on the ROI; and during the stress imaging procedure, acquiring a number of photons emitted from the second $^{99m}$Tc-containing species which is greater than or equal to at least one of the following numbers:

one in 5000 photons emitted by the second $^{99m}$Tc-containing species in the ROI during the rest imaging procedure, and 200,000 photons emitted by the second $^{99m}$Tc-containing species in a portion of the ROI, which portion has a volume of no more than 500 cc, wherein the second $^{99m}$Tc-containing species has the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

For some applications, performing the rest imaging procedure includes performing the rest imaging procedure having a rest image acquisition period having a duration not exceeding 5 minutes.

In an embodiment, the first $^{99m}$Tc-containing species has the formula $^{99m}$TcX(Y)$_3$Z, wherein:

X is an anion;

each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and Z is a boron derivative of the formula B—R$_3$ wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

For some applications, the first $^{99m}$Tc-containing species includes $^{99m}$Tc-sestamibi, $^{99m}$Tc-tetrofosmin, $^{99m}$Tc-Hynic Annexin, or $^{99m}$Tc-TcN-NOET.

For some applications, administering the second $^{99m}$Tc-containing species includes administering the second $^{99m}$Tc-containing species within 2 hours of completing the rest imaging procedure, such as within 1 hour of completing the rest imaging procedure, within 30 minutes of completing the rest imaging procedure, or within 10 minutes of completing the rest imaging procedure.

There is still further provided, in accordance with an embodiment of the present invention, a method for imaging, including:

setting one or more parameters of an imaging procedure for a subject while the subject is positioned at a camera of an imaging system;

performing a first scan of the subject using the one or more parameters; and performing a second scan of the subject using the one or more parameters.

There is additionally provided, in accordance with an embodiment of the present invention, apparatus including:

a container containing one or more radiopharmaceuticals for use with one of the protocols described herein; and an information carrier containing protocol information relating to the one of the protocols.

There is still additionally provided, in accordance with an embodiment of the present invention, a camera configured to perform one of the protocols described herein.

The present invention will be more fully understood from the following detailed description of embodiments thereof, taken together with the drawings, in which:

BRIEF DESCRIPTION OF THE DRAWING

FIGS. 6A-L are timelines illustrating teboroxime imaging protocols, in accordance with respective embodiments of the present invention;

DETAILED DESCRIPTION OF EMBODIMENTS

Overview of Imaging System

Figure 2:
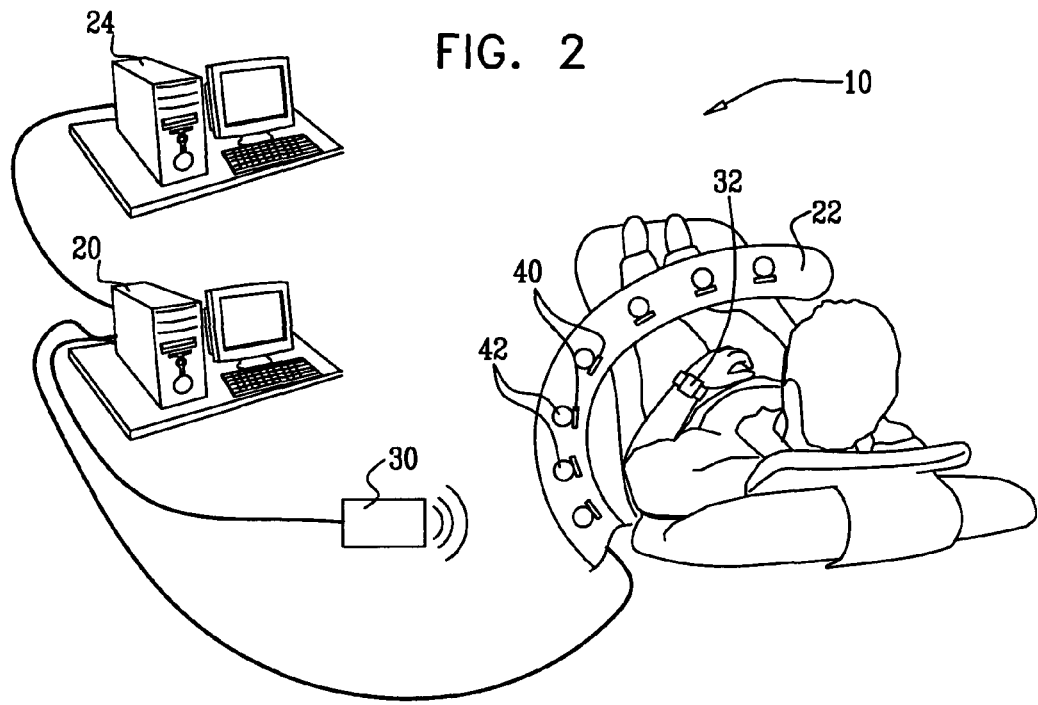
FIG. 2 is a schematic illustration of an imaging system, in accordance with an embodiment of the present invention.

FIG. 2 is a schematic illustration of a SPECT imaging system 10, in accordance with an embodiment of the present invention. Imaging system 10 comprises a control unit 20, a camera 22, and an imaging workstation 24. Typically, control unit 20 and imaging workstation 24 comprise one or more standard personal computers or servers with appropriate memory, communication interfaces and software for carrying out the functions prescribed by relevant embodiments of the present invention. This software may be downloaded to the control unit and imaging workstation in electronic form over a network, for example, or it may alternatively be supplied on tangible media, such as CD-ROM.

Control unit 20 typically comprises: (a) image acquisition functionality, which is configured to drive camera 22 to perform image acquisition of the patient; (b) image reconstruction functionality, which is configured to perform an image reconstruction procedure on the acquired image; (c) image analysis functionality, which is configured to perform an image analysis procedure on the reconstructed image; and (d) diagnosis functionality, which is configured to perform a diagnostic procedure using the results of the image analysis procedure. It will be appreciated that control unit 20 may comprise a plurality of personal computers or servers, each of which performs one or more of these procedures, and that one or more of these computers or servers may be located remotely from camera 22. Imaging workstation 24 displays the reconstructed images and allows the attending healthcare worker to view and manipulate the images.

Imaging system 10 typically customizes one or more of these procedures at least in part responsively to imaging protocol information and/or patient-specific information read by a communication element 30 from a patient-specific data carrier 32, such as described in International Application PCT/IL2006/000562, filed May 11, 2006, which published as PCT Publication WO 2006/129301, and/or in the other patent applications, patent application publications, and/or patents incorporated herein by reference.

For some applications, camera 22 utilizes techniques described in the above-mentioned PCT Publications WO 06/051531 and/or WO 05/119025, and/or in the other patent applications, patent application publications, and/or patents incorporated herein by reference.

In an embodiment of the present invention, camera 22 comprises a plurality of detectors 40, each of which is coupled to a respective angular orientator 42. Each of the detectors comprises a plurality of gamma ray sensors, such as a pixelated CZT array, and a collimator. For example, the array may include 16×64 pixels. Control unit 20 drives, typically separately, each of the orientators to orient its respective detector in a plurality of orientations with respect to a region of interest (ROI). Control unit 20 produces a SPECT image from a plurality of radiation acquisitions acquired with the detectors in different relative orientations.

In an embodiment of the present invention, imaging system 10 is configured to perform imaging of the subject while the subject is in a substantially upright position. For example, the system may comprise a chair. Performing the imaging while the subject is upright generally reduces interference caused by photon emissions from the liver, which becomes quickly contaminated after teboroxime administration. Upright positioning causes the liver to be positioned further from the heart than the liver is when the subject is recumbent, because of the lower position of the diaphragm. Alternatively, imaging system 10 is configured to perform imaging while the subject is recumbent, or partially upright.

In an embodiment of the present invention, imaging system 10 is configured to perform ROI-centric imaging of the heart, such as by using techniques described in PCT/IL2005/001173, filed Nov. 9, 2005, which published as PCT Publication WO 2006/051531, and/or in other patent applications and publications incorporated herein by reference.

In an embodiment of the present invention, imaging system 10 is configured to at least partially correct for liver contamination by modeling the uptake of teboroxime in the liver, and removing expected liver emissions from the detected emissions. For example, techniques may be used that are described in the above-mentioned article by Sitek A et al.

Figure 3:
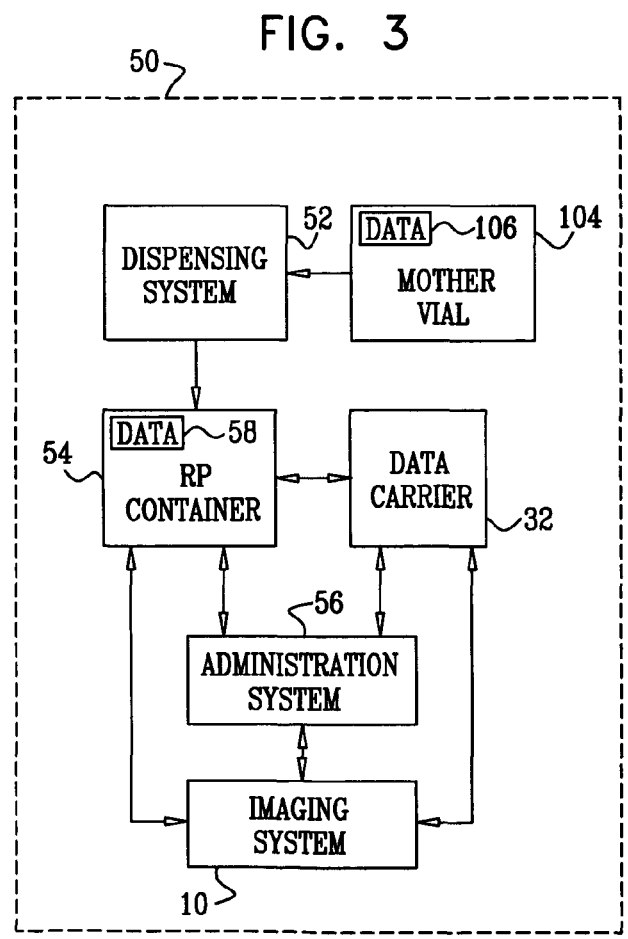
FIG. 3 is a schematic illustration of an end-to-end automated system for medical imaging, in accordance with an embodiment of the present invention.

Reference is made to FIG. 3, which is a schematic illustration of an end-to-end automated system 50 for medical imaging, in accordance with an embodiment of the present invention. System 50 comprises a plurality of integrated elements that are configured to electronically exchange information among one another. In addition to imaging system 10, described hereinabove with reference to FIG. 2, the elements include an automated radiopharmaceutical dispensing system 52 (described hereinbelow with reference to FIG. 5), a portable information-bearing radiopharmaceutical agent container 54, portable patient-specific data carrier 32, and an automated administration system 56 (described hereinbelow with reference to FIG. 4). Typically, a data carrier 58 is physically coupled to container 54. The systems perform their respective automated functions at least in part responsively to the exchanged information. The elements typically authenticate one another via the exchanged information, in order to ensure that only authorized elements participate in the system, and that only authorized and appropriate functions are performed. System typically utilizes technique described in International Application PCT/IL2006/000562, filed May 11, 2006, and/or in the other patent applications, patent application publications, and/or patents incorporated herein by reference.

System 50 assigns a portable patient-specific data carrier 32 to each patient, and transmits information to data carrier 32, including at least a patient identifier (typically, the patient's identification code and/or name), and the assigned administration and imaging protocols. Additional patient data parameters recorded may include physiological data such as girth, height and weight. Prior to administration of a radiolabeled radiopharmaceutical agent stored in agent container 54, administration system 56 authenticates container 54 and verifies the identity of the patient, using information provided by patient-specific data carrier 32 and container data carrier 58. Typically, all or a portion of the information used for such verification is encrypted, and administration system 56 decrypts the information during the verification procedure.

Overview of Automated Administration System

Figure 4:
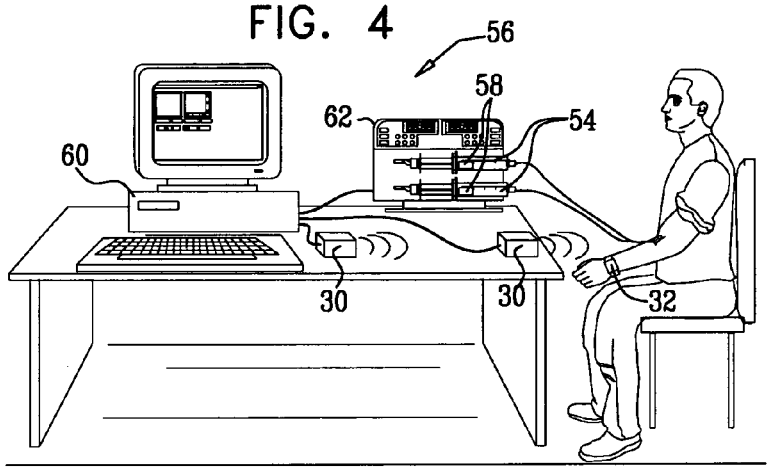
FIG. 4 is a schematic illustration of an automated administration system, in accordance with an embodiment of the present invention.

Reference is made to FIG. 4, which is a schematic illustration of automated administration system 56, in accordance with an embodiment of the present invention. Administration system 56 comprises a control unit 60, at least one communication element 30, and, for some applications, an automated administration device 62. Typically, control unit 60 comprises a standard personal computer or server with appropriate memory, communication interfaces and software for carrying out the functions prescribed by relevant embodiments of the present invention. This software may be downloaded to the control unit in electronic form over a network, for example, or it may alternatively be supplied on tangible media, such as CD-ROM. Typically, radiopharmaceutical agent container 54 comprises a cartridge into which a syringe containing the agent(s) has been placed.

Upon authenticating container 54, verifying the identity of the patient, and performing additional verifications, control unit 60 generates an administration signal that triggers administration to the patient of the labeled radiopharmaceutical agent(s) stored in container 54. For applications in which administration system 56 comprises automated administration device 62, container 54 is operatively coupled to device 62, and the signal drives administration device 62 to administer the labeled radiopharmaceutical agent(s) stored therein to the patient. Automated administration device 62 is configured to perform intravenous (IV) injection, intramuscular (IM) injection, subcutaneous injection, transdermal application, oral administration, nasal administration, inhalation, transcervical application, transrectal administration, or another type of administration known in the art. (It is to be understood that although the administration signal triggers administration of the agent, for some applications automated administration device 62 does not administer the agent until a healthcare worker provides a final authorization to do so, such as to comply with regulatory safety requirements.) For applications in which administration system 56 does not comprise automated administration device 62, the administration signal triggers administration of the agent by instructing a healthcare worker to manually administer the agent to the patient.

For some applications, based on administration protocol information received from data carrier 58 of radiopharmaceutical agent container 54 and/or patient-specific data carrier 32, control unit 60 customizes the administration of the labeled radiopharmaceutical agent(s) contained in agent container 54, typically using information provided by patient-specific data carrier 32 or data carrier 58 of container 54. For example, system 56 may customize a time-dependent administration profile of the labeled radiopharmaceutical agent, such as a rate of administration. Alternatively or additionally, system 56 may administer less than the entire dose of the labeled radiopharmaceutical agent, e.g., based on feedback from imaging system 10 during an imaging procedure. For some applications, administration system 56 administers a plurality of labeled radiopharmaceutical agents, either sequentially or premixed together within a single agent container 54 (i.e., as a cocktail).

In an embodiment of the present invention, automated administration device 62 is configured to use pre-packaged ready-to-use radiopharmaceutical agent containers 54, into which are inserted syringes pre-filled with one or more radiopharmaceutical agents, such as teboroxime. The pre-filled syringes are typically distributed as a kit, which, for some applications, includes additional pharmacological agents (such as pharmacological stress agents, dipyridmole, adenosine, persantine, A2A, nitroglycerin, another vasodilator, or another imaging-enhancing imaging product). Several embodiments of radiopharmaceutical agent container 54 are described in International Application PCT/IL2006/000562, filed May 11, 2006, such as with reference to FIGS. 9A-H thereof.

For some applications, administration system 56 uses techniques described in International Application PCT/IL2006/000562, filed May 11, 2006, which published as PCT Publication WO 06/129301, which is assigned to the assignee of the present application and is incorporated herein by reference, and/or in U.S. patent application Ser. No. 11/750,057, filed May 17, 2007, which published as U.S. Patent Application Publication 2008/0131362, and is assigned to the assignee of the present application and is incorporated herein by reference, and/or in the other patent applications, patent application publications, and/or patents incorporated herein by reference.

In some embodiments of the present invention, protocol information from any of the protocols described is stored in at least one portable computer-communicatable data carrier associated with agent container 54, such as in patient-specific data carrier 32 and/or in container data carrier 58.

Overview of Dispensing System

Figure 5:
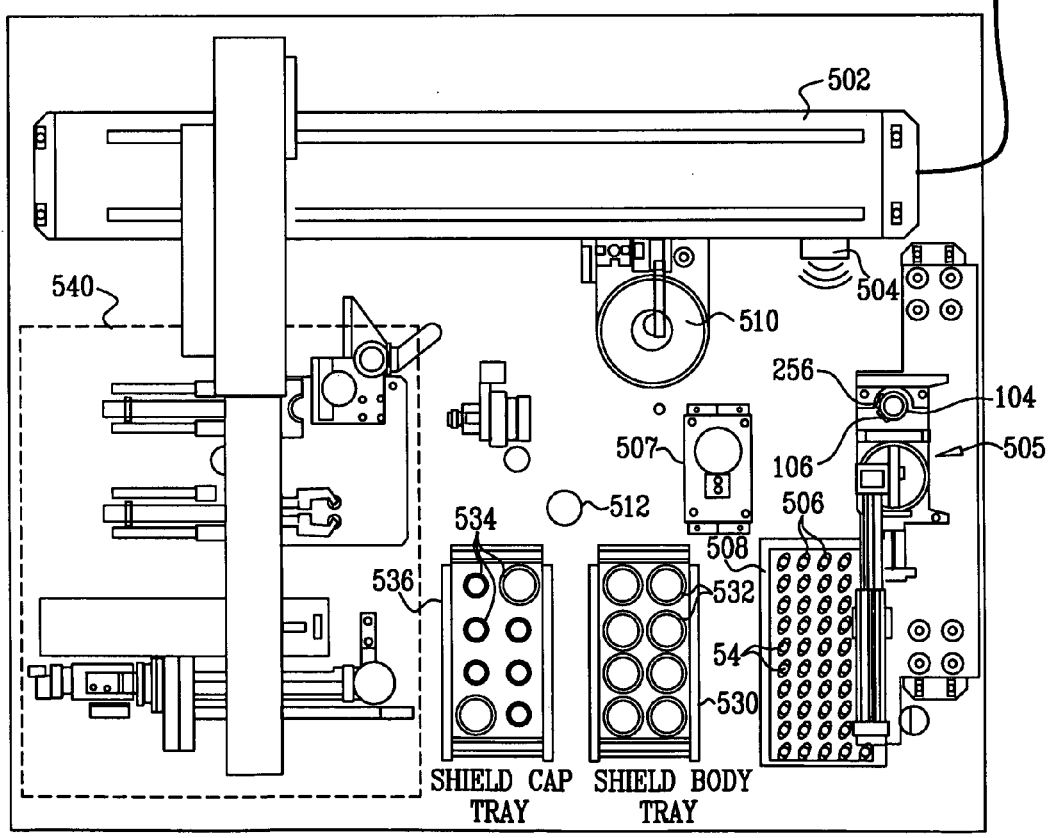
FIG. 5 is a schematic illustration of an automated radiopharmaceutical dispensing system, in accordance with an embodiment of the present invention.

Reference is made to FIG. 5, which is a schematic illustration of automated radiopharmaceutical dispensing system 52, in accordance with an embodiment of the present invention. System 52 comprises a control unit 500, at least one robot 502, and at least one communication element 504, which, for some applications, is coupled to robot 502. Control unit 500 typically comprises a conventional personal computer running a conventional operating system, such as Windows XP, with appropriate memory, communication interfaces and software for carrying out the functions described herein. This software may be downloaded to the control unit in electronic form over a network, for example, or it may alternatively be supplied on tangible media, such as CD-ROM. Control unit 500 is in communication with other elements of system 10. The control unit notifies appropriate elements of the system upon successful completion of dispensing of a dose.

At least one radiolabeled mother vial 104 is placed in a shielded vials complex 505 of dispensing system 52. Control unit 500 authenticates the mother vial, typically by actuating communication element 504 to read authentication information stored in a mother vial data carrier 106 associated with mother vial 104. Upon successful authentication, control unit 500 actuates communication element 504 to read radiopharmaceutical-related information from data carrier 106 of the mother vial, including the radiopharmaceutical agent type, isotope type, batch, lot, radiochemical purity (RCP), preparation time, and half-life information. Dispensing system 52 assays the radioactivity per unit volume of the labeled radiopharmaceutical agent contained in the mother vial. Robot 502 picks up an empty syringe 506 from a syringe tray 508, draws a predetermined amount of solution from mother vial 104, and brings the syringe to a dose calibrator 510. The syringe used for the assaying is typically discarded into a waste container 512. Typically, robot 502 brings the mother vial to a weighing station 507 for verification that the vial contains the indicated solution volume.

Dispensing system 52 receives a patient-specific dose request for at least one specific labeled radiopharmaceutical agent, having a specific dose, radioactivity, and solution volume. Responsively to the patient-specific dose request, the dispensing system typically customizes the prepared dose. To fill the request, control unit 500 calculates a required volume of the labeled radiopharmaceutical agent and a required volume of saline solution for dilution, if any. To perform this calculation, control unit 500 uses (a) information read from data carrier 106 (such as the half-life of the labeling isotope of the labeled radiopharmaceutical agent), and (b) the assayed radioactivity of the labeled radiopharmaceutical agent.

For some applications, control unit 500 authenticates mother vial license information read from data carrier 106, in order to verify that a license is available for dispensing the requested dose. Dispensing proceeds only if a license is available and authenticated. The use of such a license generally provides increased quality control of the imaging process, by verifying that only approved manufacturers (or distributors) are able to provide radiopharmaceutical agents for use with system 10. A lack of precision in any aspect of an imaging procedure, which may result from the use of an agent that has not been tested and approved for use with system 10, often causes a deterioration of the resultant image quality and/or ability to make accurate and/or quantitative diagnoses.

Control unit 500 actuates robot 502 to pick up an empty radiopharmaceutical agent container 54 from tray 508. Typically, but not necessarily, container 54 comprises a syringe. Container 54 has coupled thereto a data carrier 58. For some applications, syringes 506 and containers 54 are stored in a single tray, as shown in FIG. 5, while for other applications, they are stored in separate trays. Robot 502 typically authenticates container 54, typically by actuating communication element 504 to read authentication information stored in data carrier 58.

Robot 502 removes the needle cap from container 54, turns the container over, and brings container 54 to the appropriate mother vial 104. The robot actuates the container to draw the calculated volume of labeled radiopharmaceutical agent from the mother vial, typically by inserting the needle of container 54 through a membrane of mother vial 104, and withdrawing a plunger of container 54 until the desired volume of agent has been drawn from the mother vial. The robot typically brings the syringe to dose calibrator 510 for quality control assaying of radioactivity. If necessary, robot 502 brings container 54 to a saline vial, and actuates the container to draw the required volume of saline solution into the container. Robot 502 replaces the needle cap on the container, and turns the container over. Alternatively, saline solution is drawn prior to drawing the labeled radiopharmaceutical agent from mother vial 104. For some applications, a needle of the container 54 is changed between drawings.

For dispensing a cocktail of labeled radiopharmaceutical agents, each having a respective dose, robot 502 repeats these steps for a plurality of mother vials 104, typically changing the needle of container 54 between drawings. During dispensing of such a cocktail, robot 502 typically draws first from the mother vial containing the lower or lowest radiation labeled radiopharmaceutical agent, such as to reduce any effect the assaying of the first agent may have on the assaying of the subsequent agent(s).

System 52 typically performs a quality control check on the dispensed radiopharmaceutical solution to confirm that the solution contains the desired dose(s) of the radiopharmaceutical agent(s) and radioactivity level.

Control unit 500 activates communication element 504 to write radiopharmaceutical information to data carrier 58 of container 54. For some applications, the data carrier is coupled to the container prior to placement of the container in dispensing system 52, while for other applications, robot 502 couples a data carrier to each container during or after the dispensing process.

Robot 502 brings the filled container to a shield body tray 530, and inserts the container into a container shield 532. The robot picks up a shield cap 534 from a shield cap tray 536, and secures it to container shield 532. For some applications, data carrier 58 is coupled to shield 532 or cap 534, rather than directly to container 54. Alternatively, separate data carriers 58 are coupled to the container and the shield or cap.

In an embodiment of the present invention, dispensing system 52 comprises a print area 540, at which dispensing system 52 prints and attaches at least one conventional label to container 54, shield 532, and/or cap 534, in order to comply with regulatory labeling requirements. The dispensing system typically prints yet another conventional label for placement on a basket that holds a plurality of containers 54 for transport within or between healthcare facilities.

After the dispensing of container 54 has been completed, robot 502 brings the container to a completed container tray (tray not shown in the figure).

For some applications, dispensing system 52 uses techniques described in International Application PCT/IL2006/000562, filed May 11, 2006, and/or in the other patent applications, patent application publications, and/or patents incorporated herein by reference.

Clinically-Valuable Teboroxime Images

Figure 1:
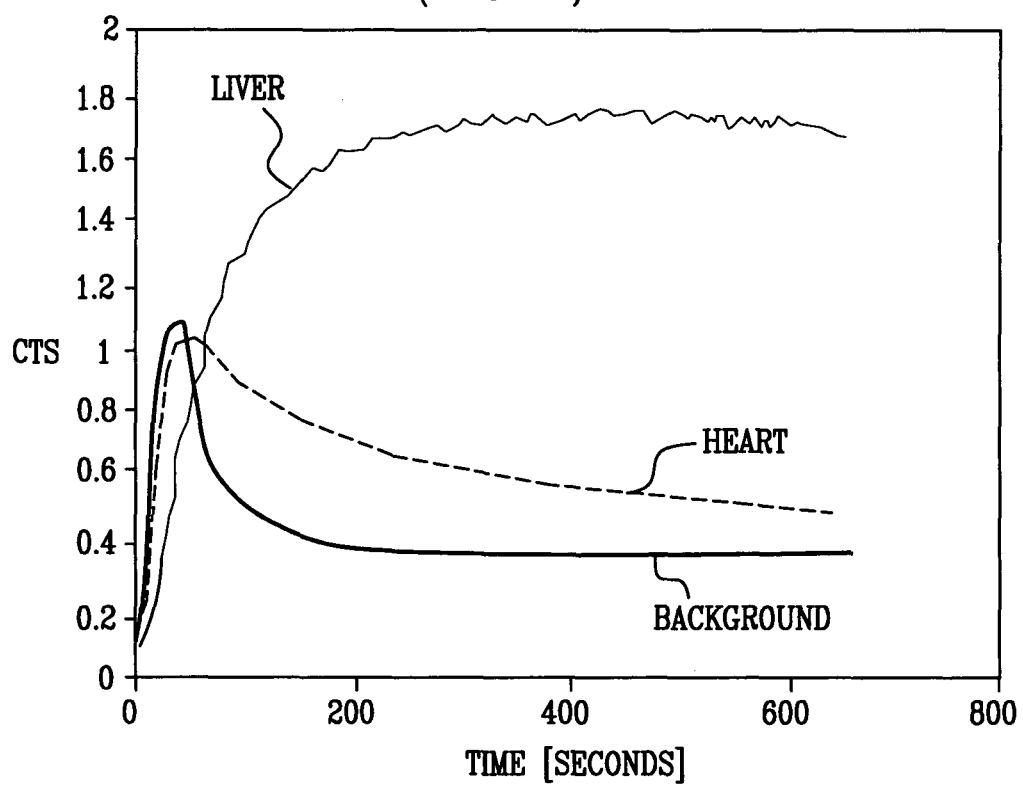
FIG. 1 is a graph showing the average teboroxime uptake as a function of time post-injection for the heart, liver, and background, as known in the prior art.

In an embodiment of the present invention, imaging system 10 produces a "clinically-valuable image" of a cardiac region of interest (ROI) upon administration of teboroxime at a dose of between about 6 and about 50 mCi, e.g., between about 6 and about 30 mCi, such as between about 6 and about 15 mCi, e.g., between about 8 and about 12 mCi. For some applications, such image is acquired during a time period having a duration of no more than 5 minutes, such as no more than about 3 minutes, or no more than about 2.5 minutes, e.g., about 2 minutes, commencing between 1 and 3 minutes after administration of the teboroxime. Completion of image acquisition thus occurs before the concentration of teboroxime in the liver reaches a level that substantially reduces the accuracy of the imaging, as shown in FIG. 1. For example, the completion of image acquisition may occur less than 6 minutes after completion of the administration, such as less than 5 minutes after completion of the administration, e.g., less than 4 minutes after completion of the administration.

For some applications, imaging system 10 produces a clinically-valuable image of a cardiac ROI upon administration of the teboroxime at a given dose and during a time period having a given duration, wherein the product of the dose and the duration is less than 50 mCi*minutes, e.g., less than 30, 20, 10, or 5 mCi*minutes.

In an embodiment of the present invention, imaging system 10 performs a dynamic imaging study by acquiring a plurality of clinically-valuable images during the time period, such as at least 18 images, e.g., at least 24 images. Typically, the time resolution of such dynamic images is between about 5 and about 40 seconds per full scan of the heart.

In an embodiment of the present invention, imaging system 10 performs a dynamic imaging study with frames having a duration of less than about one minute, e.g., less than or equal to about 40 seconds, or less than or equal to about 30 seconds.

A "clinically-valuable image," as used in the present application, is an image of the cardiac ROI containing a radiopharmaceutical, such as the teboroxime (or teboroxime in combination with additional radiopharmaceutical agent(s) or substances, such as described hereinbelow with reference to FIGS. 6B, 6C, 6H, 6I, and 6J), which image fulfills one or more of the following criteria:

the image is generated according to a protocol, including at the radiopharmaceutical dose specified by the protocol, using a high-definition SPECT camera, for example, camera 22 of imaging system 10, described hereinabove with reference to FIG. 2, which camera, during the imaging of the cardiac ROI, is capable of acquiring at least one of 5000 photons emitted from the ROI during the image acquisition procedure, such as at least one of 4000, 3000, 2500, 2000, 1500, 1200, 1000, 800, 600, 400, 200, 100, or 50 photons emitted from the ROI. In one particular embodiment, the camera is capable of acquiring at least one of 2000 photons emitted from the ROI during the image acquisition procedure;

the image is generated according to a protocol, including at the radiopharmaceutical dose and image acquisition duration specified by the protocol, using a high-definition SPECT camera, for example, camera 22, which, during the imaging of the ROI, is capable of acquiring at least 200,000 photons, such as at least 500,000, 1,000,000, 2,000,000, 3,000,000, 4,000,000, 5,000,000, 8,000,000, or 10,000,000 photons, emitted from a portion of the ROI, which portion has a volume of no more than 500 cc, such as a volume of no more than 500 cc, 400 cc, 300 cc, 200 cc, 150 cc, 100 cc, or 50 cc. In one particular embodiment, the camera is capable of acquiring at least 1,000,000 photons emitted from a volume of the ROI having a volume of no more than 200 cc;

the image has a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein the labeled radiopharmaceutical agent as distributed within the ROI has a range of emission-intensities R (which is measured as emitted photons/unit time/volume), and wherein at least 50% of the voxels of the reconstructed three-dimensional emission-intensity image of the ROI have inaccuracies of less than 30% of range R, such as less than 25%, 20%, 15%, 10%, 5%, 2%, 1%, or 0.5% of range R. For example, the agent may emit over a range from 0 photons/second/cc to $10^5$ photons/second/cc, such that the range R is $10^5$ photons/second/cc, and at least 50% of the voxels of the reconstructed three-dimensional intensity image of the ROI have inaccuracies of less than 15% of range R, i.e., less than $1.5 \times 10^4$ photons/second/cc. For some applications, the study produce a parametric image related to a physiological process occurring in each voxel. In one particular embodiment, the image has a resolution of at least 5×5×5 mm, and at least 50% of the voxels have inaccuracies of less than 15% of range R;

the image is generated according to a protocol, including at the radiopharmaceutical dose and image acquisition duration specified by the protocol, and the image has a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein the labeled radiopharmaceutical agent as distributed within the ROI has a range of emission-intensities R (which is measured as emitted photons/unit time/volume), and wherein at least 50% of the voxels of the reconstructed three-dimensional emission-intensity image of the ROI have inaccuracies of less than 30% of range R, such as less than 25%, 20%, 15%, 10%, 5%, 2%, 1%, or 0.5% of range R. For example, the agent may emit over a range from 0 photons/second/cc to $10^5$ photons/second/cc, such that the range R is $10^5$ photons/second/cc, and at least 50% of the voxels of the reconstructed three-dimensional intensity image of the ROI have inaccuracies of less than 15% of range R, i.e., less than $1.5 \times 10^4$ photons/second/cc. For some applications, the study produces a parametric image related to a physiological process occurring in each voxel. In one particular embodiment, the image has a resolution of at least 5×5×5 mm, and at least 50% of the voxels have inaccuracies of less than 15% of range R;

the image has a resolution of at least 20×20×20 mm, such as at least 15×15×15 mm, 10×10×10 mm, 7×7×7 mm, 5×5×5 mm, 4×4×4 mm, 4×3×3 mm, or 3×3×3 mm, wherein values of parameters of a physiological process modeled by a parametric representation have a range of physiological parameter values R, and wherein at least 50% of the voxels of the reconstructed parametric three-dimensional image have inaccuracies less than 100% of range R, such as less than 70%, 50%, 40%, 30%, 25%, 20%, 15%, 10%, 5%, 2%, 1%, or 0.5% of range R. For example, the physiological process may include blood flow, the values of the parameters of the physiological process may have a range from 0 to 100 cc/minute, such that the range R is 100 cc/minute, and at least 50% of the voxels of the reconstructed parametric three-dimensional image have inaccuracies less than 25% of range R, i.e., less than 25 cc/minute. In one particular embodiment, the image has a resolution of at least 5×5×5 mm, and at least 50% of the voxels have inaccuracies of less than 25% of range R; and/or the image is generated according to a protocol, including at the radiopharmaceutical dose and image acquisition duration specified by the protocol, and the image has a resolution of at least 7×7×7 mm, such as at least 6×6×6 mm, 5×5×5 mm, 4×4×4 mm, 4×3×3 mm, or 3×3×3 mm, in at least 50% of the reconstructed volume, wherein if the labeled radiopharmaceutical agent is distributed substantially uniformly within a portion of the ROI, which portion has an emission-intensity I+/−10% (which is defined as emitted photons/unit time/volume), and wherein at least 85% of the voxels of the reconstructed three-dimensional emission-intensity image of the portion of the ROI have inaccuracies of less than 30% of intensity I, such as less than 15%, 10%, 5%, 2%, 1%, 0.5%, 20%, or 25% of intensity I. For example, the agent may be distributed within a volume with a uniform emission-intensity I of $10^5$ photons/second/cc, and at least 85% of the voxels of the reconstructed three-dimensional intensity image of the volume have inaccuracies of less than 15% of intensity I, i.e., less than $1.5 \times 10^4$ photons/second/cc. For some applications, the same definition may apply to a study which produces a parametric image related to a physiological process occurring in each voxel. In one particular embodiment, the image has a resolution of at least 5×5×5 mm, and at least 50% of the voxels have inaccuracies of less than 15% of intensity I.

In an embodiment of the present invention, imaging system 10 is configured to modify one or more scan parameters during an imaging procedure. For example, during an early portion of an imaging procedure, the imaging system may acquire relatively low-resolution images, and during a later portion of the procedure, the imaging system may acquire higher-resolution images. For some applications, the system modifies the one or more parameters during the imaging procedure responsively to one or more properties acquired during the procedure. For some applications, techniques are used that are described in above-mentioned International Application PCT/IL2006/001291, which published as PCT Publication WO 2007/054935.

Reference is made to Table 1, which is a table showing human experimental results, measured in accordance with an embodiment of the present invention. This experiment was performed in order to demonstrate, in a clinical setting, the SPECT sensitivity of a novel cardiac scanner similar to SPECT imaging system 10, described hereinabove with reference to FIG. 2. Although this experiment was performed with Tc99m-sestamibi, the inventors believe that similar results would be obtained with teboroxime Tc99m, because sestamibi and teboroxime are both labeled with the same radioisotope, Tc99m.

In this experiment, three adult human volunteers were imaged both with the novel cardiac scanner similar to SPECT imaging system 10 and a conventional gamma camera (Varicam™ gamma camera; General Electric) equipped with a Low Energy High Resolution (LEHR) collimator for comparison of sensitivity. Conventional gamma camera images were acquired using a 180 degree elliptical orbit and 23.4 seconds/stop for 32 stops (mean acquisition time of 12.5 minutes). The imaging with the novel cardiac scanner had an acquisition time of two minutes. Counts/minute in the myocardium for both the novel cardiac scanner and the conventional gamma camera acquisitions were determined by analysis of raw data images on the Xeleris workstation (GE Medical, computer model XW6200, Xeleris ver.1.1324). The calculation of counts from the myocardium was made by summing the number of counts collected from the left ventricle only, and correcting for radioactive decay during the time delay between imaging with the conventional camera and imaging with the novel cardiac scanner. The sensitivity in millions of counts (MC)/minute was calculated by dividing the number of counts from the myocardium by the scan duration in minutes. The sensitivity gain factor was defined as the ratio between the sensitivity of the novel cardiac scanner and that of the conventional gamma camera.

As can be seen in Table 1, the novel cardiac scanner had a sensitivity gain factor in the three subjects ranging from 7.0 to 10.5, for an average sensitivity gain of 8.6. As described hereinabove, such increased sensitivity enables many of the novel protocols and radiopharmaceutical formulations described in the present application.

Figure 8:
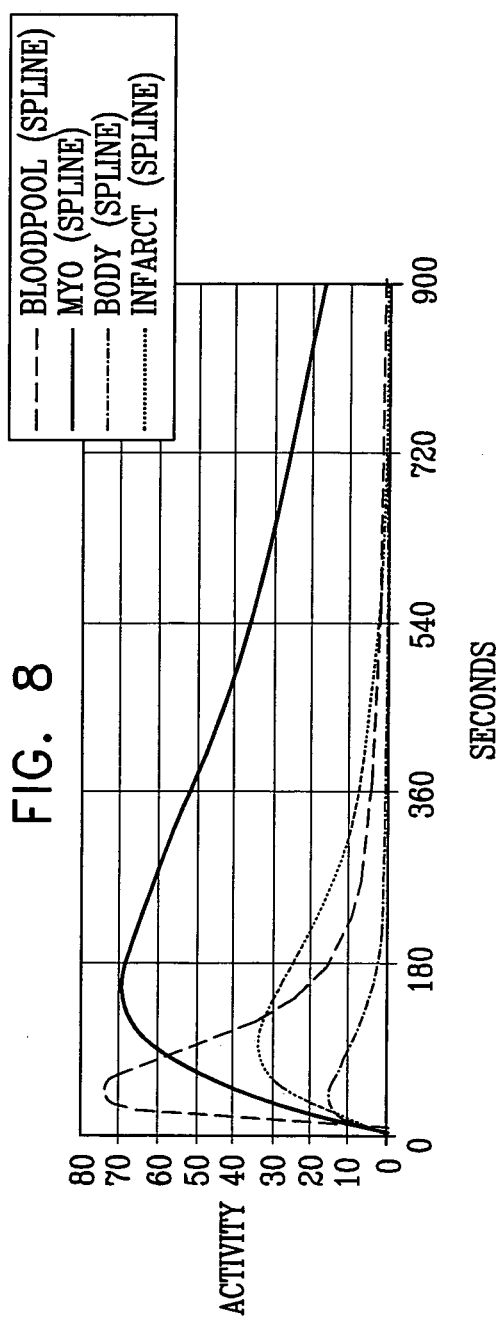
FIG. 8 is a graph showing input curves, in accordance with an embodiment of the present invention.

Reference is made to FIG. 8, which is a graph showing input curves, in accordance with an embodiment of the present invention. These input curves are taken from Reutter et al., "Accuracy and precision of compartmental model parameters obtained from directly estimated dynamic SPECT time-activity curves," 2002 IEEE Nuclear Science Symposium, pp. 1584-1588, which is incorporated herein by reference. The phantom was configured such that the dynamics of the tracer uptake and washout mimicked that of teboroxime, using the input curves shown in FIG. 8.

Figure 9:
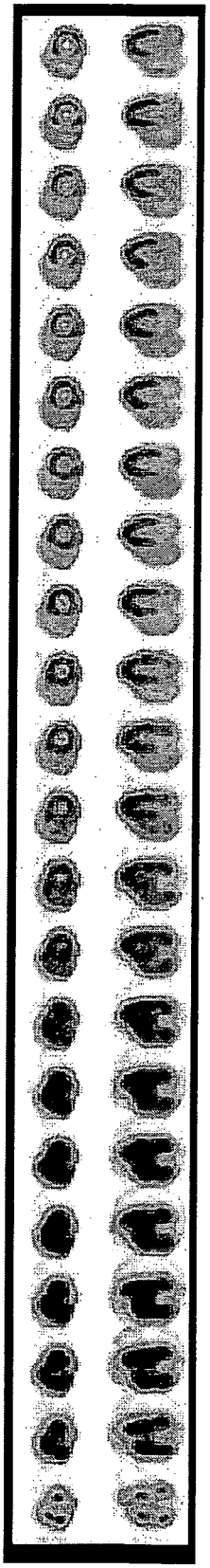
FIG. 9 shows a series of mid-ventricular slice images produced by the simulation during the first four minutes after the simulated teboroxime injection, in accordance with an embodiment of the present invention.

FIG. 9 shows a series of mid-ventricular slice images produced by the simulation during the first four minutes after the simulated teboroxime injection, in accordance with an embodiment of the present invention. Each image represents a single 10-second frame. The upper row of images are short axis (SA) views, while the lower row of images are horizontal long axis (HLA) views. As can be seen in the series of images, the intense blood pool activity at the center of the heart chambers gradually clears while the myocardial uptake gradually intensifies.

Further supporting evidence for the greater sensitivity of embodiments of imaging system 10 compared to conventional SPECT imaging systems is provided in the above-mentioned International Application PCT/IL2005/001173 (see, for example, the Summary of the Invention section thereof).

Low-Dose Teboroxime Kits and Doses

DEFINITIONS

Listed below are definitions of the terms used to describe the $^{99m}$Tc-containing species that constitute part of some embodiments of the present invention. These definitions apply to the terms as they are used throughout the specifica-

TABLE 1

| Dose | Patient 1 28.29 mCi | | Patient 2 23.4 mCi | | Patient 3 26.5 mCi | |
|---|---|---|---|---|---|---|
| Imaging duration (minutes) | 12.5 | 2 | 12.5 | 2 | 12.5 | 2 |
| Total study counts (million counts [MC]) | | | | | | |
| Before decay correction | 17.08 | 2.06 | 16.15 | 1.96 | 14.26 | |
| After decay correction | n/a | 2.68 | n/a | 2.61 | n/a | 2.71 |
| Myocardium counts | | | | | | |
| Before decay correction | 1.70 | 1.46 | 1.43 | 1.37 | 1.18 | |
| After decay correction | n/a | 1.90 | n/a | 1.83 | n/a | 1.98 |
| Myocardium counts % total counts | 9.5% | 71.0% | 8.9% | 71.1% | 8.3% | 73.1% |
| Myocardium sensitivity after decay correction (MC/min) | 0.136 | 0.95 | 0.11 | 0.92 | 0.095 | 0.99 |
| Sensitivity gain factor | 1.0 | 7.0 | 1.0 | 8.4 | 1.0 | 10.5 |

A dynamic study simulation was performed in order to demonstrate the SPECT sensitivity of SPECT imaging system 10, described hereinabove with reference to FIG. 2. A digital NURBS-based Cardiac-Torso (NCAT) phantom having internal organs was used. The dimensions of the internal organs are based on CT information from a real patient, such that the phantom is realistic. The simulation modeled an injected dose of 22.5 mCi of teboroxime. The total scan time was 4 minutes, which included 24 10-second frames. The number of counts measured in the left ventricle at the time of maximal uptake during a 10-second frame was calculated to be 280,000 photons.

tion (unless they are otherwise limited in specific instances) either individually or as part of a larger group.

The terms "alkyl" and "alkoxy" refer to both straight and branched chain groups, e.g. methyl, ethyl, propyl, isopropyl, n-butyl, sec-butyl, isobutyl, t-butyl, straight and branched pentyl, straight and branched hexyl, straight and branched heptyl, straight and branched octyl, straight and branched nonyl, and straight and branched decyl, as well as the alkoxy analogues thereof.

The term "alkenyl" refers to both straight and branched chain groups having one or more double bonds, e.g. ethenyl, propenyl, 1-, 2- and 3-butenyl, straight and branched pentenyl, straight and branched hexenyl, straight and branched heptenyl, straight and branched octenyl, straight and branched nonenyl, and straight and branched decenyl.

The term "aryl" refers to phenyl and substituted phenyl, such as phenyl substituted with 1, 2 or 3 alkyl, haloalkyl, aminoalkyl, alkylaminoalkyl, dialkylaminoalkyl, alkoxy, alkoxyalkyl, halogen, amino, hydroxy, or formyl groups. Additional exemplary aryl groups for the instance wherein $R_3$ is aryl include 3-(5-dimethylamino-1-naphthalenesulfonylamino)phenyl, 3-[4-[3'-phenyl-2'-pyrazolin-1,1'-yl]benzenesulfonyl-amino]phenyl, 3-(pyrenesulfamido)phenyl, 3-[4-(4-dimethylamino-1-naphthylazo)-3-(methoxyphenylsulfamido)]phenyl, and 3-[4-(4-dimethylamino-1-phenylazo) phenylthioureido]phenyl.

"Cycloalkyl" and "cycloalkenyl" groups include those having 5, 6 or 7 carbon atoms. The terms include those groups substituted with alkyl, alkoxy, aryl, carboxyalkyl, arylalkyl or $(R_4R_5N)$-alkyl groups.

The terms "halide", "halo" and "halogen" refer to fluorine, chlorine, bromine and iodine.

The expression "5 or 6-membered nitrogen containing heterocycle" refers to all 5 and 6-membered rings containing at least one nitrogen atom. Exemplary aliphatic groups are dehydro derivatives of a compound having the formula

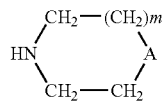

wherein m is 0 or 1 and A is O, N—$R_6$ or CH—$R_6$ wherein $R_6$ is hydrogen, alkyl, aryl or arylalkyl. Such groups include pyrrolidinyl, piperidinyl, morpholinyl, piperazinyl, 4-alkylpiperazinyl, 4-alkylpiperidinyl, and 3-alkylpyrrolidinyl groups. Also included within the expression "5 or 6-membered nitrogen containing heterocycle" are aromatic groups. Exemplary aromatic groups are pyrrolyl, imidazolyl, oxazolyl, pyrazolyl, pyridinyl, and pyrimidinyl groups. The above groups can be linked via a hetero atom or a carbon atom.

The expression "5 or 6-membered nitrogen or oxygen containing heterocycle" refers to all 5 and 6-membered rings containing at least one nitrogen or oxygen atom. Exemplary groups are those described above under the definition of the expression "5 or 6-membered nitrogen containing heterocycle". Additional exemplary groups are 1,4-dioxanyl and furanyl.

In an embodiment of the present invention, a kit or a container containing a dose of a radiolabeled radiopharmaceutical agent comprises a 99m-BATO species having a radioactivity of less than 5 mCi, such as less than or equal to 4.5 mCi, less than or equal to 4 mCi, or less than or equal to 3 mCi, e.g., between 2 and 3 mCi. Imaging system 10 is able to produce clinically-valuable images using this kit or radiolabeled radiopharmaceutical agent. For some applications, the ingredients for making the 99m-BATO species, other than $^{99m}$Tc, are contained in a first container, and the technetium Tc-99m is contained in a second container. For other applications, a dose of the 99m-BATO species is prepared from the ingredients and the technetium Tc-99m having the above-mentioned radioactivity. For example, automated radiopharmaceutical dispensing system 52, described hereinabove with reference to FIG. 5, may prepare a dose of teboroxime Tc-99m from the ingredients and technetium Tc-99m stored in radiolabeled mother vial 104. For some applications, such a dose is stored together with additional doses in a single container, either in a same chamber of the container, or in separate chambers of the container.

For some applications, in order to achieved a desired radioactivity at the time of administration, the teboroxime or other 99m-BATO species is dispensed with an initial radioactivity that is greater than the desired radioactivity at the time of administration. Such initial radioactivity is calculated based on the known half-life of the Tc-99m and an estimate of the time of administration. Such calculation is typically performed by an automated dispensing system (e.g., dispensing system 52), a radiopharmaceutical pharmacy system, or a pharmacist.

The technetium Tc-99m is typically in physiological saline.

In an embodiment of the present invention, the kit for making the 99m-BATO species comprises the following lyophilized ingredients:
an anion source;
a boronic acid derivative, or compounds which can react in situ to form a boronic acid derivative, having the formula

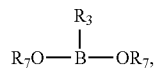

or a pharmaceutically acceptable salt thereof, wherein $R_3$ is hydroxy, alkyl, alkenyl, cycloalkyl, cycloalkenyl, alkoxy, carboxyalkyl, carboxyalkenyl, hydroxyalkyl, hydroxalkenyl, alkoxyalkyl, alkoxy-alkenyl, haloalkyl, haloalkenyl, aryl, arylalkyl, or $R_4R_5N$-alkyl and $R_4$ and $R_5$ are each independently hydrogen, alkyl, or arylalkyl, or $R_4$ and $R_5$ when taken together with nitrogen atom to which they are attached form a 5 or 6-membered nitrogen containing heterocycle, and $R_7$ is hydrogen, alkyl or aryl; and
at least one dioxime having the formula

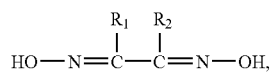

or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_1$ and $R_2$ are —$(CR_8R_9)_n$— wherein n is 3, 4, 5, or 6 and $R_8$ and $R_9$ are each independently hydrogen or alkyl;

In some embodiments, the kit contains a reducing agent, such as stannous chloride or stannous fluoride. In some embodiments, the kit contains a pharmaceutically acceptable complexing agent (also sometimes referred to as a chelating agent). Examples of complexing agents are diethylenetriamine-pentaacetic acid (DTPA, also known as pentetic acid), ethylene glycol-bis(β-aminoethyl ether)-N,N'-tetraacetic acid (EGTA), ethylenediamine tetraacetic acid (EDTA), citric acid, tartaric acid, malonic acid, etc. In some embodiments, the kit contains an accelerator (catalyst) which serves to improve the radiochemical purity (i.e., percent of the radioactivity that is in the desired chemical form) of the product. Examples of accelerators are the α-hydroxycarboxylic acids such as citric acid, tartaric acid, and malonic acid.

Thus, in an embodiment of the present invention, the kit for making the 99m-BATO species comprises the following lyophilized ingredients:

5 to 15 mg sodium chloride, or sodium bromide;
1 to 3 mg of boronic acid derivative, or compounds which can react in situ to form a boronic acid derivative, having the formula

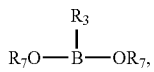

or a pharmaceutically acceptable salt thereof, wherein $R_3$ is hydroxy, alkyl, alkenyl, cycloalkyl, cycloalkenyl, alkoxy, carboxyalkyl, carboxyalkenyl, hydroxyalkyl, hydroxalkenyl, alkoxyalkyl, alkoxyalkenyl, haloalkyl, haloalkenyl, aryl, arylalkyl, or $R_4R_5N$-alkyl and $R_4$ and $R_5$ are each independently hydrogen, alkyl, or arylalkyl, or $R_4$ and $R_5$ when taken together with nitrogen atom to which they are attached form a 5 or 6-membered nitrogen containing heterocycle, and $R_7$ is hydrogen, alkyl or aryl;
1 to 3 mg of at least one dioxime having the formula

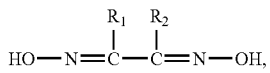

or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_1$ and $R_2$ are $-(CR_8R_9)_n-$ wherein n is 3, 4, 5, or 6 and $R_8$ and $R_9$ are each independently hydrogen or alkyl;
0.03 to 0.06 mg stannous chloride;
1 to 3 mg pentetic acid; and
8 to 10 mg citric acid.

In an embodiment of the present invention, the kit comprises the following lyophilized ingredients:
1 to 3 mg cyclohexanedione dioxime;
1 to 3 mg methyl boronic acid;
1 to 3 mg pentetic acid;
8 to 10 mg citric acid;
5 to 10 mg sodium chloride; and
0.030 to 0.060 mg stannous chloride ($SnCl_2$); and For some applications, the kit additionally comprises 30 to 50 mg hydroxypropyl gamma cyclodextrin, which is typically contained in the container containing the non-technetium ingredients.

For some applications, the dioxime is selected from the group consisting of:
dimethyl glyoxime,
1,2-cyclohexanedione dioxime,
1,2-ethanedione dioxime,
α-furyldioxime,
1,2-cyclopentanedione dioxime, and
3-methyl-1,2-cyclopentanedione dioxime.

For some applications, two or three different dioximes are used.

For some applications, the boronic acid derivative is selected from the group consisting of:
B-alkyl,
B-alkoxy,
B-benzyl and
B-cycloalkyl.

For some applications, the technetium Tc-99m, when added to the other ingredients, forms a complex therewith, said complex selected from the group consisting of:

$^{99m}$Tc (chlorine) (dimethyl glyoxime)$_3$ methoxy boron;
$^{99m}$Tc (chlorine) (dimethyl glyoxime)$_3$ hydroxy boron;
$^{99m}$Tc (chlorine) (dimethyl glyoxime)$_3$ ethoxy boron;
$^{99m}$Tc (chlorine) (dimethyl glyoxime)$_3$ propyloxy boron;
$^{99m}$Tc (chlorine) (dimethyl glyoxime)$_3$ hexyloxy boron;
$^{99m}$Tc (chlorine) (dimethyl glyoxime)$_3$ 1-methylpropyl boron;
$^{99m}$Tc (bromine) (dimethyl glyoxime)$_3$ butyl boron;
$^{99m}$Tc (iodine) (dimethyl glyoxime)$_3$ butyl boron;
$^{99m}$Tc (fluorine) (dimethyl glyoxime)$_3$ butyl boron;
$^{99m}$Tc (chlorine) (dimethyl glyoxime)$_3$ 3-(4-morpholinyl) propyl boron;
$^{99m}$Tc (chlorine) (dimethyl glyoxime)$_3$ 2-phenylethyl boron;
$^{99m}$Tc (chlorine) (1,2-cyclohexanedione dioxime)$_3$ methyl boron; and
$^{99m}$Tc (chlorine) (dimethyl glyoxime)$_3$ 4-formylphenyl boron.

In an embodiment of the present invention, a boronic acid adduct of technetium-99m dioxime complexes is provided, having the formula

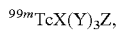

wherein
X is an anion;
Y, which in each instance is independently chosen, is a vicinal dioxime having the formula

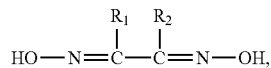

or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_1$ and $R_2$ are $-(CR_8R_9)_n-$ wherein n is 3, 4, 5 or 6 and $R_8$ and $R_9$ are each independently hydrogen or alkyl; and
Z is a boron derivative of the formula

wherein $R_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or ($R_4R_5N$)-alkyl and $R_4$ and $R_5$ are each independently hydrogen, alkyl, or arylalkyl, or $R_4$ and $R_5$ when taken together with the nitrogen atom to which they are attached form a 5 or 6-membered nitrogen containing heterocycle, and wherein the $^{99m}$Tc has a radioactivity of less than 5 mCi. In those embodiments of the present invention which are pharmaceutical or diagnostic compositions, the compositions comprise a complex of the formula $^{99m}$TcX(Y)$_3$Z as defined above, wherein the total amount of $^{99m}$Tc radioactivity present in that portion of the formulation which is to be administered to a patient is less than 5 mCi.

For some applications, X is a halide.
For some applications, X is chloride or bromide.
For some applications, X is chloride.
For some applications, Y is dimethyl glyoxime, 1,2-cyclohexanedione dioxime, 1,2-ethanedione dioxime, α-furyldioxime, 1,2-cyclopentanedione dioxime, or 3-methyl-1,2-cyclopentanedione dioxime.
For some applications, Y is dimethyl glyoxime
For some applications, Y is 1,2-cyclohexanedione dioxime.

For some applications, Y is 1,2-ethanedione dioxime.

For some applications, Y is α-furyldioxime.

In some applications, the BATO species contains two or three different dioximes Y.

For some applications, the boron derivative Z is B-alkyl.

For some applications, the boron derivative Z is B-alkoxy.

For some applications, the boron derivative Z is B-benzyl.

For some applications, the boron derivative Z is B-cycloalkyl.

For some applications, the boronic acid adduct is $^{99m}$Tc (chlorine)(1,2-cyclohexanedione dioxime)$_3$ methyl boron.

For some applications, the boronic acid adduct is $^{99m}$Tc (chlorine)(dimethylglyoxime)$_3$ 1-methylpropyl boron.

For some applications, the boronic acid adduct is $^{99m}$Tc (chlorine)(dimethylglyoxime)$_3$ 4-methylphenyl boron.

For some applications, the boronic acid adduct is $^{99m}$Tc (chlorine)(dimethyl glyoxime)$_3$ cyclopentyl boron.

For some applications, the boronic acid adduct is $^{99m}$Tc (chlorine) 1,2-cyclohexanedione dioxime)$_3$ ethyl boron.

For some applications, the boronic acid adduct is $^{99m}$Tc (chlorine)(dimethyl glyoxime)$_3$ 4-(t-butyl)phenyl boron.

For some applications, the boronic acid adduct is $^{99m}$Tc (chlorine) (dimethyl glyoxime)$_3$ 2-methyl-1-propyl boron.

For some applications, the boronic acid adduct is $^{99m}$Tc (chlorine) (1,2-cyclohexanedione dioxime)$_3$ hydroxy boron.

In an embodiment of the present invention, a method comprises producing any of the above-mentioned 99m-BATO species. For some applications, producing the 99m-BATO species comprises producing the species using an automated radiopharmaceutical dispensing system, such as dispensing system 52, described hereinabove with reference to FIG. 5.

Preparation of the complexes in accordance with embodiments of this invention can best be accomplished using technetium-99m in the form of the pertechnetate ion. The pertechnetate ion can be obtained from commercially available technetium-99m parent-daughter generators; such technetium is in the +7 oxidation state. The generation of the pertechnetate ion using this type of generator is well known in the art, and is described in more detail in U.S. Pat. Nos. 3,369,121 and 3,920,995, the contents of which are incorporated herein by reference. These generators are usually eluted with saline solution and the pertechnetate ion is obtained as the sodium salt.

To prepare the complexes, pertechnetate ion (in the form of a salt) is combined with a source of anion, a boronic acid derivative having the formula $R_3B(OR_7)(OR_7)$ (IV) or a pharmaceutically acceptable salt thereof, wherein $R_7$ is in each instance independently hydrogen, alkyl or aryl, and a dioxime having the formula $HON=CR_1CR_2=NOH$ (II) or a pharmaceutically acceptable salt thereof.

It is possible, in some instances, to prepare a boronic acid derivative of formula IV in situ. For example, when preparing a complex having an alkoxy group attached to the boron atom, it is possible to utilize boric acid and the appropriate alkanol as reactants.

The source of the anion moiety (X) can be water or it can be an acid or salt which dissociates to release an appropriate anion. Exemplary anionic moieties are hydroxyl, halide, isothiocyanato ($N=C=S^{(-)}$) and thiocyanato ($S—C=N^{(-)}$). If the source of the anion is not water, the source should be present in an appropriate concentration to compete effectively with any water that may be present during the reaction. It has been reported that the source of anion should be present in the reaction mixture in a concentration of about 0.3 to 4.5 molar.

The boronic acid derivative of formula IV may be present in a concentration of, e.g., about 5 to 200 millimolar. The dioxime of formula II may be present in a concentration of, e.g., about 9 to 43 millimolar.

The formation of the complex proceeds best if the mixture of pertechnetate ion, source of anion, boronic acid derivative, and dioxime is heated at about 25° C. to 150° C. for about 5 minutes to about 60 minutes, preferably at about 100° C. to about 140° C. for about 5 minutes to about 15 minutes. The reaction is preferably run in an aqueous medium at a pH of less than, or equal to, about 5.

The reaction mixture should also contain a reducing agent. Stannous ion is the preferred reducing agent, and can be introduced in the form of a stannous salt such as a stannous halide (e.g., stannous chloride or stannous fluoride). The reducing agent should be present in a concentration of about 1.5 micromolar to 6.6 millimolar.

Various pharmaceutically acceptable complexing agents (also known in the art as chelating agents) can be included as part of the complexing reaction. Exemplary complexing agents are diethylenetriamine-pentaacetic acid (DTPA, also known as pentetic acid), ethylene glycol-bis(β-aminoethyl ether)-N,N'-tetraacetic acid (EGTA), ethylenediamine tetraacetic acid (EDTA), citric acid, tartaric acid, malonic acid, etc.

The complexing reaction mixture can also include an accelerator (catalyst) which serves to improve the radiochemical purity (i.e., percent of the radioactivity that is in the desired chemical form) of the product. Exemplary accelerators are the α-hydroxycarboxylic acids such as citric acid, tartaric acid, and malonic acid. A combination of DTPA and citric acid has been found to be preferred.

In some embodiments of the invention, the $^{99m}$Tc-containing species may be administered in conjunction with a hydroxypropyl gamma cyclodextrin, e.g. 2-hydroxypropyl gamma cyclodextrin, in accordance with what is disclosed in U.S. Pat. No. 6,056,941, the contents of which are incorporated herein by reference.

Working with the technetium-99 isotope, the structure of the complexes formed has been investigated and has been reported to be:

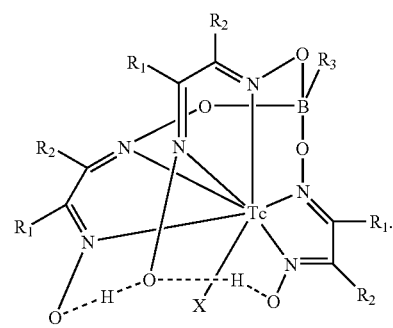

Because of the short half-life of technetium-99m (i.e., 6.02 hours), it is generally necessary to prepare the complexes in accordance with embodiments this invention at, or near, the site where they are to be used. A kit having all of the components, other than the pertechnetate ion, needed to prepare the boronic adducts of technetium-99m dioxime complexes of formula I is provided in accordance with embodiments of this invention. Such a kit contains a source of anion, a boronic acid derivative of formula IV (or compounds which can react in situ to form such a derivative), or a pharmaceutically acceptable salt thereof, a dioxime of formula II, or a pharmaceutically acceptable salt thereof, and a reducing agent. It may optionally contain a complexing agent.

Such kits can be formulated in aqueous solution. To optimize the stability of the kit, and to optimize the radiochemical purity of the labeled product, the pH of the kit should be adjusted to fall within the range of about 2.0 to 5.5, e.g. 3.0, using a pharmaceutically acceptable acid or base (e.g., hydrochloric acid or sodium hydroxide). In some embodiments, the ingredients in the kit will be in lyophilized form.

The 99m-BATO complexes ($^{99m}$Tc-containing species) in accordance with embodiments of this invention are useful as imaging agents. More specifically, they are useful for imaging the myocardium and the hepatobiliary system in humans and other mammalian hosts. Those complexes which are neutral at physiological pH (i.e., pH 7.4) are also useful for imaging the brain in humans and other mammalian hosts. [The charge of the complexes is determined by the sum of the charges of the organic groups ("$R_1$", "$R_2$" and "$R_3$") attached to the boron atom and part of the dioximes.] Those complexes which contain the vicinal dioxime 1,2-ethanedione dioxime are also useful for imaging the blood pool of humans and other mammalian hosts.

The complexes of this invention can be administered to a host by bolus intravenous injection. The size of the host, and the imaging system used, will determine the quantity of radioactivity needed to produce diagnostic images. For a human host, the quantity of radioactivity injected will normally range from about 5 to 20 millicuries of technetium-99m.

The following examples are specific embodiments of $^{99m}$Tc-containing species that may be used in accordance with embodiments of the present invention.

EXAMPLE 1

$^{99m}$Tc (chlorine)(dimethyl glyoxime)$_3$ methoxy boron and $^{99m}$Tc (chlorine)(dimethyl glyoxime)$_3$ hydroxy boron Into a 5 ml siliconized serum vial are measured 5.0 mg of dimethyl glyoxime, 0.5 ml of methanol, 2.0 mg of boric acid and 0.5 mg of stannous chloride in 5 μl of concentrated hydrochloric acid.

Sodium pertechnetate* in physiological saline (0.2 ml) is added to the vial which is then heated at 140° C. for 30 minutes yielding 6%** of the $^{99m}$Tc (chlorine)(dimethyl glyoxime)$_3$ methoxy boron as determined by HPLC (high pressure liquid chromatography). The reaction also yields $^{99m}$Tc (chlorine)(dimethyl glyoxime)$_3$ hydroxy boron. The complexes are separated by HPLC.

EXAMPLE 2

$^{99m}$Tc (chlorine)(dimethyl glyoxime)$_3$ ethoxy boron and $^{99m}$Tc (chlorine)(dimethyl glyoxime)$_3$ hydroxy boron Into a 5 ml siliconized vial are measured 2.0 mg of dimethyl glyoxime in 0.2 ml of ethanol, 2.0 mg of boric acid, 10 mg of citric acid in 0.1 ml of water, 100 mg of sodium chloride, 1.0 mg of diethylenetetramine pentaacetic acid, and approximately 50-60 μg of anhydrous stannous chloride in 1 μl of concentrated hydrochloric acid.

Sodium pertechnetate in physiological saline (0.5 ml) is added to the vial which is then heated at 100° C. for 5 minutes yielding 4-5% of $^{99m}$Tc (chlorine)(dimethyl glyoxime)$_3$ ethoxy boron. The reaction also yields $^{99m}$Tc (chlorine)(dimethyl glyoxime)$_3$ hydroxy boron. The complexes are separated by HPLC.

EXAMPLE 3

$^{99m}$Tc (chlorine)(dimethyl glyoxime)$_3$ propyloxy boron and 99 mTc (chlorine)(dimethyl glyoxime)$_3$-hydroxy boron Following the procedure of example 1, but substituting n-propanol for methanol, yields $^{99m}$Tc (chlorine)(dimethyl glyoxime)$_3$ ethoxy boron. The reaction also yields $^{99m}$Tc (chlorine)(dimethyl glyoxime)$_3$ hydroxy boron. The complexes are separated by HPLC.

EXAMPLE 4

$^{99m}$Tc (chlorine)(dimethyl glyoxime)$_3$ butyloxy boron and $^{99m}$Tc (chlorine)(dimethyl glyoxime)$_3$ hydroxy boron Following the procedure of example 1, but substituting n-butanol for methanol, yields 6% of $^{99m}$Tc (chlorine)(dimethyl glyoxime)$_3$ butyloxy boron. The reaction also yields $^{99m}$Tc (chlorine)(dimethyl glyoxime)$_3$ hydroxy boron. The complexes are separated by HPLC.

EXAMPLE 5

$^{99m}$Tc (chlorine)(dimethyl glyoxime)$_3$ pentyloxy boron and $^{99m}$Tc (chlorine)(dimethyl glyoxime)$_3$ hydroxy boron Following the procedure of example 1, but substituting n-pentanol for methanol, yields $^{99m}$Tc (chlorine)(dimethyl glyoxime)$_3$ pentyloxy boron. The reaction also yields $^{99m}$Tc (chlorine)(dimethyl glyoxime)$_3$ hydroxy boron. The complexes are separated by HPLC.

EXAMPLE 6

$^{99m}$Tc (chlorine)(dimethyl glyoxime)$_3$ hexyloxy boron and $^{99m}$Tc (chlorine)(dimethyl glyoxime)$_3$ hydroxy boron Following the procedure of example 1, but substituting n-hexanol for methanol, yields 8% of $^{99m}$Tc (chlorine)(dimethyl glyoxime)$_3$ hexyloxy boron. The reaction also yields $^{99m}$Tc (chlorine)(dimethyl glyoxime)$_3$ hydroxy boron. The complexes are separated by HPLC.

EXAMPLE 7

$^{99m}$Tc (chlorine)(dimethyl glyoxime)$_3$ octyloxy boron and $^{99m}$Tc (chlorine)(dimethyl glyoxime)$_3$ hydroxy boron Following the procedure of example 1, but substituting n-octanol for methanol, yields 12% $^{99m}$Tc (chlorine)(dimethyl glyoxime)$_3$ octyloxy boron. The reaction also yields 99 mTc (chlorine)(dimethyl glyoxime)$_3$ hydroxy boron. The complexes are separated by HPLC.

EXAMPLE 8

$^{99m}$Tc (chlorine)(dimethyl glyoxime)$_3$ 1-methylpropyl boron

Following the procedure of example 2, but substituting 1-methylpropane boronic acid for boric acid, yields the title complex.

EXAMPLE 9

$^{99m}$Tc (chlorine)(dimethyl glyoxime)$_3$ methyl boron

Into a 5 ml siliconized serum vial are measured 2.0 mg of dimethyl glyoxime in 0.2 ml of ethanol, 2.0 mg of methane boronic acid, 10 mg of citric acid in 0.1 ml of water, 100 mg of sodium chloride, 1.0 mg of diethylenetetramine pentaacetic acid, and about 50-60 µg of stannous chloride in 1 µl of concentrated hydrochloric acid.

Sodium pertechnetate in physiological saline (0.5 ml) is added to the vial which is heated at 100° C. for 5 minutes yielding 80-90% of the title complex.

EXAMPLE 10

$^{99m}$Tc (chlorine)(dimethyl glyoxime)$_3$ propyl boron

Following the procedure of example 9, but substituting 1-propane boronic acid for methane boronic acid, yields the title complex.

EXAMPLE 11

$^{99m}$Tc (chlorine)(dimethyl glyoxime)$_3$ butyl boron

Following the procedure of example 9, but substituting 1-butane boronic acid for methane boronic acid, yields the title complex.

EXAMPLE 12

$^{99m}$Tc (chlorine)(dimethyl glyoxime)$_3$ pentyl boron

Following the procedure of example 9, but substituting 1-pentane boronic acid for methane boronic acid, yields 85% of the title complex.

EXAMPLE 13

$^{99m}$Tc (chlorine)(dimethyl glyoxime)$_3$ hexyl boron

Into a 5 ml siliconized serum vial are measured 3.0 mg of dimethyl glyoxime, 20 mg of 1-hexane boronic acid, sodium pertechnetate in physiological saline (0.2 ml) and 50 µl of saturated aqueous stannous tartrate. The vial is heated at 140° C. for 5 minutes yielding 16% of the title complex.

EXAMPLE 14

$^{99m}$Tc (chlorine)(dimethyl glyoxime)$_3$ heptyl boron

Following the procedure of example 9, but substituting 8.0 mg of 1-heptane boronic acid for methane boronic acid and substituting 50 µl of saturated aqueous stannous tartrate for stannous chloride in hydrochloric acid, yields 85% of the title complex.

EXAMPLE 15

$^{99m}$Tc (chlorine)(dimethyl glyoxime)$_3$ phenyl boron

Following the procedure of example 2, but substituting benzene boronic acid for boric acid, yields 88% of the title complex.

EXAMPLE 16

$^{99m}$Tc (chlorine)(dimethyl glyoxime)$_3$ butyl boron

Into a 5 ml siliconized serum vial are measured 1.0 mg of dimethyl glyoxime in 0.1 ml of ethanol, 5.0 mg of 1-butane boronic acid in 50 µl of ethanol, 0.3 ml of saturated aqueous sodium chloride and 25 µl of saturated stannous pyrophosphate.

Sodium pertechnetate in physiological saline (0.1 ml) is added to the vial which is heated at 140° C. for 5 minutes yielding 70% of the title complex.

EXAMPLE 17

$^{99m}$Tc (bromine)(dimethyl glyoxime)$_3$ butyl boron

Into a 5 ml siliconized serum vial are measured 1.0 mg of dimethyl glyoxime in 0.1 ml of ethanol, 5.0 mg of 1-butane boronic acid in 50 µl of ethanol, 0.3 ml of saturated aqueous potassium bromide, and 25 µl of saturated aqueous stannous pyrophosphate.

Sodium pertechnetate in physiological saline (0.1 ml) is added to the vial which is heated at 140° C. for 5 minutes yielding 59% of the title complex.

EXAMPLE 18

$^{99m}$Tc (iodine)(dimethyl glyoxime)$_3$ butyl boron

Into a 5 ml siliconized serum vial are measured 1.0 mg of dimethyl glyoxime in 0.1 ml of ethanol, 5.0 mg of 1-butane boronic acid in 50 µl of ethanol, 0.3 ml of saturated aqueous potassium iodide, 25 µl of saturated aqueous stannous pyrophosphate.

Sodium pertechnetate in physiological saline (0.1 ml) is added to the vial which is heated at 140° C. for 5 minutes yielding 23% of the title complex.

EXAMPLE 19

$^{99m}$Tc (fluorine)(dimethyl glyoxime)$_3$ butyl boron

Into a 5 ml siliconized serum vial are measured 1.0 mg of dimethyl glyoxime in 0.1 ml of ethanol, 5.0 mg 1-butane boronic acid in 50 µl of ethanol, 0.3 ml of saturated aqueous sodium fluoride, and 25 µl of saturated aqeuous stannous pyrophosphate.

Sodium pertechnetate in physiological saline (0.2 ml) is added to the vial which is heated at 140° C. for 5 minutes yielding 0.6% of the title complex.

EXAMPLE 20

$^{99m}$Tc (chlorine)(dimethyl glyoxime)$_3$
3-aminophenyl boron

Into a 5 ml siliconized serum vial are measured 5.0 mg of dimethyl glyoxime in methanol, 30 mg of 3-aminobenzene boronic acid, and 0.5 mg of stannous chloride in 5 µl of concentrated hydrochloric acid.

Sodium pertechnetate in physiological saline (0.2 ml) is added to the vial which is heated at 140° C. for 5 minutes yielding 50% of the title complex.

EXAMPLE 21

$^{99m}$Tc (chlorine)(dimethyl glyoxime)$_3$
4-methylphenyl boron

Following the procedure of example 2, but substituting p-toluene boronic acid for boric acid, yields 88% of the title complex.

EXAMPLE 22

$^{99m}$Tc (chlorine)(dimethyl glyoxime)$_3$
3-(1-piperidinyl)propyl boron

Into a 5 ml siliconized serum vial are measured 0.5 mg of dimethyl glyoxime in 0.1 ml of ethanol 1.0 mg of 3-(1-piperidinyl)propane boronic acid monohydrochloride, 0.2 ml of saturated sodium chloride, 10 mg of citric acid, and 50 µl of saturated aqueous stannous pyrophosphate.

Sodium pertechnetate in physiological saline (0.2 ml) is added to the vial which is heated at 100° C. for 5 minutes yielding 75% of the title complex.

EXAMPLE 23

$^{99m}$Tc (bromine)(dimethyl glyoxime)$_3$
3-(1-piperidinyl)propyl boron

Into a 5 ml siliconized serum vial are measured 1.0 mg of dimethyl glyoxime in 0.1 ml of ethanol, 5.0 mg of 3-(1-piperidinyl)propane boronic acid monohydrochloride, 0.4 ml of saturated potassium bromide, 10 mg of citric acid, and 50 µl of saturated aqueous stannous pyrophosphate.

Sodium pertechnetate in physiological saline (0.2 ml) is added to the vial which is heated at 100° C. for 5 minutes yielding 13.8% of the title complex.

EXAMPLE 24

$^{99m}$Tc (chlorine)(dimethyl glyoxime)$_3$
3-(4-methyl-1-piperidinyl)propyl boron Following the procedure of example 23, but substituting 0.2 ml of saturated sodium chloride for potassium bromide and 5.0 mg of 3-(4-methyl-1-piperidinyl)propane boronic acid monohydrochloride for 3-(1-piperidinyl)propane boronic acid monohydrochloride, yields 94% of the title complex.

EXAMPLE 25

$^{99m}$Tc (chlorine)(dimethyl glyoxime)$_3$
3-(4-morpholinyl)propyl boron

Following the procedure of example 23, but substituting 0.2 ml of saturated sodium chloride for potassium bromide and 5.0 mg of 3-(4-morpholinyl)propane boronic acid monohydrochloride for 3-(1-piperidinyl) propane boronic acid monohydrochloride, yields 87% of the title complex.

EXAMPLE 26

$^{99m}$Tc (chlorine)(dimethyl glyoxime)$_3$
3-(4-benzylpiperidinyl) propyl boron Following the procedure of example 23, but substituting 0.2 ml of saturated sodium chloride for potassium bromide and 5.0 mg of 3-(4-benzyl-1-piperidinyl) propane boronic acid monohydrochloride for 3-(1-piperidinyl) propane boronic acid monohydrochloride, yields the title complex.

EXAMPLE 27

$^{99m}$Tc (chlorine)(dimethyl glyoxime)$_3$ 3-(5-dimethylamino-1-naphthalenesulfonylamino)phenyl boron Following the procedure of example 23, but substituting 0.2 ml of saturated sodium chloride for potassium bromide and 5.0 mg of 3-(5-dimethylamino-1-naphthalenesulfonylamino) benzene boronic acid monohydrochloride for 3-(1-piperidinyl) propane boronic acid monohydrochloride, yields the title complex.

EXAMPLE 28

$^{99m}$Tc (chlorine) (dimethyl glyoxime)$_3$
3-[methyl(2-phenylethyl)amino]propyl boron Following the procedure of example 23, but substituting 0.2 ml of saturated sodium chloride for potassium bromide and 5.0 mg of 3-(methyl(2-phenylethyl)amino) propane boronic acid for 3-(1-piperidinyl) propane boronic acid monohydrochloride, yields the title complex.

EXAMPLE 29

$^{99m}$Tc (chlorine)(dimethyl glyoxime)$_3$
4-hydroxy-1-butenyl boron

Following the procedure of example 2, but substituting 4-hydroxy-1-butene boronic acid for boric acid, yields the title compound.

EXAMPLE 30

$^{99m}$Tc (chlorine)(dimethyl glyoxime)$_3$
(4-benzyl-1-piperidinyl) boron

Following the procedure of example 22, but substituting 5 mg of (4-benzyl-1-piperidinyl) boronic acid monohydrochloride for 3-(1-piperidinyl) propane boronic acid monohydrochloride yields 83% of the title complex.

EXAMPLE 31

$^{99m}$Tc (chlorine)(dimethyl glyoxime)$_3$ 4-(bromomethyl)phenyl boron and $^{99m}$Tc (chlorine)(dimethyl glyoxime)$_3$ 4-(ethoxymethyl)phenyl boron Following the procedure of example 22, but substituting 1 mg of 4-(bromomethyl)benzene boronic acid for 3-(1-piperidinyl)propane boronic acid, monohydrochloride, yields less than 5% of $^{99m}$Tc (chlorine)(dimethyl glyoxime)$_3$ 4-(bromomethyl)phenyl boron. The reaction also yields $^{99m}$Tc (chlorine) (dimethyl glyoxime)$_3$ 4-(ethoxymethyl)phenyl boron. The complexes are separated by HPLC.

EXAMPLE 32

$^{99m}$Tc (chlorine)(dimethyl glyoxime)$_3$ 2-phenylethyl boron

Following the procedure of example 2, but substituting 2-phenylethane boronic acid for boric acid, yields the title complex.

EXAMPLE 33

$^{99m}$Tc (chlorine)(dimethyl glyoxime)$_3$ 4-(methoxymethyl)phenyl boron

Following the procedure of example 22, but substituting 1 mg of 4-(bromomethyl)benzene boronic acid for 3-(1-piperidinyl)propane boronic acid monohydrochloride and methanol for ethanol, yields the title complex.

EXAMPLE 34

$^{99m}$Tc (chlorine)(dimethyl glyoxime)$_3$ 4-(butyloxymethyl)phenyl boron

Following the procedure of example 22, but substituting 1 mg of 4-(bromomethyl)benzene boronic acid for 3-(1-piperidinyl)propane boronic acid monohydrochloride and butanol for ethanol, yields the title complex.

EXAMPLE 35

$^{99m}$Tc (chlorine)(1,2-cycloheptanedione dioxime)$_3$ methyl boron

Following the procedure of example 9, but substituting 1,2-cycloheptenedione dioxime for dimethyl glyoxime, yields 92% of the title complex.

EXAMPLE 36

$^{99m}$Tc (chlorine)(dimethyl glyoxime)$_3$ 4-[(diethylamino) methyl]phenyl boron Following the procedure of example 2, but substituting 4-(aminomethyl)benzene boronic acid monohydrochloride for boric acid, and adding 2.0 mg of diethylenetriamine pentacetic acid yields 77% of the title complex.

EXAMPLE 37

$^{99m}$Tc (chlorine)(dimethyl glyoxime)$_3$ 4-(aminomethyl)phenyl boron

Following the procedure of example 2, but substituting 4-(aminomethyl)boronic acid monohydrochloride for 4-[(diethylamino)methyl]benzene boronic acid monohydrochloride, yields 81% of the title complex.

EXAMPLE 38

$^{99m}$Tc (chlorine)(dimethyl glyoxime)$_3$ hexadecyl boron

Following the procedure of example 36, but substituting hexadecane boronic acid for 4-[(diethylamino)methyl]benzene boronic acid monohydrochloride, yields the title complex.

EXAMPLE 39

$^{99m}$Tc (chlorine)(dimethyl glyoxime)$_3$ 17-octadecenoic acid, 18-boron

Following the procedure of example 2, but substituting 18-borono-17-octadecenoic acid for boric acid, yields 62% of the title complex.

EXAMPLE 40

$^{99m}$Tc (chlorine)(dimethyl glyoxime)$_3$ 4-formylphenyl boron

Following the procedure of example 2, but substituting p-(benzaldehyde)boronic acid for boric acid, yields 47% of the title complex.

EXAMPLE 41

$^{99m}$Tc (chlorine)(dimethyl glyoxime)$_3$ 4-[[methyl (2-phenylethyl)amino]methyl]phenyl boron Following the procedure of example 2, but substituting 4-[[methyl(2-phenylethyl)amino]-methyl]benzene boronic acid monohydrochloride for boric acid, yields the title complex.

EXAMPLE 42

$^{99m}$Tc (chlorine)(dimethyl glyoxime)$_3$ 4-ethylphenyl boron

Following the procedure of example 2, but substituting 4-ethylbenzene boronic acid for boric acid, yields the title complex.

EXAMPLE 43

$^{99m}$Tc (chlorine)(dimethyl glyoxime)$_3$
2,4-dimethylphenyl boron

Following the procedure of example 2, but substituting 2,4-dimethylbenzene boronic acid for boric acid, yields the title complex.

EXAMPLE 44

$^{99m}$Tc (chlorine)(dimethyl glyoxime)$_3$
4-[(dimethylamino)methyl]phenyl boron Following the procedure of example 2, but substituting 4-[(dimethylamino)methyl]benzene boronic acid monohydrochloride for boric acid, yields the title complex.

EXAMPLE 45

$^{99m}$Tc (chlorine)(dimethyl glyoxime)$_3$
4-[(diisopropylamino)methyl]phenyl boron Following the procedure of example 2, but substituting 4-[(diisopropylamino)methyl]benzene boronic acid monohydrochloride for boric acid, yields the title complex.

EXAMPLE 46

$^{99m}$Tc (chlorine)(1,2-cyclohexanedionedioxime)$_3$
3-(1-piperidinyl)propyl boron Into a 5 ml siliconized vial are measured 0.5 mg of 1,2-cyclohexanedione dioxime in 0.1 ml of ethanol, 1.0 mg of 3-(1-piperidinyl)propane boronic acid monohydrochloride, 0.2 ml of saturated sodium chloride, 10 mg of citric acid and 50 µl of saturated stannous pyrophosphate.

Sodium pertechnetate in physiological saline (0.2 ml) is added to the vial which is then heated at 100° C. for 5 minutes yielding 84% of the title complex.

EXAMPLE 47

$^{99m}$Tc (chlorine)(1,2-cyclohexanedione dioxime)$_3$
3-(4-methyl-1-piperidinyl)propyl boron Following the procedure of example 46, but substituting 3-(4-methyl-1-piperidinyl)propane boronic acid monohydrochloride for 3-(1-piperidinyl)propane boronic acid monohydrochloride, yields 82% of the title complex.

EXAMPLE 48

$^{99m}$Tc (chlorine)(1,2-cyclohexanedione dioxime)$_3$
3-(4-morpholinyl)propyl boron Following the procedure of example 46, but substituting 3-(4-morpholinyl)propane boronic acid monohydrochloride for 3-(1-piperidinyl)propane boronic acid monohydrochloride, yields 90% of the title complex.

EXAMPLE 49

$^{99m}$Tc (chlorine)(1,2-cyclohexanedione dioxime)$_3$
3-aminophenyl boron

Following the procedure of example 46, but substituting 3-aminobenzene boronic acid monohydrochloride for 3-(1-piperidinyl)propane boronic acid monohydrochloride yields 93% of the title complex.

EXAMPLE 50

$^{99m}$Tc (chlorine)(1,2-cyclohexanedione dioxime)$_3$
3-(4-phenyl-1-piperidinyl) propyl boron Following the procedure of example 46, but substituting 5.0 mg of 3-(4-phenyl-1-piperidinyl)-propane boronic acid monohydrochloride for 3-(1-piperidinyl) boronic acid monohydrochloride and labeling with sodium pertechnetate in physiological saline (0.3 ml), yields 84% of the title complex.

EXAMPLE 51

$^{99m}$Tc (bromime)(1,2-cyclohexanedione dioxime)$_3$
3-(4-phenyl-1-piperidinyl) propyl boron Following the procedure of example 46, but substituting 5.0 mg of 3-(4-phenyl-1-piperidinyl)-propane boronic acid monohydrochloride for 3-(1-piperidinyl) propane boronic acid monohydrochloride and 100 mg of potassium bromide for sodium chloride yields the title complex.

EXAMPLE 52

$^{99m}$Tc (chlorine)(1,2-cyclohexanedione dioxime)$_3$
1-butyl boron

Following the procedure of example 46, but substituting 1-butane boronic acid for 3-(1-piperidinyl)propane boronic acid monohydrochloride and labeling with sodium pertechnetate in physiological saline (0.3 ml) yields 69% of the title complex.

EXAMPLE 53

$^{99m}$Tc (chlorine)(1,2-cyclohexanedione dioxime)$_3$
3-(5-dimethylamino-1-naphthalenesulfonylamino) phenyl boron Following the procedure of example 46, but substituting 3-(5-dimethylamino-1-naphthalenesulfonylamino)benzene boronic acid for 3-(1-piperidinyl)propane boronic acid monohydrochloride and labeling with sodium pertechnetate in physiological saline (0.3 ml), yields 80% of the title complex.

EXAMPLE 54

$^{99m}$Tc (chlorine)(1,2-ethanedione dioxime)$_3$ 3-(5-dimethylamino-1-naphthalenesulfonylamino)phenyl boron Following the procedure of example 53, but substituting 1,2-ethanedione dioxime for 1,2-cyclohexanedione dioxime, yields 71% of the title compound.

EXAMPLE 55

$^{99m}$Tc (chlorine)(1,2-cyclohexanedione dioxime)$_3$ methyl boron

Into a 5 ml siliconized serum vial are measured 2.0 mg of 1,2-cyclohexanedione dioxime in 0.2 ml of ethanol, 2.0 mg of methane boronic acid, 10 mg of citric acid, 100 mg of sodium chloride, 1.0 mg of diethylenetriamine pentaacetic acid, and 50-60 μg of anhydrous stannous chloride in 1 μl of concentrated hydrochloric acid.

Sodium pertechnetate in physiological saline (0.5 ml) is added to the vial which is then heated at 100° C. for 5 minutes yielding 85% of the title complex.

EXAMPLE 56

$^{99m}$Tc (bromine)(1,2-cyclohexanedione dioxime)$_3$ methyl boron

Following the procedure of example 55, but substituting potassium bromide for sodium chloride and labeling with sodium pertechnetate in physiological saline (0.1 ml), yields the title complex.

EXAMPLE 57

$^{99m}$Tc (chlorine)(1,2-cyclohexanedione dioxime)$_3$ 4-ethylphenyl boron

Following the procedure of example 55, but substituting 4-ethylbenzene boronic acid for methane boronic acid, yields the title complex.

EXAMPLE 58

$^{99m}$Tc (chlorine)(dimethyl glyoxime)$_3$ 4-[1-(diisopropylamino) ethyl]phenyl boron Following the procedure of example 2, but substituting 4-[1-(diisopropylamino)ethyl]benzene boronic acid for boric acid, yields the title complex.

EXAMPLE 59

$^{99m}$Tc (chlorine)(dimethyl glyoxime)$_3$ 4-[(isopropylamino)methyl]phenyl boron Following the procedure of example 2, but substituting 4-[(isopropylamino)methyl]benzene boronic acid monohydrochloride for boric acid, yields 8% of the title complex.

EXAMPLE 60

$^{99m}$Tc (chlorine)(1,2-cyclohexanedione dioxime)$_3$ 4-methylphenyl boron

Following the procedure of example 2, but substituting 4-toluene boronic acid for boric acid and 1,2-cyclohexanedione dioxime for dimethyl glyoxime, yields the title complex.

EXAMPLE 61

$^{99m}$Tc (chlorine)(dimethyl glyoxime)$_3$ 2,4,6-trimethylphenyl boron

Following the procedure of example 2, but substituting 2,4,6-trimethylbenzene boronic acid for boric acid, yields the title complex.

EXAMPLE 62

$^{99m}$Tc (chlorine)(dimethyl glyoxime)$_3$ 2-methyl-1-propyl boron

Following the procedure of example 2, but substituting 2-methyl-1-propane boronic acid for boric acid, yields 84% of the title complex.

EXAMPLE 63

$^{99m}$Tc (chlorine)(1,2-cyclohexanedione dioxime)$_3$ 1-heptyl boron

Following the procedure of example 2, but substituting 1-heptane boronic acid for boric acid and 1,2-cyclohexanedione dioxime for dimethyl glyoxime, yields the title complex.

EXAMPLE 64

$^{99m}$Tc (chlorine)(dimethyl glyoxime)$_3$ 9-carboxynonyl boron

Following the procedure of example 2, but substituting 10-borono decanoic acid for boric acid, yields the title complex.

EXAMPLE 65

$^{99m}$Tc (chlorine)(1,2-cyclohexanedione dioxime)$_3$ 2-methyl-1-propyl boron

Following the procedure of example 2, but substituting 2-methyl-1-propane boronic acid for boric acid and 1,2-cyclohexanedione dioxime for dimethyl glyoxime, yield 85% of the title complex.

EXAMPLE 66

$^{99m}$Tc (chlorine)(1,2-cyclohexanedione dioxime)$_3$ ethyl boron

Following the procedure of example 2, but substituting ethane boronic acid for boric acid and 1,2-cyclohexanedione dioxime for dimethyl glyoxime, yields 88% of the title complex.

EXAMPLE 67

$^{99m}$Tc (chlorine)(dimethyl glyoxime)$_3$ ethyl boron

Following the procedure of example 2, but substituting ethane boronic acid for boric acid, yields 77% of the title complex.

EXAMPLE 68

$^{99m}$Tc (chlorine)(dimethyl glyoxime)$_3$ 3-methylphenyl boron

Following the procedure of example 2, but substituting 3-toluene boronic acid for boric acid yields the title complex.

EXAMPLE 69

$^{99m}$Tc (chlorine)(dimethyl glyoxime)$_3$ 2-methylphenyl boron

Following the procedure of example 2, but substituting o-toluene boronic acid for boric acid yields the title complex.

EXAMPLE 70

$^{99m}$Tc (chlorine)(dimethyl glyoxime)$_3$ cyclopentyl boron

Following the procedure of example 2, but substituting cyclopentane boronic acid for boric acid, yields the title complex.

EXAMPLE 71

$^{99m}$Tc (chlorine)(dimethyl glyoxime)$_3$ 2-butyl boron

Following the procedure of example 2, but substituting 2-butane boronic acid for boric acid, yields the title complex.

EXAMPLE 72

$^{99m}$Tc (chlorine)(dimethyl glyoxime)$_3$ 4-methoxyphenyl boron

Following the procedure of example 2, but substituting 4-methoxybenzene boronic acid for boric acid, yields the title complex.

EXAMPLE 73

$^{99m}$Tc (chlorine)(dimethyl glyoxime)$_3$ 4-(t-butyl)phenyl boron

Following the procedure of example 2, but substituting 4-(t-butane)benzene boronic acid for boric acid, yields the title complex.

EXAMPLE 74

$^{99m}$Tc (chlorine)(1,2-ethanedione dioxime)$_3$ 1-butyl boron

Following the procedure of example 2, but substituting 1-butane boronic acid for boric acid and 1,2-ethanedione dioxime for dimethyl glyoxime yields 76% of the title complex.

EXAMPLE 75

$^{99m}$Tc (chlorine)(dimethyl glyoxime)$_3$ 4-(2-propyl)phenyl boron

Following the procedure of example 2, but substituting 4-(2-propane)benzene boronic acid for boric acid, yields the title complex

EXAMPLE 76

$^{99m}$Tc (chlorine)(1,2-cyclohexanedione dioxime)$_3$ hydroxy boron

Following the procedure of example 2, but substituting 1,2-cyclohexanedione dioxime for dimethyl glyoxime, and omitting ethanol, yields the title complex.

EXAMPLE 77

$^{99m}$Tc (chlorine)(α-furyldioxime)$_3$ methyl boron

Following the procedure of example 2, but substituting α-furyldioxime for dimethyl glyoxime, and methane boronic acid for boric acid, yields the title complex.

EXAMPLE 78

$^{99m}$Tc (chlorine)(3-methyl-1,2-cyclopentanedione dioxime)$_3$ methyl boron

Following the procedure of example 2, but substituting 3-methyl-1,2-cyclopentanedione dioxime for dimethyl glyoxime and methane boronic acid for boric acid, yields the title complex.

EXAMPLE 79

$^{99m}$Tc (chlorine)(1,2-cyclopentanedione dioxime)$_3$ methyl boron

Following the procedure of example 2, but substituting 1,2-cyclopentanedione dioxime for dimethyl glyoxime, and methane boronic acid for boric acid, yields the title complex.

EXAMPLE 80

$^{99m}$Tc (chlorine)(1,2-cyclohexanedionedioxime)$_3$, 3-(1-piperidinyl)propyl boron Into a 5 ml siliconized vial are measured 0.5 mg of 1,2-cyclohexanedione dioxime in 0.1 ml of ethanol, 1.0 mg of 3-(1-piperidinyl)propane boronic acid monohydrochloride, 0.2 ml of saturated sodium chloride, 10 mg of citric acid, 40 mg of hydroxypropyl gamma cyclodextrin and 50 µl of saturated stannous pyrophosphate.

Sodium pertechnetate Tc-99m in physiological saline (0.2 ml) is added to this vial which is then heated at 100° C. for 5 minutes yielding 84% of the title complex.

The solution remains clear without containing particulate matter for more than 6 hours after preparation.

EXAMPLE 81

$^{99m}$Tc (chlorine)(1,2-cyclohexanedione dioxime)$_3$ methyl boron

Into a 5 ml serum vial are measured 2.0 mg of 1,2-cyclohexanedione dioxime, 2.0 mg of methane boronic acid, 10 mg of citric acid, 10 mg of sodium chloride, 1.0 mg of diethylenetriamine pentaacetic acid, 45 mg of hydroxypropyl gamma cyclodextrin, 50 micrograms of $SnCl_2$ and 0.5-3 μl of concentrated hydrochloric acid.

Sodium pertechnetate Tc-99m in physiological saline (0.5 ml) is added to the vial which is then heated at 100° C. for 5 minutes yielding 85% of the title complex.

The solution remains clear without containing particulate matter for more than 6 hours after preparation.

Teboroxime Imaging Protocols

Reference is made to FIGS. 6A-L, which are timelines illustrating teboroxime imaging protocols, in accordance with respective embodiments of the present invention. These protocols take advantage of the high-speed and high-resolution capabilities of imaging system 10. These protocols are typically implemented using an automated administration system, such as automated administration system 56, described hereinabove with reference to FIG. 4. Such automated administration is typically performed while the patient is positioned at the imaging system. Alternatively, these protocols are performed using manual administration, or a combination of automated and manual administration. These protocols are typically used to produce quantitative results, such as quantitative measures of flow of perfusion agents, and/or the percentage of the myocardium that is ischemic for a metabolic agent.

In respective embodiments of the present invention, the protocols described herein, including hereinbelow with reference to FIGS. 6A-L, are used to produce "clinically-valuable images," as defined hereinabove.

Figure 6A:
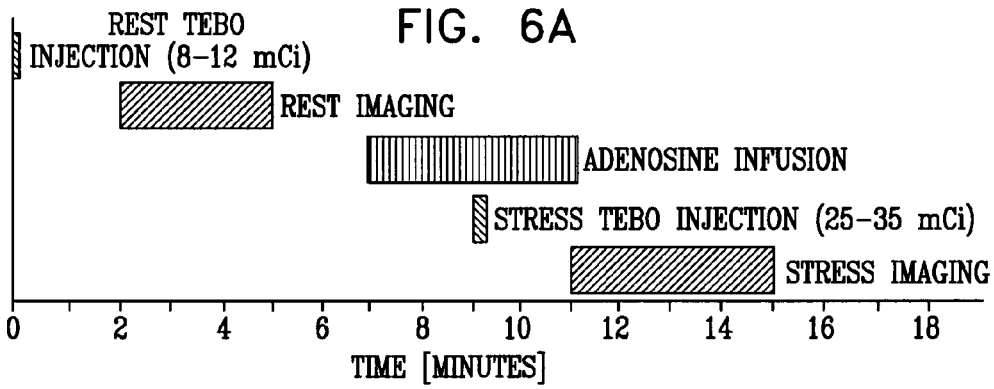

FIG. 6A is a timeline illustrating an ultra-fast teboroxime rest/teboroxime pharmacological stress protocol, in accordance with an embodiment of the present invention. The protocol begins with the injection of teboroxime while the patient is at rest, and typically already positioned in the imaging system. The dose of this first injection is typically less than about 15 mCi, such as between about 6 and about 15 mCi, such as between about 8 and about 12 mCi, e.g., between about 9 and about 11 mCi. Alternatively, the dose is less than 10 mCi, e.g., less than 5 mCi. (It is noted that the injections typically take only several seconds, but are shown with slightly longer durations in the figures for clarity of illustration.) Rest imaging is performed beginning at between about 1.5 and about 3 minutes after injection, such as between about 1.75 and about 2.25 minutes (e.g., at about 2 minutes) after injection. The duration of the imaging is typically between about 2 and about 4 minutes, e.g., about 3 minutes.

For some applications, physical (e.g., exercise) or pharmacological stress is applied, such as by infusion of adenosine or persantine, beginning at about 1 to about 3 minutes after the completion of the rest imaging, e.g., at about 2 minutes after the completion of the rest imaging, and/or at about 6 to about 8 minutes after the initial teboroxime injection, e.g., at about 7 minutes. The infusion is typically has a dose of between about 120 μg/kg/min and about 160 μg/kg/min, e.g., about 140 μg/kg/min; this dose is also typically used for adenosine infusion in the protocols described hereinbelow, unless otherwise specified therein. The infusion typically has a duration of between about 3 and about 5 minutes, e.g., about 4 minutes. A stress injection of teboroxime is performed, typically between about 1 and about 3 minutes after commencement of the infusion, e.g., about 2 minutes after commencement. The stress injection typically has a dose greater than about 15 mCi, such as between about 20 and about 40 mCi, e.g., between about 25 and about 35 mCi, or between about 30 and 35 mCi. Stress imaging is performed, typically upon completion of the stress infusion (e.g., at about 11 minutes from the first teboroxime injection) or soon thereafter, and typically with a duration of between about 3 and about 5 minutes, e.g., about 4 minutes.

This protocol enables the quick performance of a myocardial perfusion study (in about 15 minutes), which is convenient for the patient, and allows high throughput for the imaging facility. This protocol takes advantage of the narrow window of opportunity provided by the teboroxime uptake curve, i.e., after lung clearance at about 2 minutes after injection, and prior to substantial liver uptake beginning at about 5 minutes after injection. As mentioned above, this protocol is typically implemented using an automated administration system, such as automated administration system 56, described hereinabove with reference to FIG. 4. Such automated administration is typically performed while the patient is positioned at the imaging system. Such automation is convenient for the technician, the physician, and the patient, because the entire procedure is completed in about 15 minutes without the patient having to leave the imaging system. Such automation also substantially reduces the likelihood of error in administration.

In an embodiment of the present invention, an ultra-fast teboroxime/teboroxime protocol is provided, that is similar to the protocol described above with reference to FIG. 6A, except that the stress phase is performed before the rest phase. For some applications, the dose of teboroxime administered during the stress phase is between about 1 and about 5 mCi, between about 5 and about 15 mCi, between about 15 and about 25 mCi, between about 25 and about 30 mCi, or greater than about 30 mCi. For some applications, the dose of teboroxime administered during the rest phase is between about 1 and about 5 mCi, between about 5 and about 15 mCi, between about 15 and about 25 mCi, between about 25 and about 30 mCi, or greater than about 30 mCi.

In some embodiments of the present invention, combination teboroxime/thallium protocols are provided.

Figure 6B:
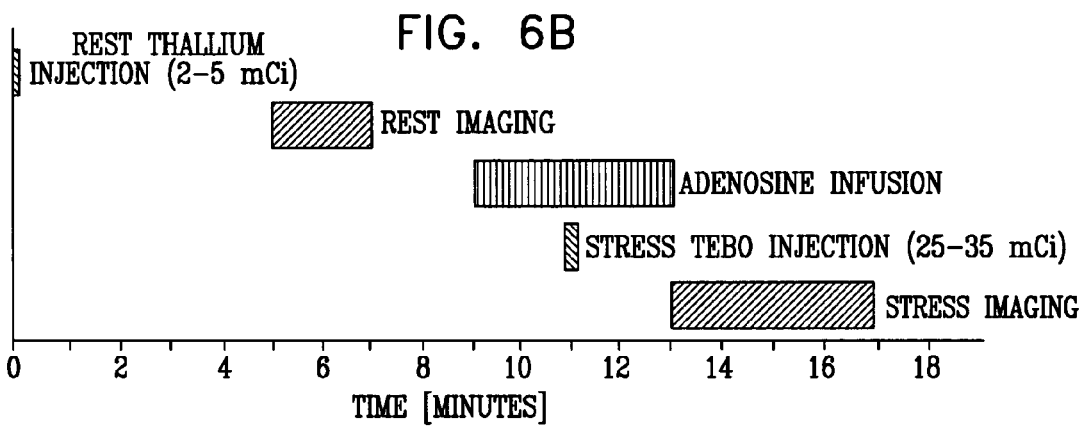

FIG. 6B is a timeline illustrating an ultra-fast thallium rest/teboroxime pharmacological stress protocol, in accordance with an embodiment of the present invention. The protocol begins with the injection of thallium while the patient is at rest. The dose of this first injection is typically between about 2 and about 5 mCi, such as between about 3 and about 4 mCi. Beginning at between about 4 and about 6 minutes after injection, e.g., at about 5 minutes after injection, rest imaging is performed. The duration of the imaging is typically between about 1 and about 3 minutes, e.g., about 2 minutes.

Pharmacological stress is applied, such as by infusion of adenosine or persantine, beginning at about 1 to about 3 minutes after the completion of the rest imaging, e.g., at about 2 minutes after the completion of the rest imaging, and/or at about 8 to about 10 minutes after the initial teboroxime injection, e.g., at about 9 minutes. The infusion typically has a duration of between about 3 and about 5 minutes, e.g., about 4 minutes. A stress injection of teboroxime is performed, typically between about 1 and about 3 minutes after commencement of the infusion, e.g., about 2 minutes after commencement. The stress injection typically has a dose of between about 20 and about 40 mCi, e.g., between about 25 and about 35 mCi. Stress imaging is performed, typically upon completion of the stress infusion (e.g., at about 13 minutes from the thallium injection) or soon thereafter, and typically with a duration of between about 3 and about 5 minutes, e.g., about 4 minutes.

This protocol enables the quick performance of a myocardial perfusion study (in less than about 20 minutes), which is convenient for the patient, and allows high throughput for the imaging facility. This protocol takes advantage of the narrow window of opportunity provided by the teboroxime uptake curve, i.e., after lung clearance at about 2 minutes after injection, and prior to substantial liver uptake beginning at about 5 minutes after injection. As mentioned above, this protocol is typically implemented using an automated administration system, such as automated administration system 56, described hereinabove with reference to FIG. 4. Such automated administration is typically performed while the patient is positioned at the imaging system. Such automation is convenient for the technician, the physician, and the patient, because the entire procedure is completed in less than about 20 minutes without the patient having to leave the imaging system. Such automation also substantially reduces the likelihood of error in administration.

For some applications, this protocol is used for a viability study, by administering a vasodilator, such as nitroglycerin or isosorbide dinitrate, in conjunction with the stress teboroxime injection. Imaging typically begins between about 2 and about 4 minutes after completion of administration of the vasodilator, e.g., after nitroglycerin has dissolved sublingually.

In an embodiment of the present invention, another ultra-fast teboroxime rest/thallium pharmacological stress protocol is provided. As in the protocol described above with reference to FIG. 6B, the present protocol begins with the injection of thallium while the patient is at rest. The dose of this first injection is typically between about 2 and about 5 mCi, such as between about 3 and about 4 mCi. The protocol then waits until the level of thallium in the blood circulation falls substantially, typically for between about 3 and about 10 minutes after injection, e.g., between about 4 and about 6 minutes after injection. Unlike in the protocol described with reference to FIG. 6B, no imaging is performed at this point in the present protocol.

Physical or pharmacological stress is applied, such as by infusion of adenosine or persantine, typically having a duration of between about 3 and about 5 minutes, e.g., about 4 minutes. A stress injection of teboroxime is performed, typically between about 1 and about 3 minutes after commencement of the infusion, e.g., about 2 minutes after commencement. The stress injection typically has a dose of between about 20 and about 40 mCi; e.g., between about 25 and about 35 mCi, or, alternatively, less than 30 mCi, such as less than 20 mCi, less than 10 mCi, or less than 5 mCi.

The present protocol provides two techniques for performance of the imaging, typically upon completion of the stress infusion or soon thereafter:

According to a first technique, first stress imaging of the teboroxime is performed, typically having a duration of between about 3 and about 5 minutes, e.g., about 4 minutes. Upon completion of the teboroxime stress imaging, at which point the teboroxime has substantially cleared from the heart, but the thallium has not yet substantially cleared from the heart, rest imaging of the thallium is performed. Because of the different energy levels of the teboroxime and the thallium, emissions from the thallium during the imaging of the teboroxime do not generally substantially interfere with the teboroxime imaging. For some applications, the stress and rest imaging are performed during a single scanning session, while for other applications, there is a delay between the completion of the stress imaging and the commencement of the rest imaging.

According to a second technique, stress imaging of the teboroxime and rest imaging of the thallium are performed simultaneously, utilizing the different energy levels of the two radiopharmaceuticals.

This protocol is typically implemented using an automated administration system, such as automated administration system 56, described hereinabove with reference to FIG. 4. Such automated administration is typically performed while the patient is positioned at the imaging system. Such automation is convenient for the technician, the physician, and the patient, because the entire procedure is completed in about 15 to 20 minutes without the patient having to leave the imaging system. Such automation also substantially reduces the likelihood of error in administration.

In an embodiment of the present invention, yet another ultra-fast teboroxime rest/thallium pharmacological stress protocol is provided, in which stress imaging is performed prior to rest imaging. The protocol begins with the application of physical or pharmacological stress, such as by infusion of adenosine or persantine, typically having a duration of between about 3 and about 5 minutes, e.g., about 4 minutes. If physical stress is used, the patient may perform the exercise prior to position the patient at the imaging system. A stress injection of thallium is performed, typically between about 1 and about 3 minutes after commencement of the infusion, e.g., about 2 minutes after commencement. Typically, the stress thallium has a dose of between about 3 and about 5 mCi, between about 1 and about 5, or less than about 1 mCi, and the stress imaging has a duration of between about 3 and about 5 minutes, e.g., about 4 minutes.

The protocol continues with the injection of teboroxime while the patient is at rest, and typically already positioned in the imaging system. The dose of this injection is typically less than about 15 mCi, such as between about 6 and about 15 mCi, such as between about 8 and about 12 mCi, e.g., between about 9 and about 11 mCi. Alternatively, the dose is less than 10 mCi, e.g., less than 5 mCi. Rest imaging is performed beginning at between about 1.5 and about 3 minutes after injection, such as between about 1.75 and about 2.25 minutes (e.g., at about 2 minutes) after injection. The duration of the imaging is typically between about 2 and about 4 minutes, e.g., about 3 minutes.

As with the other protocols described herein, this protocol is typically implemented using an automated administration system, such as automated administration system 56, described hereinabove with reference to FIG. 4.

Alternatively, one of the following techniques is used for performing the stress and rest imaging, after the rest injection of teboroxime and the stress injection of thallium have been performed:

According to a first technique, first rest imaging of the teboroxime is performed, typically having a duration of between about 2 and about 4 minutes, e.g., about 3 minutes. Upon completion of the teboroxime rest imaging, at which point the teboroxime has substantially cleared from the heart, but the thallium has not yet substantially cleared from the heart, stress imaging of the thallium is performed. Because of the different energy levels of the teboroxime and the thallium, emissions from the thallium during the imaging of the teboroxime do not generally substantially interfere with the teboroxime imaging. For some applications, the rest and stress imaging are performed during a single scanning session, while for other applications, there is a delay between the completion of the rest imaging and the commencement of the stress imaging.

According to a second technique, rest imaging of the teboroxime and stress imaging of the thallium are performed simultaneously, utilizing the different energy levels of the two radiopharmaceuticals.

Application of stress, whether physical or pharmacological, generally causes the patient to move (exercise clearly involves motion, and pharmacological stress is often uncomfortable for the patient). Application of the stress before the imaging portion of the protocol begins allows the performance of the stress and the rest imaging without an intervening application of stress. As a result, there is a high likelihood that the patient will remain in the same position for both the stress and rest imaging, which enables the registration of the resulting stress and rest images with one another. The patient's remaining in the same position between the two scans also obviates the need to separately set imaging parameters (such as physical location/orientation of the imaging elements of the camera) for the two scans. In an embodiment of the present invention, imaging parameters are set just once for two or more imaging acquisitions, such as for a stress imaging acquisition and a rest imaging acquisition.

Figure 6C:
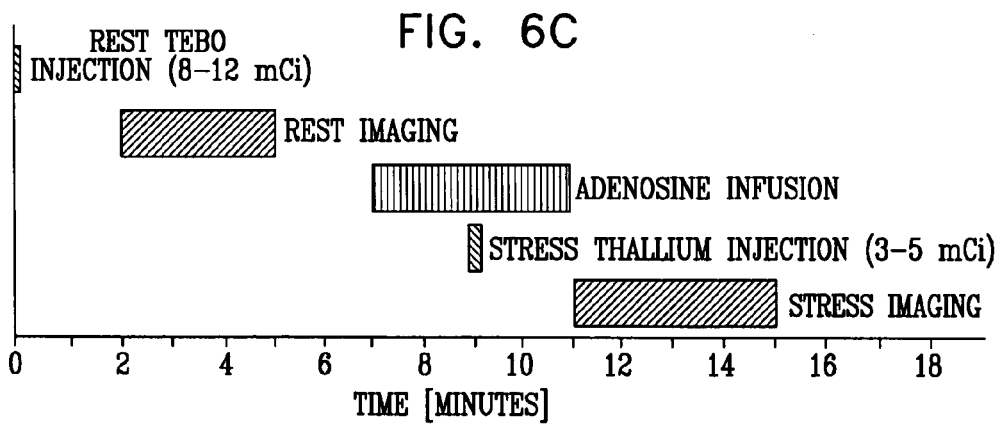

FIG. 6C is a timeline illustrating an ultra-fast teboroxime rest/thallium pharmacological stress protocol, in accordance with an embodiment of the present invention. This protocol is similar to the protocol described hereinabove with reference to FIG. 6A, except that the stress portion of the protocol is performed with thallium rather than teboroxime. Typically, the stress thallium has a dose of between about 3 and about 5 mCi, and the stress imaging has a duration of between about 3 and about 5 minutes, e.g., about 4 minutes.

This protocol enables the quick performance of a myocardial perfusion study (in about 15 minutes), which is convenient for the patient, and allows high throughput for the imaging facility. This protocol takes advantage of the narrow window of opportunity provided by the teboroxime uptake curve, i.e., after lung clearance at about 2 minutes after injection, and prior to substantial liver uptake beginning at about 5 minutes after injection. As mentioned above, this protocol is typically implemented using an automated administration system, such as automated administration system 56, described hereinabove with reference to FIG. 4. Such automated administration is typically performed while the patient is positioned at the imaging system. Such automation is convenient for the technician, the physician, and the patient, because the entire procedure is completed in about 15 minutes without the patient having to leave the imaging system. Such automation also substantially reduces the likelihood of error in administration.

In an alternative embodiment of this protocol, the teboroxime injection is performed under stress, followed by stress imaging of the teboroxime, and, thereafter, the thallium injection is performed at rest, followed by rest imaging of the thallium. As mentioned above, the application of the stress before both image acquisitions, rather than between the image acquisitions, increases the likelihood that registration of the stress and rest images can be performed.

Figure 6D:
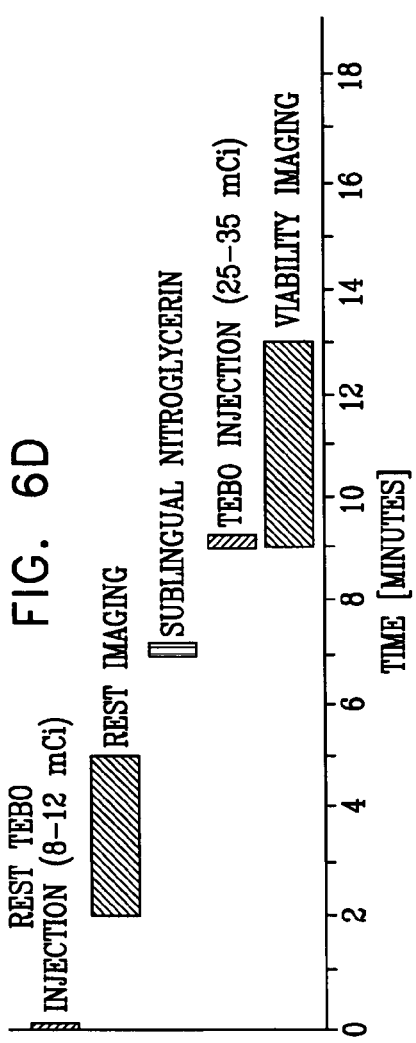

FIG. 6D is a timeline illustrating a vasodilator-enhanced ultra-fast teboroxime rest/thallium pharmacological stress protocol for a viability study, in accordance with an embodiment of the present invention. The protocol begins with the injection of teboroxime while the patient is at rest. The dose of this first injection is typically between about 6 and about 15 mCi, such as about 8 and about 12 mCi, e.g., between about 9 and about 11 mCi. Rest imaging is performed beginning at between about 1.5 and about 3 minutes after injection, such as between about 1.75 and about 2.25 minutes (e.g., at about 2 minutes) after injection. The duration of the imaging is typically between about 2 and about 4 minutes, e.g., about 3 minutes. A vasodilator, such as nitroglycerin (e.g., sublingual, as a tablet or spray) or isosorbide dinitrate is administered at about 1 to about 3 minutes after the completion of the rest imaging, e.g., at about 2 minutes after the completion of the rest imaging, and/or at about 6 to about 8 minutes after the initial teboroxime injection, e.g., at about 7 minutes. For applications in which the vasodilator comprises nitroglycerin, the nitroglycerin typically has a dose of between about 0.3 mg and about 0.6 mg if administered sublingually, and about 1 mg if administered buccally. For applications in which the vasodilator comprises isosorbide dinitrate, the isosorbide dinitrate typically has a dose of about 5 mg for chewable administration, and between about 2.5 mg and about 5 mg for sublingual administration. An injection of teboroxime is performed, typically between about 2 and about 3 minutes after administration of the vasodilator. This injection typically has a dose of between about 20 and about 40 mCi, e.g., between about 25 and about 35 mCi. Viability imaging is performed, typically beginning upon completion of the second teboroxime injection (e.g., at about 9 minutes from the first teboroxime injection if the second teboroxime injection is performed 2 minutes after administration of the vasodilator) or soon thereafter, and typically with a duration of between about 3 and about 5 minutes, e.g., about 4 minutes.

This protocol enables the quick performance of a myocardial perfusion study (in about 15 minutes), which is convenient for the patient, and allows high throughput for the imaging facility. This protocol takes advantage of the narrow window of opportunity provided by the teboroxime uptake curve, i.e., after lung clearance at about 2 minutes after injection, and prior to substantial liver uptake beginning at about 5 minutes after injection. As mentioned above, this protocol is typically implemented using an automated administration system, such as automated administration system 56, described hereinabove with reference to FIG. 4. Such automated administration is typically performed while the patient is positioned at the imaging system. Such automation is convenient for the technician, the physician, and the patient, because the entire procedure is completed in about 15 minutes without the patient having to leave the imaging system. Such automation also substantially reduces the likelihood of error in administration.

Nitroglycerin is believed to exert its primary vasodilatory effect on epicardial conductance vessels. Thus, nitroglycerin appears to preferentially direct blood flow to post-stenotic zones of ischemia. This leads to increased uptake of the stress radiopharmaceutical in regions where the ischemic tissue is still viable. Patients with viable tissue are more likely to respond well to revascularization than patients with irreversibly damaged tissue.

For some applications, the vasodilator is administered together with pharmacological stress, such an adenosine or persantine infusion. The infusion typically has a lower dose than is used for pharmacological stress alone. For example, the lower dose may be between about 60 µg/kq/min and about 80 µg/kq/min, e.g., about 70 µg/kq/min.

For some applications, the stress portion of this protocol is performed using thallium rather than teboroxime. Typically, the stress thallium has a dose of between about 3 and about 5 mCi, and the stress imaging has a duration of between about 3 and about 5 minutes, e.g., about 4 minutes.

Figure 6E:
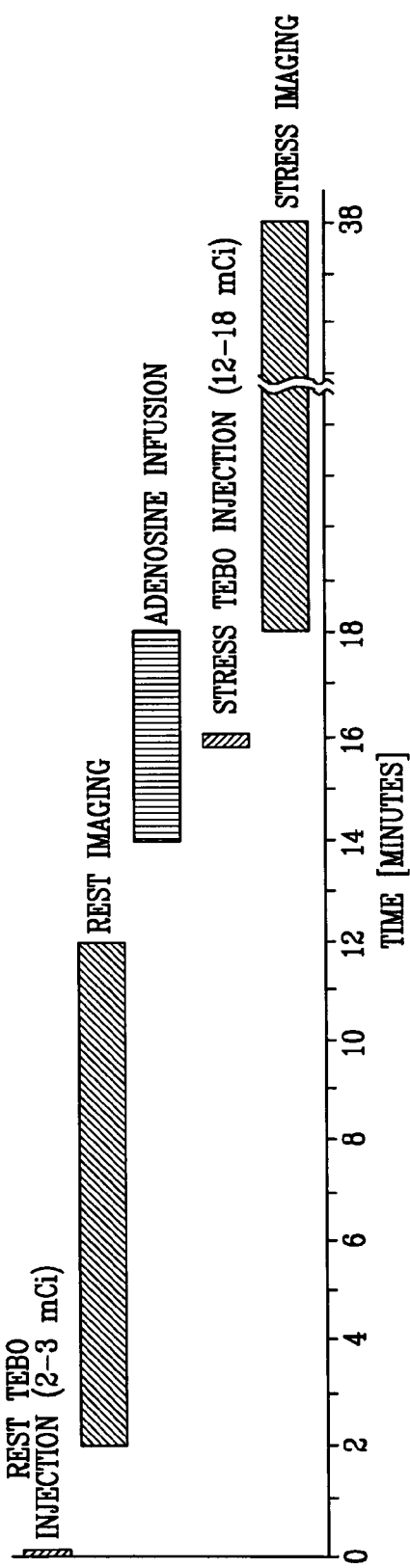

FIG. 6E is a timeline illustrating a low-dose teboroxime rest/teboroxime pharmacological stress protocol, in accordance with an embodiment of the present invention. The protocol begins with the injection of teboroxime while the patient is at rest. The dose of this first injection is typically less than 5 mCi, such as less than or equal to 4.5 mCi, less than or equal to 4 mCi, or less than or equal to 3 mCi, e.g., between about 2 and about 3 mCi. Rest imaging is performed beginning at between about 1.5 and about 3 minutes after injection, such as between about 1.75 and about 2.25 minutes (e.g., at about 2 minutes) after injection. The duration of the imaging is typically between about 2 and about 12 minutes, such as between about 4 and about 10 minutes, e.g., between about 6 and about 8 minutes.

Pharmacological stress is applied, such as by infusion of adenosine or persantine, beginning at about 1 to about 3 minutes after the completion of the rest imaging, e.g., at about 2 minutes after the completion of the rest imaging, and/or about 14 minutes after the initial teboroxime injection. The infusion typically has a duration of between about 3 and about 5 minutes, e.g., about 4 minutes. A stress injection of teboroxime is performed, typically between about 1 and about 3 minutes after commencement of the infusion, e.g., about 2 minutes after commencement. The stress injection typically has a dose of between about 12 and about 18 mCi. Stress imaging is performed, typically upon completion of the stress infusion (e.g., at about 18 minutes from the first teboroxime injection) or soon thereafter, and typically with a duration of between about 15 and about 25 minutes, e.g., about 20 minutes.

This protocol enables the use of lower doses of teboroxime than were possible or contemplated in the past to the knowledge of the inventors. The use of such lower doses increases safety for both the patient and the technician. This protocol also decreases the contamination of the liver, with a consequent improvement in image quality. In addition, this protocol enables quick performance of a myocardial perfusion study (in about 40 minutes), which is convenient for the patient, and allows high throughput for the imaging facility. This protocol takes advantage of the narrow window of opportunity provided by the teboroxime uptake curve, i.e., after lung clearance at about 2 minutes after injection, and prior to substantial liver uptake beginning at about 5 minutes after injection. As mentioned above, this protocol is typically implemented using an automated administration system, such as automated administration system 56, described hereinabove with reference to FIG. 4. Such automated administration is typically performed while the patient is positioned at the imaging system. Such automation is convenient for the technician, the physician, and the patient, because the entire procedure is completed in about 15 minutes without the patient having to leave the imaging system. Such automation also substantially reduces the likelihood of error in administration.

Figure 6F:
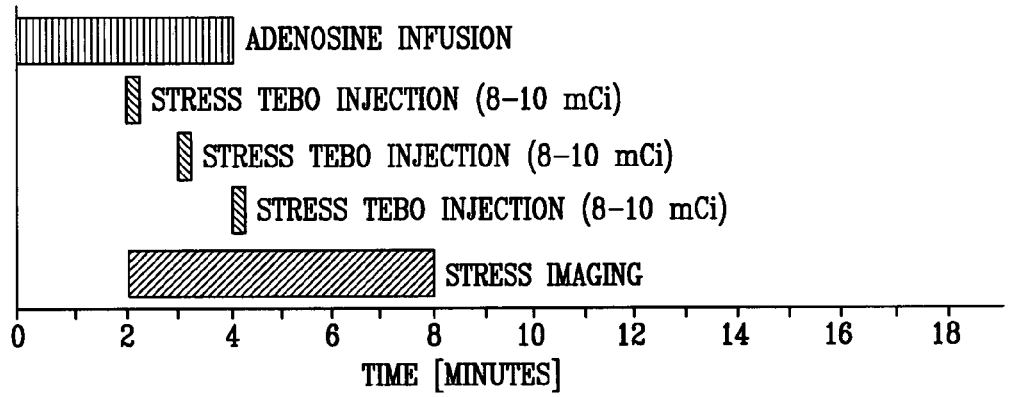

FIG. 6F is a timeline illustrating a teboroxime pharmacological stress-only protocol, in accordance with an embodiment of the present invention. The protocol begins with the application of pharmacological stress, such as by infusion of adenosine or persantine. The infusion typically has a duration of between about 3 and about 5 minutes, e.g., about 4 minutes. A stress injection of teboroxime is performed, typically between about 1 and about 3 minutes after commencement of the infusion, e.g., about 2 minutes after commencement. The stress injection typically has a dose of between about 6 and about 12 mCi, e.g., about 8 and about 10 mCi. Stress imaging is performed, typically beginning substantially simultaneously with the injection, and continuing until the conclusion of the protocol, typically at about 6 to about 10 minutes, e.g., about 8 minutes from the commencement of the infusion. One or more additional stress teboroxime injections are performed during the imaging, such as at about 1 minute and about 2 minutes after the first teboroxime injection. Typically, the one or more additional injection are spaced apart by at least 30 seconds, such as by between about 45 and about 90 seconds, e.g., by about 60 seconds. These additional one or more injections typically have about the same dose as the first injection. Alternatively, all or a portion of the one or more injections has a different respective dose.

The early stress and serial images provided by this protocol, which include rest, stress, and washout images, provide the physician with additional valuable kinetic information that has not been available in the past using conventional imaging techniques. In addition, as mentioned hereinabove, with reference to FIG. 2, the imaging is typically performed while the patient is substantially upright, and using ROI-centric imaging. These techniques reduce the interference of emissions from the liver. Such reduced interference, in combination with the high-resolution, rapid imaging enabled by imaging system 10, enable the performance of serial imaging after stress, in order to assess post-stress left-ventricular function recovery (i.e., by identifying stunning myocardium). Such serial imaging can be characterized as dynamic imaging with 2-minute frames. A study performed with this protocol, while not providing absolute flow measurements, does provide flow estimates, which for some applications obviate the need to perform a rest study. In summary, the sequential injection of teboroxime enables the monitoring of changes in uptake and washout dynamics as a function of post-stress recovery.

Furthermore, this protocol enables the quick performance of a myocardial perfusion study (in less than about 10 minutes), which is convenient for the patient, and allows high throughput for the imaging facility. This protocol takes advantage of the narrow window of opportunity provided by the teboroxime uptake curve, i.e., after lung clearance at about 2 minutes after injection, and prior to substantial liver uptake beginning at about 5 minutes after injection. As mentioned above, this protocol is typically implemented using an automated administration system, such as automated administration system 56, described hereinabove with reference to FIG. 4. Such automated administration is typically performed while the patient is positioned at the imaging system. Such automation is convenient for the technician, the physician, and the patient, because the entire procedure is completed in no more than about 15 minutes without the patient having to leave the imaging system. Such automation also substantially reduces the likelihood of error in administration.

Figure 6G:
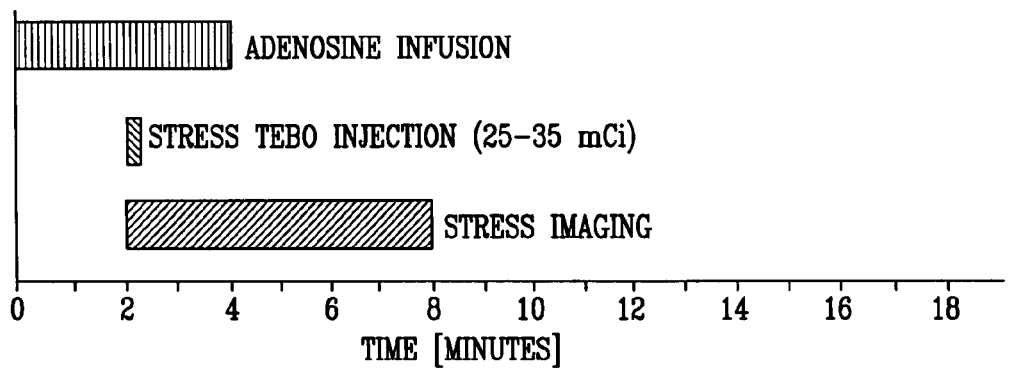

FIG. 6G is a timeline illustrating a teboroxime pharmacological stress-only protocol, in accordance with an embodiment of the present invention. This protocol is similar to the protocol described hereinabove with reference to FIG. 6F, except that only a single stress injection of teboroxime is performed, typically with a dose of between about 20 and about 40 mCi, e.g., between about 25 and about 35 mCi.

This protocol enables the quick performance of a myocardial perfusion study (in less than about 10 minutes), which is convenient for the patient, and allows high throughput for the imaging facility. This protocol takes advantage of the narrow window of opportunity provided by the teboroxime uptake curve, i.e., after lung clearance at about 2 minutes after injection, and prior to substantial liver uptake beginning at about 5 minutes after injection. As mentioned above, this protocol is typically implemented using an automated administration system, such as automated administration system 56, described hereinabove with reference to FIG. 4. Such automated administration is typically performed while the patient is positioned at the imaging system. Such automation is convenient for the technician, the physician, and the patient, because the entire procedure is completed in no more than about 15 minutes without the patient having to leave the imaging system. Such automation also substantially reduces the likelihood of error in administration.

FIG. 6H is a timeline illustrating a dual-isotope teboroxime stress/I-123 BMIPP protocol, for a combined perfusion and fatty acid imaging study, in accordance with an embodiment of the present invention. I-123 BMIPP is a fatty acid imaging agent that has been available in Japan for many years, and is currently in Phase In clinical trials in the United States. BMIPP is characterized by "ischemic memory," in which an area at risk of acute myocardial infarction can still be detected as a defect even a couple of weeks after successful reperfusion therapy. For myocardial viability studies, image analysis is based on comparison between BMIPP and a perfusion tracer.

As reported by the above-mentioned article by Dilsizian V et al., in acute myocardial infarctions, a strong association has been reported, on the one hand, between a "negative" mismatch (i.e., BMIPP less than perfusion) and jeopardized but viable myocardium, and, on the other hand, between a matched decreased uptake of both tracers and nonviable tissue. In chronic infarctions, the number of segments with less BMIPP than perfusion has been shown to be the strongest predictor of adverse cardiac events at follow-up. A "positive" mismatch with more BMIPP than perfusion, although rarely encountered, appears to be associated with unstable conditions or severe wall motion abnormalities. In sum, the combined evaluation of BMIPP and perfusion reliably differentiates between viable and nonviable myocardial tissue in both acute and chronic phases of ischemic heart disease. It is also a useful tool for viability assessment with SPECT. A negative mismatch with less BMIPP than perfusion identifies viable tissue, whereas a matched decreased uptake of both tracers corresponds to myocardial scar.

The protocol begins with the injection of teboroxime while the patient is at rest. The dose of this first injection is typically between about 6 and about 15 mCi, such as between about 8 and about 12 mCi, e.g., between about 9 and about 11 mCi. Rest imaging is performed beginning at between about 1.5 and about 3 minutes after injection, such as between about 1.75 and about 2.25 minutes (e.g., at about 2 minutes) after injection. The duration of the imaging is typically between about 2 and about 4 minutes, e.g., about 3 minutes.

Pharmacological stress is applied, such as by infusion of adenosine or persantine, beginning at about 0.5 to about 3 minutes after the completion of the rest imaging, e.g., at about 1 minute after the completion of the rest imaging, and/or at about 5 to about 7 minutes after the initial teboroxime injection, e.g., at about 6 minutes. The infusion typically has a duration of between about 3 and about 5 minutes, e.g., about 4 minutes. A stress injection of I-123 BMIPP is performed, typically between about 1 and about 3 minutes after commencement of the stress, e.g., about 2 minutes after commencement. The stress injection typically has a dose of between about 3 and about 5 mCi. Stress imaging is performed, typically upon completion of the stress infusion (e.g., at about 10 minutes from the teboroxime injection) or soon thereafter, and typically with a duration of between about 4 and about 6 minutes, e.g., about 5 minutes.

For some applications, imaging system 10 performs the imaging of the BMIPP uptake using static imaging, in which the resulting image is compared with the teboroxime perfusion study. Alternatively, the imaging system performs the imaging of the BMIPP uptake using dynamic acquisition, in order to calculate flow measurements and perform quantitative assessment of the I-123 BMIPP total myocardial uptake ratio (TMUR).

FIG. 6I is a timeline illustrating a dual-isotope simultaneous-imaging teboroxime rest/I-123 BMIPP protocol, for a combined perfusion and fatty acid imaging study, in accordance with an embodiment of the present invention. This protocol is generally appropriate for use in an emergency room setting, when a patient has suffered an acute event and/or presents with chest pain of unknown cause. Under such circumstances, the performance of stress imaging is generally not recommended.

The protocol begins with the simultaneous or near-simultaneous injection of teboroxime and BMIPP while the patient is at rest. Typically, the teboroxime and the BMIPP are administered as a mixture (i.e., a cocktail); alternatively, the teboroxime and the BMIPP are administered separately. The dose of the teboroxime is typically between about 6 and about 15 mCi, such as about 8 and about 12 mCi, e.g., between about 9 and about 11 mCi, and the dose of the BMIPP is typically between about 3 and about 5 mCi. Simultaneous rest imaging of both radiopharmaceuticals is performed beginning at between about 1.5 and about 3 minutes after injection, such as between about 1.75 and about 2.25 minutes (e.g., at about 2 minutes) after injection. The duration of the imaging is typically between about 2 and about 4 minutes, e.g., about 3 minutes. The imaging system produces separate images of each radiopharmaceutical agent by separating the energies of the two isotopes, while imaging both isotopes simultaneously. The result is two separate images, each of which provides the uptake a respective one of the tracers.

This dual-isotope protocol enables the identification of some ischemic events that could not otherwise be identified in a myocardial perfusion-only study. For example, if a patient suffers a minor myocardial event, by the time the patient reaches the hospital perfusion may be restored to the infarcted area. In such a case, a myocardial perfusion-only study would not be capable of detecting the event. Because of the ischemic memory characteristic of BMIPP, the present dual-isotope protocol is likely to identify the ischemic event. Furthermore, the protocol is quick (about 5 minutes total time), which is suitable for emergency room settings.

FIG. 6J is a timeline illustrating a dual-isotope teboroxime rest/Tc-99m ECDG stress protocol for a combined perfusion and static glucose metabolism imaging study, in accordance with an embodiment of the present invention. The protocol begins with the injection of teboroxime while the patient is at rest. The dose of this first injection is typically between about 6 and about 15 mCi, such as about 8 and about 12 mCi, e.g., between about 9 and about 11 mCi. Rest imaging is performed beginning at between about 1.5 and about 3 minutes after injection, such as between about 1.75 and about 2.25 minutes (e.g., at about 2 minutes) after injection. The duration of the imaging is typically between about 2 and about 4 minutes, e.g., about 3 minutes.

Pharmacological stress is applied, such as by infusion of adenosine or persantine, beginning at about 0.5 to about 3 minutes after the completion of the rest imaging, e.g., at about 1 minute after the completion of the rest imaging. The infusion typically has a duration of between about 3 and about 5 minutes, e.g., about 4 minutes. A stress injection of Tc-99m ECDG is performed, typically between about 1 and about 3 minutes after commencement of the infusion, e.g., about 2 minutes after commencement. The ECDG typically has a dose of between about 20 and about 40 mCi, e.g., between about 25 and about 35 mCi. During ischemia, ischemic cells begin to metabolize glucose instead of fatty acids, resulting in an increased uptake of ECDG. Static stress imaging is performed upon completion of the pharmacological stress or soon thereafter, typically with a duration of between about 3 and about 5 minutes, e.g., about 4 minutes.

This protocol enables the quick performance of a combined myocardial perfusion and static glucose metabolism study (in about 15 minutes), which is convenient for the patient, and allows high throughput for the imaging facility. This protocol takes advantage of the narrow window of opportunity provided by the teboroxime uptake curve, i.e., after lung clearance at about 2 minutes after injection, and prior to substantial liver uptake beginning at about 5 minutes after injection. As mentioned above, this protocol is typically implemented using an automated administration system, such as automated administration system 56, described hereinabove with reference to FIG. 4. Such automated administration is typically performed while the patient is positioned at the imaging system. Such automation is convenient for the technician, the physician, and the patient, because the entire procedure is completed in about 15 minutes without the patient having to leave the imaging system. Such automation also substantially reduces the likelihood of error in administration.

FIG. 6K is a timeline illustrating a dual-isotope teboroxime rest/Tc-99m ECDG stress protocol, for a combined perfusion and dynamic glucose metabolism imaging study, in accordance with an embodiment of the present invention. This protocol is similar to the protocol described hereinabove with reference to FIG. 6J, except that the stress imaging is performed using dynamic acquisition, typically with frames having a duration of between about 20 seconds to about 1 minute. A longer stress imaging duration is consequently used, such as between about 4 and about 6 minutes, e.g., about 5 minutes.

This protocol enables the quick performance of a combined myocardial perfusion and dynamic glucose metabolism study (in about 15 minutes), which is convenient for the patient, and allows high throughput for the imaging facility. This protocol takes advantage of the narrow window of opportunity provided by the teboroxime uptake curve, i.e., after lung clearance at about 2 minutes after injection, and prior to substantial liver uptake beginning at about 5 minutes after injection. As mentioned above, this protocol is typically implemented using an automated administration system, such as automated administration system 56, described hereinabove with reference to FIG. 4. Such automated administration is typically performed while the patient is positioned at the imaging system. Such automation is convenient for the technician, the physician, and the patient, because the entire procedure is completed in about 15 minutes without the patient having to leave the imaging system. Such automation also substantially reduces the likelihood of error in administration.

FIG. 6L is a timeline illustrating a dynamic study for performing blood flow measurements and calculation of coronary flow reserve (CFR), in accordance with an embodiment of the present invention. The protocol begins with the injection of teboroxime while the patient is at rest, followed by flushing in order to prevent contamination of the subsequent injection (described below). The dose of this first injection is typically between about 6 and about 15 mCi, such as between about 8 and about 12 mCi, e.g., between about 9 and about 11 mCi. The flush is typically performed with between about 8 and about 12 ml of saline solution, e.g., about 10 ml of saline solution. Beginning substantially simultaneously with the injection (or even slightly prior thereto), such as less than 10 seconds after completion of the injection, e.g., less than 5 seconds or less than 2 seconds, low-resolution rest imaging is performed, typically for between about 20 and about 40 seconds, e.g., about 30 seconds. (It is noted that the scope of the phrase "beginning less than a certain number of seconds after completion of the injection" or similar phrases, as used herein, including in the claims, is intended to include beginning even prior to completion of the injection, and even prior to commencement of the injection.) Each of the frames typically has a short duration of between about 3 and about 7 seconds, e.g., about 5 seconds. The low-resolution rest imaging is used to estimate the input function, which will is used later in the protocol in combination the high-resolution imaging to calculate absolute flow measurements, as describe hereinbelow.

High-resolution imaging is performed with longer frames, beginning substantially immediately upon completion of the low-resolution rest imaging, e.g., less than 10 seconds after completion, such as less than 5 seconds or less than 2 seconds. These frames typically have a duration of between about 15 to about 25 about seconds, e.g., about 20 seconds, which frame duration is typically at least 2 times greater than the duration of the low-resolution frames, e.g., at least 3 or 5 times greater. The high-resolution imaging typically has a total duration of between about 4 and about 6 minutes, e.g., about 4.5 minutes.

Pharmacological stress is applied, such as by infusion of adenosine or persantine, typically beginning substantially upon completion of the high-resolution rest imaging, or within about an hour after completion of the high-resolution rest imaging. The infusion typically has a duration of between about 3 and about 5 minutes, e.g., about 4 minutes. Typically, between about 1 and about 3 minutes after commencement of the stress, e.g., about 2 minutes after commencement, a stress injection of teboroxime is performed, typically having a dose of between about 20 and about 40 mCi, e.g., between about 25 and about 35 mCi. Typically substantially immediately upon completion of the stress infusion (e.g., at about 7 minutes from the first, rest teboroxime injection) or soon thereafter, e.g., within 10 seconds of completion of the stress infusion, low-resolution stress imaging is performed, typically for between about 20 and about 40 seconds, e.g., about 30 seconds. Each of the frames typically has a short duration of between about 3 and about 7 seconds, e.g., about 5 seconds. The low-resolution stress imaging is used to estimate counts in the blood pool (i.e., the left and right ventricular chambers), from which the input function is derived, as described hereinbelow.

High-resolution stress imaging is performed with longer frames, beginning substantially immediately upon completion of the low-resolution stress imaging. These frames typically have a duration of between about 15 and about 25 seconds, e.g., about 20 seconds. The high-resolution imaging typically has a total duration of between about 4 and about 6 minutes, e.g., about 4.5 minutes:

This protocol enables the assessment of absolute myocardial perfusion and CFR. By sampling the myocardium in approximately 5-second intervals during the first, low-resolution phase, the system accurately estimates the input function. As described above, once the tracer begins to diffuse into the myocardium, the sampling time of the myocardium is typically increased to approximately 30-second intervals. The system analyzes these dynamic sequences using a compartmental analysis approach. This protocol generally requires precise knowledge of the rate of the injection of the bolus, and a flush immediately following the injection of the radiopharmaceutical. For this reason, the injection is typically performed using an automated administration system, such as automated administration system 56, described hereinabove with reference to FIG. 4. In addition, it is generally important that the bolus have a relatively small volume. For this reason, the teboroxime and the saline flush (and, typically, the stress pharmacological agent) are typically supplied in a pre-packaged ready-to-use radiopharmaceutical agent container 54 that is loaded into the automated administration system, as described hereinabove with reference to FIG. 4. The flush is used to push the bolus through and to complete the injection over a short period of time, as well as to wash out residual radioactivity from the infusion line, so that this activity does not contaminate the next bolus injection. The entire rest-stress procedure is typically performed in less than about 15 minutes, and provides absolute blood flow measurements for both rest and stress studies.

This protocol generally enables the achievement of better contrast in coronary flow reserve for those patients with distributed coronary disease at an earlier stage in the development of the disease, than is possible using conventional imaging techniques.

In respective embodiments of the present invention, the radiopharmaceuticals used in any of the protocols described herein are provided in a kit, and/or in a container. For protocols including more than one radiopharmaceutical, the radiopharmaceuticals may be stored mixed together in a single compartment of the container, such as if the protocol calls for simultaneous administration of the radiopharmaceuticals, or separately in separate compartments of the container, such as if the protocol calls for separate administration of the radiopharmaceuticals. Typically, the container contains information; such as protocol, patient information, administration, camera configuration information (e.g., scanning parameters), or analysis information, or is associated with a data carrier containing such information. For example, techniques may be used that are described in U.S. patent application Ser. No. 11/750,057, filed May 17, 2007, and/or in International Patent Application PCT/IL2006/000562, filed May 11, 2006, which published as PCT Publication WO 06/129301. Furthermore, the protocols described herein are typically implemented using an automated administration system, such as automated administration system 56, described hereinabove with reference to FIG. 4. Such automated administration is typically performed while the patient is positioned at the imaging system. Alternatively, these protocols are performed using manual administration, or a combination of automated and manual administration. These protocols are typically used to produce quantitative results, such as quantitative measures of flow of perfusion agents, and/or the percentage of the myocardium that is ischemic for a metabolic agent.

For some applications, this protocol is performed in combination with techniques described in the above-cited article by El Fakhri G et al., mutatis mutandis.

For some applications, the protocols described hereinabove with reference to FIG. 6A-H or 6J-L are performed using exercise stress instead of pharmacological stress. Typically, the stress injection occurs once a determination is made that the patient has achieved a threshold percentage of cardiac output, such as at least 85% or at least 100%, as is known in the art. Such cardiac output typically occurs between about 1 and about 3 minutes after commencement of exercise, such as about 2 minutes after commencement of exercise. The exercise typically continues for a total of between about 5 minutes and about 15 minutes, e.g., about 10 minutes.

For some applications, the protocols described herein that include the application of pharmacological stress are performed using a bolus injection of A2A, rather than an infusion of adenosine or persantine.

In an embodiment of the present invention, a protocol is provided that comprises pre-administrating a trace quantity of a radiopharmaceutical, and performing a scan of the patient to determine a location of the patient's heart based on the radiation emitted from the radiopharmaceutical. A trace quantity is typically a quantity that less than about 2 mCi, less than 1 mCi, less than 0.5, or less 0.1 mCi. Alternatively, the trace quantity is less than 10% of the quantity used for the diagnostic imaging. The camera (e.g., the position and/or orientation of the camera) of the imaging system is configured, based on the determined location of the heart. Teboroxime is administered to the patient at a dose appropriate for imaging, such as one the doses described herein, and an imaging procedure is performed. For some applications, the trace radiopharmaceutical comprises thallium-chloride or Tc-99m, such as $^{99m}$Tc-sestamibi, $^{99m}$Tc-tetrofosmin, or teboroxime. For some applications, the trace radiopharmaceutical and the imaging-dose teboroxime are supplied in a kit configured to be used with an automated administration system, such as described herein.

In an embodiment of the present invention, teboroxime is administered in conjunction with image acquisition by the camera. Typically, the image begins prior to the administration, or at the time of administration, or within three minutes after administration. Photons are acquired in list mode, and the kinetics of the teboroxime in the myocardium are analyzed to produce a quantification of coronary flow reserve (CFR). Typically, the protocol comprises acquiring the image only during rest or only during stress (such as physical or pharmacological stress, e.g., by infusion of adenosine or persantine). For some applications, the teboroxime and the stress agent are supplied in a kit configured to be used with an automated administration system. The information regarding the time of administration may be provided to or from the camera.

In respective embodiments of the present invention, the protocols described herein, including hereinabove with reference to FIGS. 6A-L, further comprise performance of washout imaging, typically beginning upon completion of the stress imaging, or soon thereafter. Washout imaging is performed to investigate the washout kinetics of the particular tracer. Since washout kinetics in healthy myocardium may differ from the washout kinetics of ischemic or infarcted tissue, this type of analysis may provide clinically meaningful information for a more accurate diagnosis. Significant washout of teboroxime occurs two minutes after injection (at the time of peak uptake) and continues for about 10 minutes after injection. This type of analysis may be performed as an extension of any one of the protocols mentioned herein. For some applications, such washout imaging is performed as a semi-quantitative measurement of flow by comparing sequential two-minute images. For absolute flow measurements, the dynamic protocols (e.g., 10 second scans) are typically extended for up to 10 minutes to analyze the washout kinetics with absolute flow rates in different regions of the myocardium. For some applications, such washout imaging is performed to determine a non-dynamic estimate of tracer intensity. For some applications, the result may be a display of an "image" of the kinetic parameters (k1, k2, . . . ) per location in 3D space (or a list of such values of the kinetic parameters for selected regions, without full 3D presentation), such as described, for example, in above-mentioned International Application PCT/IL2006/001291 (see the section entitled "Kinetic Modeling").

In respective embodiments of the present invention, gating is performed on the stress acquisitions of protocols described herein, including those described hereinabove with reference to FIGS. 6A-L, for example using 8, 16, or 32 bins. For performing this gating, techniques may be used that are described in one or more of the references incorporated herein by reference, including the patent and patent application publications.

The higher resolution provided by the techniques described herein compared to conventional SPECT imaging techniques generally reduces partial volume effects, which are caused by a portion of the imaged voxels falling partially within both blood and cardiac tissue. These partial volume effects are particularly detrimental to dynamic imaging studies, which rely on quantitative analysis of curves over time. Such slope analysis necessarily increases noise, which is further aggravated by the presence of partial voxels as input. For some applications, in order to further reduce partial volume effects, the imaging system uses a non-uniform voxel grid, such as by using sub-voxels and/or adaptive voxel borders. For example, techniques described in above-mentioned International Application PCT/IL2006/001291 may be used for this purpose.

In accordance with respective embodiments of the present invention, dual-radiopharmaceutical protocols include the administration and simultaneous imaging of the following combinations of teboroxime with one or more other labeled radiopharmaceutical agents and/or pharmacological stress agents. Typically, the teboroxime and the agent(s) are administered as a mixture (i.e., a cocktail) before or during a simultaneous imaging procedure; alternatively, the teboroxime and/or the agent(s) are administered separately before or during a simultaneous imaging procedure.

(a) teboroxime, and (b) I-123 BMIPP, for simultaneously studying myocardial perfusion and fatty acid metabolism;

(a) teboroxime, and (b) Tc-99m ECDG, for simultaneously studying myocardial perfusion and glucose metabolism (during ischemia, ischemic cells begin to metabolize glucose instead of fatty acids, resulting in an increased uptake of ECDG);

(a) teboroxime, and (b) Tl-201-thallous chloride, for a dynamic myocardial perfusion study that analyzes the different kinetics of the teboroxime and the thallium, for either a rest or stress study. The teboroxime typically has a low dose, such that Compton residuals produced by the teboroxime do not mask the emissions of the thallium, such as described with reference to FIG. 18 of the above-reference International Application PCT/IL2006/000562. For some applications, the protocol includes an initial low-resolution portion having relatively short frames, followed by a higher-resolution portion having longer frames, such as described hereinabove with reference to FIG. 6L, for example, in order to provide quantitative kinetic information for both tracers; and (a) teboroxime, and (b) $^{123}$I-Fatty acid, for simultaneously studying myocardial perfusion and fatty acid metabolism.

In an embodiment of the present invention, a multiple isotope combination protocol is provided for studying different pathological processes indicative of acute myocardial ischemia. In accordance with this protocol, the following labeled radiopharmaceutical agents are administered as bolus IV injections:

(a) I-123-BMIPP, at a dose of between about 0.5 and about 2.5 mCi, e.g., about 2 mCi, followed by a wait of about 30 to about 60 minutes;

(b) Tl-201-thallous chloride, at a dose of between about 0.5 to about 2 mCi, e.g., about 1 mCi; and (c) teboroxime, at a dose of between about 8 and about 12 mCi, e.g., about 10 mCi.

Agents (b) and (c) are administered as a cocktail, or as separate injections at approximately the same time (in which case the thallium is typically administered first). Simultaneous image acquisition of all three radiopharmaceutical agents is performed during or soon after administration of agents (b) and (c), typically using an up to about 30 minute acquisition time, such as between about 5 and about 15 minutes, which is faster than that of standard imaging protocols. Typically, camera 22 of imaging system 10 performs image acquisition using an energy window of between about 2% and about 10% of the emitted energy levels of the radiopharmaceutical agents. Typically, detectors 40 of camera 22 sweep the region of interest once every approximately 10 to approximately 15 seconds. Simultaneous imaging provides more accurate identification of myocardial perfusion pathologies than is generally possible using conventional imaging techniques and protocols.

In an embodiment of the present invention, a fast, single-isotope, combined rest and stress teboroxime imaging protocol is provided. While under the camera, a patient is injected with about 8-10 mCi teboroxime, and rest imaging is performed with a duration of about 2 to about 5 minutes, e.g., about 3 minutes. The patient is then subject to pharmacological stress, for example, by the administration of adenosine or persantine. At the peak stress level, the patient is injected with about 20-30 mCi teboroxime, while under the camera. Substantially immediately after the second injection, a post-stress imaging is performed with a duration of between about 1 and about 4 minutes, e.g., about 2 minutes. The total imaging time of this protocol is between about 3 and about 7 minutes, e.g., about 5 minutes.

In an embodiment of the present invention, a rest teboroxime cardiac perfusion protocol is provided. The perfusion is described by quantitative parameters (ml/min/gr), coronary flow reserve, and parametric quantitation. While under the camera, a patient is injected with up to about 30 mCi teboroxime, and imaging is begun immediately. Imaging is performed for up to about 15 minutes, with an energy window of between about 3% and about 15%. This protocol enables the study of fluid flow, rate of tracer uptake (passive or active), tracer accumulation and redistribution, tracer metabolism, and secretion and/or washout (active or passive) of tracer/metabolites.

In an embodiment of the present invention, a stress teboroxime cardiac perfusion protocol is provided. The perfusion is described by quantitative parameters (ml/min/gr), coronary flow reserve, and parametric quantitation. A patient is subjected to pharmacological stress, for example, by the administration of adenosine or persantine, or to physical stress, for example, by exercising on a treadmill. At the peak stress level, while under the camera, the patient is injected with up to about 4 mCi teboroxime, and imaging is begun immediately. Imaging is taken for a time of up to 15 minutes, with an energy window of between 3 and 15%. This protocol enables the study of fluid flow, rate of tracer uptake (passive or active), tracer accumulation and redistribution, tracer metabolism, and secretion and/or washout (active or passive) of tracer/metabolites.

In an embodiment of the present invention, a fast, single-isotope Tc-99m-teboroxime imaging protocol is provided. While at rest, a patient is injected with about 8-10 mCi of teboroxime, typically while the patient is under the camera, and a rest imaging procedure having a duration of about 10 minutes is performed. The patient is then subject to a stress, such as pharmacological stress, e.g., by the administration of adenosine or persantine. At peak stress level, the patient is injected with about 20-30 mCi of teboroxime, typically while positioned under the camera. Substantially immediately after the second injection, a post-stress imaging of about 2 minutes is taken. The total imaging time of this protocol is about 12 minutes, and the total patient time is about 20 minutes.

In an embodiment of the present invention, a protocol for studying myocardial perfusion and apoptosis is provided. A patient is injected with up to about 15 mCi teboroxime and up to about 1 to about 3 mCi In-111-annexin, e.g., up to about 2 mCi In-111-annexin. After a waiting time of up to about 24 hours, imaging is taken for a period of up to about 30 minutes, with an energy window of between about 2% and about 10%.

In respective embodiments of the present invention, all of the protocols described herein, including the protocols described hereinabove with reference to FIGS. 6A-L, are used to produce "clinically-valuable images," as defined hereinabove.

For some applications, the protocols described hereinabove, including with reference to FIGS. 6B and 6D, use another vasodilator instead of nitroglycerin, such as isosorbide dinitrate. Similarly, protocols described herein as using adenosine for as a pharmacological stress agent may also use other stress agents, such as dipyridamole, persantine, or A2A.

Figure 7:
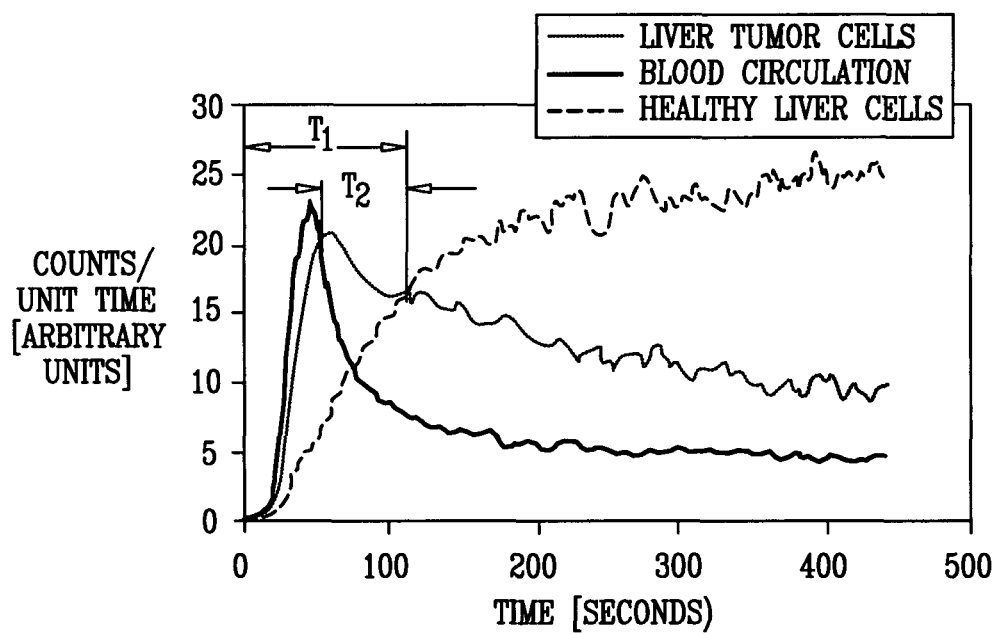
FIG. 7 is a graph showing hypothesized teboroxime uptake over time in the liver and the vicinity of the liver in cases in which a tumor has uptake similar to vascularized tissue, in accordance with an embodiment of the present invention.

Reference is made to FIG. 7, which is a graph showing hypothesized teboroxime uptake over time in the liver and the vicinity of the liver in cases in which a tumor has uptake similar to vascularized tissue, in accordance with an embodiment of the present invention. For such cases in which the tumor has uptake similar to vascularized tissue, which is quicker than that of healthy liver cells, the speed and sensitivity of the imaging techniques described herein enable the detection of the uptake and release of teboroxime from tumor cells in the liver prior to the uptake and metabolism of the teboroxime by healthy liver cells. These techniques may be used to enable detection and diagnosis of tumors of the liver. As can be seen in FIG. 7, the count of photons released from liver tumor cells during a time period $T_1$ is greater than the count of photons released from healthy liver cells, because tumor cells uptake the teboroxime more rapidly than do healthy liver cells. Performing imaging during $T_1$ thus provides information regarding the uptake of the teboroxime by tumor cells, in a way which emphasizes the increased uptake by the tumor cells compared to the uptake by the healthy liver cells. For some applications, $T_1$ concludes at the point in time of the intersection of the uptake curves of the healthy liver cells and the liver tumor cells. For instance, in the example shown in FIG. 7, $T_1$ concludes at about 110 seconds after administration of the teboroxime, while for other applications, $T_1$ concludes earlier, such as between about 90 and about 110 seconds, e.g., at about 100 seconds.

FIG. 7 also shows the photon emission of background blood circulation. In general, to diagnose tumors not believed to be near blood vessels, the imaging procedure begins at about 0 seconds after administration, because the photon count spike of the blood circulation does not affect the imaging. For applications in which the tumor is believed to be near a blood vessel, or the physician is otherwise concerned about the blood pool of nearby blood vessels; the imaging procedure is performed during the time period $T_2$, which begins when the photon emissions of the blood pool have dropped below the emissions of the tumor, i.e., at the point in time of the intersection of uptake curves of the blood circulation and the liver tumor cells. For instance, in the example shown in FIG. 7, $T_2$ begins at between about 50 and about 60 seconds after administration of the teboroxime.

In an embodiment of the present invention, these tumor diagnostic techniques are used to diagnosis tumors of other organs involved with metabolic clearance, such as the gall bladder or the spleen.

In the protocols described herein, thallium is typically administered at a dose of between about 1 and 5 mCi, such as between 2 and 4 mCi. Alternatively, thallium is administered at a dose less than 1 mCi.

Although some protocols described herein are described as having a maximum dose of 40 mCi of Tc-99m (e.g., Tc-99m teboroxime), for some applications these protocols use a higher dose, such as up to 50 mCi, 80 mCi, or even 100 mCi. Although some protocols described herein are described as having a dose of less than 5 mCi of Tc-99m (e.g., Tc-99m teboroxime), for some applications these protocols have a dose that is less than 2 mCi, or less than 1 mCi. Furthermore, the doses may vary based on physiological parameters of the subject, such as body mass.

The caret symbol (^) as used herein, including in the claims, signifies an exponent.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

International Patent Application PCT/IL2006/000562, filed May 11, 2006, entitled, "Unified management of radiopharmaceutical dispensing, administration, and imaging," which published as PCT Publication WO 06/129301;

International Patent Application PCT/IL2005/001173, filed Nov. 9, 2005, which published as PCT Publication WO 06/051531;

International Patent Application PCT/IL2005/000572, filed Jun. 1, 2005, which published as PCT Publication WO 2005/118659;

International Patent Application PCT/IL2005/000575, filed Jun. 1, 2005, which published as PCT Publication WO 2005/119025;

International Patent Application PCT/IL2005/001215, filed Nov. 16, 2005, which published as PCT Publication WO 06/054296;

International Patent Application PCT/IL2006/001291, filed Nov. 9, 2006, which published as PCT Publication WO 2007/054935;

U.S. Provisional Patent Application 60/625,971, filed Nov. 9, 2004;

U.S. Provisional Patent Application 60/628,105, filed Nov. 17, 2004;

U.S. Provisional Patent Application 60/630,561, filed Nov. 26, 2004;

U.S. Provisional Patent Application 60/632,236, filed Dec. 2, 2004;

U.S. Provisional Patent Application 60/632,515, filed Dec. 3, 2004;

U.S. Provisional Patent Application 60/635,630, filed Dec. 14, 2004;

U.S. Provisional Patent Application 60/636,088, filed Dec. 16, 2004;

U.S. Provisional Patent Application 60/640,215, filed Jan. 3, 2005;

U.S. Provisional Patent Application 60/648,385, filed Feb. 1, 2005;

U.S. Provisional Patent Application 60/648,690, filed Feb. 2, 2005;

U.S. Provisional Patent Application 60/675,892, filed Apr. 29, 2005;

U.S. Provisional Patent Application 60/691,780, filed Jun. 20, 2005;

U.S. Provisional Patent Application 60/700,318, filed Jul. 19, 2005;
U.S. Provisional Patent Application 60/700,299, filed Jul. 19, 2005;
U.S. Provisional Patent Application 60/700,317, filed Jul. 19, 2005;
U.S. Provisional Patent Application 60/700,753, filed Jul. 20, 2005;
U.S. Provisional Patent Application 60/700,752, filed Jul. 20, 2005;
U.S. Provisional Patent Application 60/702,979, filed Jul. 28, 2005;
U.S. Provisional Patent Application 60/720,034, filed Sep. 26, 2005;
U.S. Provisional Patent Application 60/720,652, filed Sep. 27, 2005;
U.S. Provisional Patent Application 60/720,541, filed Sep. 27, 2005;
U.S. Provisional Patent Application 60/750,287, filed Dec. 13, 2005;
U.S. Provisional Patent Application 60/750,334, filed Dec. 15, 2005;
U.S. Provisional Patent Application 60/750,597, filed Dec. 15, 2005;
U.S. Provisional Patent Application 60/799,688, filed May 11, 2006;
U.S. Provisional Patent Application 60/800,845, filed May 17, 2006, entitled, "Radioimaging camera for dynamic studies";
U.S. Provisional Patent Application 60/800,846, filed May 17, 2006, entitled, "Radioimaging protocols";
U.S. Provisional Patent Application 60/763,458, filed Jan. 31, 2006;
U.S. Provisional Patent Application 60/741,440, filed Dec. 2, 2005;
U.S. patent application Ser. No. 11/034,007, filed Jan. 13, 2005, which issued as U.S. Pat. No. 7,176,466;
U.S. patent application Ser. No. 09/641,973, filed Aug. 21, 2000;
U.S. Provisional Patent Application 60/750,294, filed Dec. 13, 2005 (this application has not been assigned to the assignee of the present application; an assignment is in the process of being executed and filed);
U.S. Provisional Patent Application 60/816,970, filed Jun. 28, 2006;
U.S. Provisional Patent Application 60/754,199, filed Dec. 28, 2005;
International Patent Application PCT/IL2006/000059, filed Jan. 15, 2006, which published as PCT Publication WO 2006/075333;
International Patent Application PCT/IL2005/000048, filed Jan. 13, 2005, which published as PCT Publication WO 2005/067383;
International Patent Application PCT/IL03/00917, filed Nov. 4, 2003, which published as PCT Publication WO 2004/042546;
Israel Patent Application 172349, filed Nov. 27, 2005;
Israel Patent Application 171346, filed Oct. 10, 2005;
International Application PCT/IL2006/000834, filed Jul. 19, 2006, which published as PCT Publication WO 2007/010534;
International Application PCT/IL2006/000840, filed Jul. 19, 2006, which published as PCT Publication WO 2007/010537;
International Application PCT/IL2006/000562, filed May 11, 2006, which published as PCT Publication WO 2006/129301;
International Application PCT/IL2006/001511, filed Dec. 28, 2006, which published as PCT Publication WO 2007/074467;
U.S. patent application Ser. No. 11/607,075, filed Dec. 1, 2006, which issued as U.S. Pat. No. 8,094,894;
U.S. patent application Ser. No. 11/656,548, filed Jan. 13, 2005, which published as U.S. Patent Application Publication 2007/0194241;
U.S. patent application Ser. No. 10/533,568, filed Nov. 4, 2003, which issued as U.S. Pat. No. 7,652,259;
International Application PCT/IL2007/000918, filed Jul. 19, 2007, which published as PCT Publication WO 2008/010227; and
U.S. patent application Ser. No. 11/750,057, filed May 17, 2007, which published as U.S. Patent Application Publication 2008/0131362.

The scope of the present invention includes embodiments described in the articles and patent publications cited in the Background of the Invention of this application. In an embodiment, techniques and apparatus described in one or more of such references are combined with techniques and apparatus described herein.

All doses and dose ranges given in this application are for a typical adult human having a typical body mass of between about 50 and about 90 kg. For imaging children, or underweight or overweight adults, the doses are adjusted appropriately, as known by those skilled in the art.

Although many embodiments of the present invention have been described as being performed on a cardiac region of interest (ROI), it is to be understand that for some applications, the techniques of these embodiments are used to image a non-cardiac ROI, or both a cardiac ROI and a non-cardiac ROI simultaneously.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for cardiac imaging, comprising:
administering to an adult human subject an amount of a $^{99m}$Tc-containing species having a radioactivity of less than 5 mCi at a time of administration; and
performing a SPECT imaging procedure of a cardiac region of interest (ROI) of the subject, wherein said $^{99m}$Tc-containing species has the formula $^{99m}$TcX(Y)$_3$Z, wherein:
X is an anion;
each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and
Z is a boron derivative of the formula B—R$_3$
wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

2. The method according to claim 1, wherein said Tc-99m-containing species has the structure:

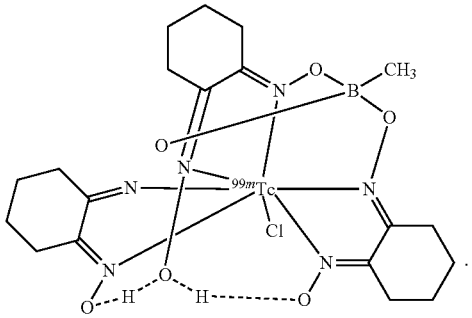

3. The method according to claim 1, comprising mixing:
(i) a source of anion;
(ii) a boronic acid derivative, or compounds which can react in situ to form a boronic acid derivative, having the formula $R_3B(OR_7)(OR_7)$ or a pharmaceutically acceptable salt thereof; wherein $R_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxy-alkenyl, haloalkyl, haloalkenyl, aryl, arylalkyl, or $R_4R_5N$-alkyl and $R_4$ and $R_5$ are each independently hydrogen, alkyl, or arylalkyl, or $R_4$ and $R_5$ when taken together with nitrogen atom to which they are attached form a 5 or 6-membered nitrogen containing heterocycle, and each $R_7$ is independently selected from hydrogen, alkyl and aryl;
(iii) at least one dioxime having the formula $HON=C(R_1)C(R_2)=NOH$ or a pharmaceutically acceptable salt thereof, wherein $R_1$ and $R_2$ are each independently hydrogen, halogen, alkyl, aryl, amino or a 5 or 6-membered nitrogen or oxygen containing heterocycle, or together $R_1$ and $R_2$ are $—(CR_8R_9)_n—$ wherein n is 3, 4, 5 or 6 and $R_8$ and $R_9$ are each independently hydrogen or alkyl;
(iv) a reducing agent; and
(v) a source of $^{99m}Tc$;
whereby to obtain the $^{99m}Tc$-containing species,
wherein administering comprises administering the $^{99m}Tc$-containing species thus obtained.

4. The method according to claim 3, wherein said mixing further comprises mixing hydroxypropyl gamma cyclodextrin with said source of anion, said boronic acid derivative, said dioxime and said reducing agent.

5. The method according to claim 1, wherein performing the SPECT imaging procedure comprises performing a dynamic SPECT imaging procedure.

6. The method according to claim 1, wherein performing the SPECT imaging procedure comprises acquiring at least one in 5000 photons emitted from the ROI during the SPECT imaging procedure.

7. The method according to claim 6, wherein performing, the SPECT imaging procedure comprises acquiring at least one in 2000 photons emitted from the ROI during the SPECT imaging procedure.

8. The method according to claim 1, wherein performing the SPECT imaging procedure comprises performing the SPECT imaging procedure with frames having a duration of no more than 30 seconds.

9. The method according to claim 1, wherein acquiring the image comprises acquiring, during the image acquisition period, at least 200,000 photons emitted from a portion of the ROI, which portion has a volume of no more than 500 cc.

10. The method according to claim 9, wherein the portion of the ROI has a volume of no more than 200 cc, and wherein acquiring the image comprises acquiring at least 1,000,000 photons during the image acquisition period from the portion of the ROI having the volume of no more than 200 cc.

11. The method according to claim 1, wherein performing the SPECT imaging procedure comprises generating an image having a resolution of at least 7×7×7 mm.

12. The method according to claim 11, wherein the $^{99m}Tc$-containing species as distributed within the ROI has a range of emission-intensities R, which is measured as emitted photons/unit time/volume, wherein generating the image comprises generating a reconstructed three-dimensional emission-intensity image of the ROI, and wherein at least 50% of voxels of the image have inaccuracies of less than 30% of range R.

13. The method according to claim 1, wherein the radioactivity is less than or equal to 4 mCi, and wherein administering comprises administering the $^{99m}Tc$-containing species having the radioactivity less than or equal to 4 mCi.

14. The method according to claim 1, wherein administering comprises administering the $^{99m}Tc$-containing species while the subject is at rest, and wherein performing the SPECT imaging procedure comprises performing a SPECT rest imaging procedure, and comprising, before or after the administering while the subject is at rest:
subjecting the subject to stress;
during the stress, administering to the subject a $^{99m}Tc$-containing species having the formula $^{99m}TcX(Y)_3Z$; and
performing a SPECT stress imaging procedure on the subject.

15. The method according to claim 1, wherein performing the SPECT imaging procedure of the cardiac ROI comprises performing myocardial perfusion imaging.

16. Apparatus for performing cardiac imaging, comprising an imaging system, which comprises:
SPECT imaging functionality; and
a control unit configured to drive the imaging functionality to perform a SPECT imaging procedure on a cardiac region of interest (ROI) of an adult human subject after administration to the subject of a $^{99m}Tc$-containing species having a radioactivity of less than 5 mCi at a time of administration, wherein said $^{99m}Tc$-containing species has the formula $^{99m}TcX(Y)_3Z$, wherein:
X is an anion;
each Y, which is independently chosen, is a vicinal dioxime having the formula $HON=C(R_1)(R_2)=NOH$ or a pharmaceutically acceptable salt thereof, wherein $R_1$ and $R_2$ are each independently hydrogen, halogen, alkyl, aryl, amino or a 5 or 6-membered, nitrogen or oxygen containing heterocycle, or together $R_1$ and $R_2$ are $—(CR_8CR_9)_n—$ wherein n is 3, 4, 5 or 6 and $R_8$ and $R_9$ are each independently hydrogen or alkyl; and
Z is a boron derivative of the formula $B—R_3$
wherein $R_3$ is hydroxy, alkyl, alkenyl, cycloalkyl, cycloalkenyl, alkoxy, carboxyalkyl, carhoxyalkenyl, hydroxyalkyl, hydroxyalkenyl, alkoxyalkyl, alkoxyalkenyl, haloalkyl, haloalkenyl, aryl, arylalkyl or $(R_4R_5N)$-alkyl and $R_4$ and $R_5$ are each independently hydrogen, alkyl, or arylalkyl, or $R_4$ and $R_5$ when taken together with the nitrogen atom to which they are attached form a 5 or 6-membered nitrogen containing heterocycle, wherein the SPECT imaging functionality is configured to generate an image having a resolution of at least 7×7×7 mm.

17. The apparatus according to claim 16, further comprising an automated administration system, configured to receive imaging protocol information for use with the $^{99m}$Tc-containing species, and to perform at least one automated administration of the $^{99m}$Tc-containing species into the subject at least in part responsively to the protocol information.

18. The apparatus according to claim 16, comprising a portable computer-communicatable non-transitory data carrier containing imaging protocol information for use with the $^{99m}$Tc-containing species.

19. The apparatus according to claim 18, comprising an automated administration system, configured to receive imaging protocol information for use with the $^{99m}$Tc-containing species from the data carrier, and to perform at least one automated administration of the $^{99m}$Tc-containing species into the subject at least in part responsively to the protocol information.

20. The apparatus according to claim 16, wherein the control unit is configured to drive the imaging functionality to perform myocardial perfusion imaging.

21. The apparatus according to claim 16, wherein the $^{99m}$Tc-containing species as distributed within the ROI has a range of emission-intensities which is measured as emitted photons/unit time/volume, wherein the SPECT imaging functionality is configured to generate a reconstructed three-dimensional emission-intensity image of the ROI, and wherein at least 50% of voxels of the image have inaccuracies of less than 30% of range R.

22. Apparatus for cardiac imaging, comprising a portable computer-communicatable non-transitory data carrier, which is configured to contain imaging protocol information for performing SPECT imaging on an adult human subject, the protocol information including an indication to administer a $^{99m}$Tc-containing species of the formula $^{99m}$TcX(Y)$_3$Z, and an indication to perform a SPECT imaging procedure on the subject, which procedure includes an image acquisition period having a duration not exceeding 5 minutes, wherein:
    X is an anion;
    each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and
    Z is a boron derivative of the formula B—R$_3$
    wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_3$ are each independently hydrogen, alkyl, or arylalkyl, or R$_4$ and R$_5$ when taken together with the nitrogen atom to which they are attached form a 5 or 6-membered nitrogen containing heterocycle.

23. The apparatus according to claim 22, wherein the protocol information includes an indication to perform a SPECT imaging procedure on the subject, which procedure includes: (a) a duration of an image acquisition period, and (b) a radioactivity of the $^{99m}$Tc-containing species, wherein a product (a) and (h) is less than 50 mCi*minutes.

24. The apparatus according to claim 22, comprising a container containing the $^{99m}$Tc-containing species, wherein the data carrier is associated with the container.

25. The apparatus according to claim 22, wherein the data carrier is configured to contain imaging protocol information for performing myocardial perfusion imaging.

26. A method for cardiac imaging, comprising:
    administering to an adult human subject a $^{99m}$Tc-containing species having a radioactivity of less than 50 mCi at a time of the administering; and
    performing a SPECT imaging procedure on a cardiac region of interest (ROI) of the subject with a image acquisition period having a duration not exceeding 5 minutes,
    wherein said $^{99m}$Tc-containing species has the formula $^{99m}$TcX(Y)$_3$Z, wherein:
    X is an anion;
    each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and
    Z is a boron derivative of the formula B—R$_3$
    wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

27. The method according to claim 26, wherein the radioactivity is less than 30 mCi.

28. The method according to claim 26, wherein the radioactivity is less than 5 mCi.

29. The method according to claim 26, wherein the duration of the image acquisition period does not exceed 3 minutes.

30. The method according to claim 26, wherein performing the SPECT imaging procedure comprises, during the image acquisition period, acquiring a number of photons emitted from the $^{99m}$Tc-containing species which is greater than or equal to at least one of the following numbers:
    one in 5000 photons emitted by the $^{99m}$Tc-containing species in the ROI during the image acquisition period, and
    200,000 photons emitted by the $^{99m}$Tc-containing species in a portion of the ROI, which portion has a volume of no more than 500 cc.

31. The method according to claim 30, wherein acquiring the number of photons comprises acquiring at least one in 5000 photons emitted from the ROI during the image acquisition period.

32. The method according to claim 30, wherein the portion of the ROI has a volume of no more than 200 cc, and wherein acquiring the number of photons comprises acquiring at least 1,000,000 photons during the image acquisition period from the portion of the ROI having the volume of no more than 200 cc.

33. The method according to claim 26, wherein performing the SPECT imaging procedure comprises generating an image having a resolution of at least 7×7×7 mm.

34. The method according to claim 33, wherein the $^{99m}$Tc-containing species as distributed within the ROI has a range of emission-intensities R, which is measured as emitted photons/unit time/volume, wherein performing the SPECT imaging procedure generating a reconstructed three-dimensional emission-intensity image of the ROI, and wherein at least 50% of voxels of the image have inaccuracies of less than 30% of range R.

35. The method according to claim 26, wherein administering comprises administering the $^{99m}$Tc-containing species while the subject is at rest, wherein performing the SPECT imaging procedure comprises performing a SPECT rest imaging procedure, and comprising, after completion of the SPECT rest imaging procedure:
  subjecting the subject to stress;
  during the stress, administering into the subject the $^{99m}$Tc-containing species having a radioactivity of between 15 and 40 mCi at a time of the administering; and
  performing a SPECT stress imaging procedure on the subject.

36. The method according to claim 26, wherein administering comprises administering the $^{99m}$Tc-containing species while the subject is at rest, wherein performing the SPECT imaging procedure comprises performing a SPECT rest imaging procedure, and comprising, after completion of the SPECT rest imaging procedure:
  subjecting the subject to stress;
  during the stress, administering to the subject thallium having a radioactivity of between 3 and 5 mCi at a time of the administering; and
  performing SPECT stress imaging on the subject.

37. The method according to claim 26, wherein administering comprises administering the $^{99m}$Tc-containing species while the subject is at rest, wherein performing the SPECT imaging procedure comprises performing a SPECT rest imaging procedure, and comprising, before administering the $^{99m}$Tc-containing species while the subject is at rest:
  subjecting the subject to stress;
  during the stress, administering to the subject thallium having a radioactivity of between 3 and 5 mCi at a time of the administering; and
  performing SPECT stress imaging on the subject.

38. The method according to claim 26, wherein administering comprises administering the $^{99m}$Tc-containing species while the subject is at rest, wherein performing the SPECT imaging procedure comprises performing a SPECT rest imaging procedure, and comprising:
  before administering the $^{99m}$Tc-containing species while the subject is at rest:
    subjecting the subject to stress; and
    during the stress, administering to the subject thallium having a radioactivity of between 3 and 5 mCi at a time of the administering; and
  before performing the SPECT rest imaging procedure, performing SPECT stress imaging on the subject.

39. The method according to claim 26, wherein administering comprises administering the $^{99m}$Tc-containing species while the subject is at rest, wherein performing the SPECT imaging procedure comprises performing a SPECT rest imaging procedure, and comprising:
  before administering the $^{99m}$Tc-containing species while the subject is at rest:
    subjecting the subject to stress; and
    during the stress, administering to the subject thallium having a radioactivity of between 3 and 5 mCi at a time of the administering; and
  performing SPECT stress imaging on the subject simultaneously with performing the SPECT rest imaging procedure.

40. The method according to claim 26,
  wherein administering comprises subjecting the subject to stress, and administering the $^{99m}$Tc-containing species during the stress,
  wherein performing the SPECT imaging procedure comprises performing a SPECT stress imaging procedure of the $^{99m}$Tc-containing species, and comprising:
  after administering the $^{99m}$Tc-containing species, administering to the subject, while the subject is at rest, thallium having a radioactivity of between 3 and 5 mCi at a time of the administering; and
  after performing the SPECT stress imaging procedure, performing a SPECT rest imaging procedure of the thallium.

41. The method according to claim 26,
  wherein administering comprises subjecting the subject to stress, and administering the $^{99m}$Tc-containing species during the stress,
  wherein performing the SPECT imaging procedure comprises performing a SPECT stress imaging procedure of the $^{99m}$Tc-containing species, and comprising:
  before administering the $^{99m}$Tc-containing species, administering to the subject, while the subject is at rest, thallium having a radioactivity of between 3 and 5 mCi at a time of the administering; and
  performing a SPECT rest imaging procedure of the thallium, after performing the SPECT stress imaging procedure of the $^{99m}$Tc-containing species.

42. The method according to claim 26,
  wherein administering comprises subjecting the subject to stress, and administering the $^{99m}$Tc-containing species during the stress,
  wherein performing the SPECT imaging procedure comprises performing a SPECT stress imaging procedure of the $^{99m}$Tc-containing species, and comprising:
  before administering the $^{99m}$Tc-containing species, administering to the subject, while the subject is at rest, thallium having a radioactivity of between 3 and 5 mCi at a time of the administering; and
  performing a SPECT rest imaging of the thallium simultaneously with performing the SPECT stress imaging procedure of the $^{99m}$Tc-containing species.

43. The method according to claim 42, wherein administering the $^{99m}$Tc-containing species and administering the thallium comprise administering the $^{99m}$Tc-containing species and the thallium using an automated administration system that is configured to receive imaging protocol information for use with the $^{99m}$Tc-containing species and the thallium, and to administer the $^{99m}$Tc-containing species and the thallium into the subject at least in part responsively to the protocol information.

44. The method according to claim 26, wherein performing the SPECT imaging procedure comprises performing a SPECT rest imaging procedure, and wherein the method further comprises:
  administering to the subject a radiopharmaceutical agent different from the $^{99m}$Tc-containing species; and
  performing a SPECT stress imaging procedure on the ROI,
  wherein administering the $^{99m}$Tc-containing species, performing the SPECT rest imaging procedure, and performing the SPECT stress imaging procedure comprise administering the $^{99m}$Tc-containing species, performing the SPECT rest imaging procedure, and performing the SPECT stress imaging procedure while the subject remains in place at a camera of an imaging system.

45. The method according to claim 26, comprising, prior to or during performance of the SPECT imaging procedure, administering to the subject I-123 BMIPP, wherein performing the SPECT imaging procedure comprises simultaneously imaging the $^{99m}$Tc-containing species and the I-123 BMIPP.

46. The method according to claim 26, wherein performing the SPECT imaging procedure comprises performing a first SPECT imaging procedure, and comprising, after completion of the first SPECT imaging procedure:
administering to the subject at least one additional $^{99m}$Tc-containing species different from the $^{99m}$Tc-containing species having the formula $^{99m}$TcX(Y)$_3$Z; and
performing a second SPECT imaging procedure using the at least one additional $^{99m}$Tc-containing species.

47. The method according to claim 46, wherein the at least one additional $^{99m}$Tc-containing species comprises $^{99m}$Tc-sestamibi.

48. The method according to claim 46, wherein the at least one additional $^{99m}$Tc-containing species comprises $^{99m}$Tc-tetrofosmin.

49. The method according to claim 26, wherein performing the SPECT imaging procedure comprises completing image acquisition less than 6 minutes after completing the administering of the $^{99m}$Tc-containing species.

50. The method according to claim 26, wherein performing the SPECT imaging procedure of the cardiac ROI comprises performing myocardial perfusion imaging.

51. Apparatus for performing cardiac imaging, comprising an imaging system, which comprises:
SPECT imaging functionality; and
a control unit configured to drive, the imaging functionality to perform a SPECT imaging procedure on a cardiac region of interest (ROD of an adult human subject after administration to the subject of a $^{99m}$Tc-containing species having a radioactivity of less than 50 mCi at a time of the administration, wherein the imaging procedure has a image acquisition period having a duration not exceeding 5 minutes, and
wherein said $^{99m}$Tc-containing species has the formula $^{99m}$TcX(Y)$_3$Z, wherein:
X is an anion;
each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and
Z is a boron derivative of the formula B—R$_3$
wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle,
wherein the SPECT imaging functionality is configured to generate an image having a resolution of at least 7×7×7 mm.

52. The apparatus according to claim 51, wherein the radioactivity is less than 30 mCi.

53. The apparatus according to claim 51, comprising a portable computer-communicatable non-transitory data carrier containing imaging protocol information for use with the $^{99m}$Tc-containing species.

54. The apparatus according to claim 51, comprising an automated administration system, configured to receive imaging protocol information for use with the $^{99m}$Tc-containing species, and to perform at least one automated administration of the $^{99m}$Tc-containing species into the subject at least in part responsively to the protocol information.

55. The apparatus according to claim 51, wherein the control unit is configured to drive the imaging functionality to perform myocardial perfusion imaging.

56. The apparatus according to claim 51, wherein the $^{99m}$Tc-containing species as distributed within the ROI has a range of emission-intensities R, which is measured as emitted photons/unit time/volume, wherein the SPECT imaging functionality is configured to generate a reconstructed three-dimensional emission-intensity image of the ROI, and wherein at least 50% of voxels of the image have inaccuracies of less than 30% of range R.

57. A method for cardiac imaging, comprising:
subjecting an adult human subject to stress;
during the stress, administering to the subject a $^{99m}$Tc-containing species having a radioactivity of between 20 and 40 mCi at a time of the administering; and
performing a SPECT stress imaging procedure on a cardiac region of interest (ROI) of the subject, with an image acquisition period having a duration not exceeding 5 minutes; and
during the stress image acquisition period, acquiring a number of photons greater than or equal to at least one of the following numbers:
one in 5000 photons emitted from the ROI during the stress image acquisition period, and
200,000 photons emitted from a portion of the ROI, which portion has a volume of no more than 500 cc,
wherein said $^{99m}$Tc-containing species has the formula $^{99m}$TcX(Y)$_3$Z, wherein:
X is an anion;
each Y, which is independently chosen, is a vicinal dioxime having the formula HON=C(R$_1$)C(R$_2$)=NOH or a pharmaceutically acceptable salt thereof, wherein R$_1$ and R$_2$ are each independently hydrogen, halogen, alkyl, aryl, amino or a 5 or 6-membered nitrogen or oxygen containing heterocycle, or together R$_1$ and R$_2$ are —(CR$_8$CR$_9$)$_n$— wherein n is 3, 4, 5 or 6 and R$_8$ and R$_9$ are each independently hydrogen or alkyl; and
Z is a boron derivative of the formula B—R$_3$
wherein R$_3$ is hydroxy, alkyl, alkenyl, cycloalkyl, cycloalkenyl, alkoxy, carboxyalkyl, carboxyalkenyl, hydroxyalkyl, hydroxyalkenyl, alkoxyalkyl, alkoxyalkenyl, haloalkyl, haloalkenyl, aryl, arylalkyl or (R$_4$R$_5$N)-alkyl and R$_4$ and R$_5$ are each independently hydrogen, alkyl, or arylalkyl, or R$_4$ and R$_5$ when taken together with the nitrogen atom to which they are attached form a 5 or 6-membered nitrogen containing heterocycle.

58. The method according to claim 57, comprising, prior to subjecting the subject to the stress:
administering, while the subject is at rest, thallium to the subject having a radioactivity of between 2 and 5 mCi at a time of the administering; and
performing SPECT rest imaging on the subject.

59. The method according to claim 57, wherein performing the SPECT stress imaging procedure of the cardiac ROI comprises performing myocardial perfusion imaging.

* * * * *

UNITED STATES PATENT AND TRADEMARK OFFICE
CERTIFICATE OF CORRECTION

PATENT NO. : 8,610,075 B2  Page 1 of 1
APPLICATION NO. : 12/514785
DATED : December 17, 2013
INVENTOR(S) : Rousso et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 261 days.

Signed and Sealed this
Twenty-second Day of September, 2015

Michelle K. Lee
*Director of the United States Patent and Trademark Office*